US007220421B2

(12) United States Patent
George et al.

(10) Patent No.: US 7,220,421 B2
(45) Date of Patent: May 22, 2007

(54) MORAXELLA BOVIS CYTOTOXIN, CYTOTOXIN GENE, ANTIBODIES AND VACCINES FOR PREVENTION AND TREATMENT OF MORAXELLA BOVIS INFECTIONS

(75) Inventors: Lisle W. George, Davis, CA (US); John A. Angelos, Vacaville, CA (US); John F. Hess, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/884,696

(22) Filed: Jun. 19, 2001

(65) Prior Publication Data

US 2003/0035809 A1  Feb. 20, 2003

(51) Int. Cl.
*A61K 39/08* (2006.01)

(52) U.S. Cl. ............... 424/247.1; 530/300; 530/350; 530/327; 424/184.1; 424/185.1; 424/192.1

(58) Field of Classification Search ............... 530/350, 530/300, 324, 825; 424/184.1, 251.1, 823, 424/424.1, 266.1, 190.1, 244.1, 256; 435/220, 435/70.1, 5, 235.1, 516, 7.32, 32; 514/12, 514/2, 54
See application file for complete search history.

(56) References Cited

U.S. PATENT DOCUMENTS

| 5,594,107 | A | * | 1/1997 | Potter et al. ............ 530/350 |
| 5,837,268 | A | * | 11/1998 | Potter et al. ............ 424/255.1 |
| 6,096,320 | A | * | 8/2000 | Potter et al. ............ 424/255.1 |
| 6,180,112 | B1 | * | 1/2001 | Highlander et al. ..... 424/255.1 |
| 6,475,754 | B1 | * | 11/2002 | Bemis et al. ............ 435/69.1 |
| 6,797,272 | B1 | * | 9/2004 | Potter et al. ............ 424/192.1 |
| 2003/0118566 | A1 | * | 6/2003 | Neuman et al. ......... 424/93.21 |

FOREIGN PATENT DOCUMENTS

| WO | 90/07525 | * | 7/1990 |
| WO | 01/16172 | * | 3/2001 |

OTHER PUBLICATIONS

Ronald W. Ellis, Ph.D, Chapter 29, New Technologies for making vaccines, pp. 568-574, In Vaccines, W.B. Saunders, 1988.*
Boslego, JW et al, Chapter 17, Gonorrhea vaccines, pp. 211-223, In Vaccines and Immunotherapy, Edited by Stanley J. Cryz, Jr. Pergamon Press, 1991.*

(Continued)

*Primary Examiner*—Mark Navarro
*Assistant Examiner*—Ginny Allen Portner
(74) *Attorney, Agent, or Firm*—Quine Intellectual Property Law Group, P.C.

(57) ABSTRACT

*Moraxella bovis* cytotoxin and a gene encoding *Moraxella bovis* cytotoxin. Identification, isolation, cloning and identification of nucleotide sequence of the *Moraxella bovis* genes mbxA, mbxB, mbxC and mbxD, partial purification of the native cytotoxin, preparation of partially purified native and a recombinant *Moraxella bovis* cytotoxin, identification of an amino acid sequence of the cytotoxin, preparation of antibodies against the *Moraxella bovis* cytotoxin, preparation of vaccines against *Moraxella bovis*. Method for prevention and treatment of infectious bovine keratoconjunctivitis caused by *Moraxella bovis*.

5 Claims, 22 Drawing Sheets

OTHER PUBLICATIONS

Sandu, TS et al, American Journal of Veterniary Research, Jun. 1977, vol. 38(6), pp. 883-885.*

Ostle, AG etal, American Journal of Veterinary Research, Sep. 1984, vol. 45(9), pp. 1848-1851.*

Ostle, AG eta l, American Journal of Veterinary Research, May 1985, vol. 46(5), pp. 1011-1014.*

Halenda, Ruth Marrion, *Moraxella bovis* cytotoxin and cell detachment factor(seine protease, infectious bovine keratoconjunctivitis), vol. 59/08 of Dissertation Abstracts International, Feb. 1999, pp. 4031 -B, col. 2.*

Billson et al, 1994, FEMS Microbiology Letters, vol. 124, pp. 69-73.*

Billson et al, Jun. 2000, Infection and Immunity, pp. 3469-3474, vol. 68(6).*

CA2014033A (sequence alignment) Oct. 7, 1990, accession No. AAQ10727 (sequence alignment abstract only).*

Sequence Alignment, accession No. AAR86998, sequence in U.S. Pat. No. 5,475,098, filed Dec. 12, 1995, (sequence alignment abstract only).*

Sequence alignment B30169, Highlnader, SK et al, in DNA, vol. 8, pp. 15-28, 1989, (sequence alignment abstract only).*

Accession No. AAW22159, Sequence alignmnet, sequence in CA2170839A, MacInnes, J et al, (sequence alignment abstract only).*

Gray et al, Vet. Microbiol., vol. 43, pp. 183-196, 1995.*

Yamamoto, K et al. Infection and Immunity, Dec. 1990, vol. 58(12), pp. 4106-4116, Two step processing for activation of the cytolysin/Hemolysin of *Vibrio cholerae* 01 Biotype E1 Tor: Nucleotide sequence of the structural gene(hlyA) and characterization of the Processed Products.*

Billson, F. Mark et al, Infection and Immunity, Jun. 200, p. 3469-3474, vol. 68(6), Characterization of Hemolysin of *Moraxella bovis* using a hemolysis-neutralizing monoclonal antibody.*

Gray, J. T e al, Veterinary Microbiology, vol. 43, 1995, pp. 183-196, Partial Characterization of a *Moraxella bovis* cytolysin.*

Gerbig, DG et al, Infection and Immunity, May 1992, vol. 60(5), pp. 1734-1739, May 1992, Characterization of a neutralizing monoclonal antibody to *Pasteurella haemolytica leukotoxin*.*

Lally, Edward T. et al, RTX Toxins recognize a B2 integrin on the on the surface of Human target cells, The Journal of Biological Chemistry, vol. 272(48), Nov. 28, 1997, pp. 30463-30469.*

Pellett, S et al, Infection and Immunity, Aug. 1996, vol. 6, 4(8), pp. 3081-3087, Aug. 1996, *Escherichia coli* hemolysin mutants with altered target cell specifiicity.*

Smits, MA et al, Infection and Immunity, vol. 59(12), pp. 4497-4504, Dec. 1991, Cytolysins of *Actinobacillus pleuropneumoniae* serotype 9.*

Burrows, LL et al, Infection and Immunity, Dec. 1993, pp. 5001-5007, vol. 61(12), Molecular analysis of the leukotoxin determinants from Pasteurella haemolytica serotypes 1 to 16.*

Angelos, JA et al, Veterinary Microbiology, vol. 92, pp. 363-377, 2003, An RTX operon in hemolytic *Moraxella bovis* is absent from nonhemolytic strains.*

Hess, JF et al, Journal of Medical Microbiology, 2006, vol. 55, pp. 443-449, The *Moraxella bovis* RTX toxin locus mbx defines a pathogenicity island.*

Patricia S. Hoien-Dalen, et al., Comparative Characterization of the Leukocidic and Hemolytic Activity of *Moraxella bovis, Am. J. Vet. Res.*, 51/2:191-196 (Feb. 1990).

F. Mark Billson, et al., A Haemolytic Cell-free Preparation of *Moraxella bovis* Confers Protection Against Infectious Bovine Keratoconjunctivitis, *FEMS Microbiology Letters*, 124:69-73 (1994).

F. Mark Billson, et al., Characterization of Hemolysin of *Moraxella bovis* Using Hemolysis-Neutralizing Monoclonal Antibody, *Infection and Immunity*, pp. 3469-3474 (Jun. 2000).

J. T. Gray, et al., Partial Characterizatio of a *Moraxella bovis* Cytolysin, *Veterinary Microbiology*, 43:183-196, (1995).

M. K. McG. Beard, et al., Reproduction of Bovine Keratoconjunctivitis With a Purified Haemolytic and Cytotoxic Fraction of *Moraxella bovis, Veterinary Microbiology*, 42:15-33 (1994).

Michael H. Brown, et al., Infectious Bovine Keratoconjunctivitis: A Review, *J. Vet. Intern. Med.*, 12:259-266 (1998).

* cited by examiner

FIG. 3-1

```
  1 ATGTCCAATATAAATGTAATTAAATCTAATATTCAAGCAGGCTTGAATTCAACAAAGTCT   60
  1  M  S  N  I  N  V  I  K  S  N  I  Q  A  G  L  N  S  T  K  S    20

61 GGATTAAAAAATCTTTACTTGGCTATTCCCAAAGATTATGATCCGCAAAAAGGTGGGACT  120
 21  G  L  K  N  L  Y  L  A  I  P  K  D  Y  D  P  Q  K  G  G  T    40

121 TTAAATGATTTTATTAAAGCTGCTGATGAATTAGGTATTGCTCGTTTAGCAGAAGAGCCT  180
 41  L  N  D  F  E  K  A  A  D  E  L  G  I  A  R  L  A  E  E  P    60

181 AATCACACTGAAACAGCAAAAAAATCTGTTGACACAGTAAATCAGTTTCTCTCTCTCACA  240
 61  N  H  T  E  T  A  K  K  S  V  D  T  V  N  Q  F  L  S  L  T    80

241 CAAACTGGTATTGCTATTTCTGCAACAAAATTAGAAAAGTTCTTACAAAAACATTCTACC  300
 81  Q  T  G  I  A  I  S  A  T  K  L  E  K  F  L  Q  K  H  S  T   100

301 AATAAGTTAGCCAAAGGGTTAGACAGTGTAGAAAATATTGATCGTAAATTAGGTAAAGCA  360
101  N  K  L  A  K  G  L  D  S  V  E  N  I  D  R  K  L  G  K  A   120

361 AGTAATGTATTATCAACATTAAGCTCTTTTTTGGGCACTGCATTAGCGGGTATAGAACTT  420
121  S  N  V  L  S  T  L  S  S  F  L  G  T  A  L  A  G  I  E  L   140

421 GATTCTTTAATCAAAAAAGGTGATGCTGCACCTGATGCTTTGGCTAAAGCTAGTATTGAC  480
141  D  S  L  I  K  K  G  D  A  A  P  D  A  L  A  K  A  S  I  D   160

481 TTGATTAATGAGATAATTGGTAATCTATCTCAGAGTACTCAAACGATTGAAGCATTTTCT  540
161  L  I  N  E  I  I  G  N  L  S  Q  S  T  Q  T  I  E  A  F  S   180

541 TCACAGTTAGCAAAGTTAGGTTCTACTATATCGCAGGCTAAAGGCTTCTCTAATATAGGA  600
181  S  Q  L  A  K  L  G  S  T  I  S  Q  A  K  G  F  S  N  I  G   200

601 AACAAGTTGCAAAACTTAAATTTTTCTAAAACAAATCTTGGTTTGGAAATAATTACTGGT  660
201  N  K  L  Q  N  L  N  S  S  K  T  N  L  G  L  E  I  I  T  G   220

661 TTGCTATCAGGCATTTCTGCAGGCTTTGCTTTAGCGGATAAAAATGCATCGACTGGCAAA  720
221  L  L  S  G  I  S  A  G  F  A  L  A  D  K  N  A  S  T  G  K   240

721 AAAGTTGCTGCAGGTTTTGAATTAAGCAATCAAGTTATTGGTAATGTAACAAAAGCAATT  780
241  K  V  A  A  G  F  E  L  S  N  Q  V  I  G  N  V  T  K  A  I   260

781 TCTTCATATGTTTTAGCACAACGTGTTGCTGCTGGTCTATCAACTACTGGTGCTGTTGCT  840
261  S  S  Y  V  L  A  Q  R  V  A  A  G  L  S  T  T  G  A  V  A   280

841 GCTTTAATTACTTCATCGATTATGTTGGCAATTAGTCCTTTGGCATTTATGAATGCAGCA  900
281  A  L  I  T  S  S  I  M  L  A  I  S  P  L  A  F  M  N  A  A   300

901 GATAAATTCAATCATGCTAATGCTCTTGATGAGTTTGCAAAACAATTCCGAAAATTTGGC  960
301  D  K  F  N  H  A  N  A  L  D  E  F  A  K  Q  F  R  K  F  G   320
```

FIG. 3-2

```
 961 TATGATGGGGATCATTTATTGGCTGAATATCAGCGTGGTGTGGGTACTATTGAAGCTTCA 1020
 321  Y  D  G  D  H  L  L  A  E  Y  Q  R  G  V  G  T  I  E  A  S   340

1021 TTAACTACAATTAGTACGGCATTAGGTGCAGTTTCTGCTGGTGTTTCCGCTGCTGCTGTA 1080
 341  L  T  T  I  S  T  A  L  G  A  V  S  A  G  V  S  A  A  A  V   360

1081 GGATCTGCTGTTGGTGCACCGATTGCACTATTAGTTGCAGGTGTTACAGGATTGATCTCT 1140
 361  G  S  A  V  G  A  P  I  A  L  L  V  A  G  V  T  G  L  I  S   380

1141 GGAATTTTAGAAGCGTCTAAACAGGCAATGTTTGAAAGTGTTGCTAACCGTTTACAAGGT 1200
 381  G  I  L  E  A  S  K  Q  A  M  F  E  S  V  A  N  R  L  Q  G   400

1201 AAAATTTTAGAGTGGGAAAAGCAAAATGGCGGTCAGAACTATTTTGATAAAGGCTATGAT 1260
 401  K  I  L  E  W  E  K  Q  N  G  G  Q  N  Y  F  D  K  G  Y  D   420

1261 TCTCGTTATGCTGCTTATTTAGCTAATAACTTAAAATTTTTGTCTGAGCTAAATAAAGAG 1320
 421  S  R  Y  A  A  Y  L  A  N  N  L  K  F  L  S  E  L  N  K  E   440

1321 TTGGAAGCTGAACGTGTTATTGCAATCACCCAACAACGTTGGGATAATAATATTGGTGAG 1380
 441  L  E  A  E  R  V  I  A  I  T  Q  Q  R  W  D  N  N  I  G  E   460

1381 TTAGCAGGTATTACCAAATTGGGTGAACGCATTAAGAGCGGAAAAGCTTATGCAGATGCT 1440
 461  L  A  G  I  T  K  L  G  E  R  I  K  S  G  K  A  Y  A  D  A   480

1441 TTTGAAGATGGCAAGAAAGTTGAAGCTGGTTCCAATATTACTTTGGATGCTAAAACTGGT 1500
 481  F  E  D  G  K  K  V  E  A  G  S  N  I  T  L  D  A  K  T  G   500

1501 ATCATAGACATTAGTAATTCAAATGGGAAAAAAACGCAAGCGTTGCATTTCACTTCGCCT 1560
 501  I  I  D  I  S  N  S  N  G  K  K  T  Q  A  L  H  F  T  S  P   520

1561 TTGTTAACAGCAGGAACTGAATCACGTGAACGTTTAACTAATGGTAAATACTCTTATATT 1620
 521  L  L  T  A  G  T  E  S  R  E  R  L  T  N  G  K  Y  S  Y  I   540

1621 AATAAGTTAAAATTCGGACGTGTAAAAAAACTGGCAAGTTACAGATGGAGAGGCTAGTTCT 1680
 541  N  K  L  K  F  G  R  V  K  N  W  Q  V  T  D  G  E  A  S  S   560

1681 AAATTAGATTTCTCTAAAGTTATTCAGCGTGTAGCCGAGACAGAAGGCACAGACGAGATT 1740
 561  K  L  D  F  S  K  V  I  Q  R  V  A  E  T  E  G  T  D  E  I   580

1741 GGTCTAATAGTAAATGCAAAAGCTGGCAATGACGATATCTTTGTTGGTCAAGGTAAAATG 1800
 581  G  L  I  V  N  A  K  A  G  N  D  D  I  F  V  G  Q  G  K  M   600

1801 AATATTGATGGTGGAGATGGACACGATCGTGTCTTCTATAGTAAAGACGGAGGATTTGGT 1860
 601  N  I  D  G  G  D  G  H  D  R  V  F  Y  S  K  D  G  G  F  G   620

1861 AATATTACTGTAGATGGTACGAGTGCAACAGAAGCAGGCAGTTATACAGTTAATCGTAAG 1920
 621  N  I  T  V  D  G  T  S  A  T  E  A  G  S  Y  T  V  N  R  K   640
```

FIG. 3-3

```
1921 GTTGCTCGAGGTGATATCTACCATGAAGTTGTGAAGCGTCAAGAAACCAAGGTGGGTAAA 1980
 641  V  A  R  G  D  I  Y  H  E  V  V  K  R  Q  E  T  K  V  G  K   660

1981 CGTACTGAAACTATCCAGTATCGTGATTATGAATTAAGAAAAGTTGGGTATGGTTATCAG 2040
 661  R  T  E  T  I  Q  Y  R  D  Y  E  L  R  K  V  G  Y  G  Y  Q   680

2041 TCTACCGATAATTTGAAATCAGTAGAAGAAGTAATTGGTTCTCAATTTAATGATGTATTC 2100
 681  S  T  D  N  L  K  S  V  E  E  V  I  G  S  Q  F  N  D  V  F   700

2101 AAAGGTTCTAAATTCAACGACATATTCCATAGTGGTGAAGGTGATGATTTACTCGATGGT 2160
 701  K  G  S  K  F  N  D  I  F  H  S  G  E  G  D  D  L  L  D  G   720

2161 GGTGCTGGTGACGACCGCTTGTTTGGTGGTAAAGGCAACGATCGACTTTCTGGAGATGAA 2220
 721  G  A  G  D  D  R  L  F  G  G  K  G  N  D  R  L  S  G  D  E   740

2221 GGCGATGATTTACTCGATGGCGGTTCTGGTGATGATGTATTAAATGGTGGTGCTGGTAAT 2280
 741  G  D  D  L  L  D  G  G  S  G  D  D  V  L  N  G  G  A  G  N   760

2281 GATGTCTATATCTTTCGGAAAGGTGATGGTAATGATACTTTGTACGATGGCACGGGCAAT 2340
 761  D  V  Y  I  F  R  K  G  D  G  N  D  T  L  Y  D  G  T  G  N   780

2341 GATAAATTAGCATTTGCAGATGCAAATATATCTGATATTATGATTGAACGTACCAAAGAG 2400
 781  D  K  L  A  F  A  D  A  N  I  S  D  I  M  I  E  R  T  K  E   800

2401 GGTATTATAGTTAAACGAAATGATCATTCAGGTAGTATTAACATACCAAGATGGTACATA 2460
 801  G  I  I  V  K  R  N  D  H  S  G  S  I  N  I  P  R  W  Y  I   820

2461 ACATCAAATTTACAAAATTATCAAAGTAATAAAACAGATCATAAAATTGAGCAACTAATT 2520
 821  T  S  N  L  Q  N  Y  Q  S  N  K  T  D  H  K  I  E  Q  L  I   840

2521 GGTAAAGATGGTAGTTATATCACTTCCGATCAAATTGATAAAATTTTGCAAGATAAGAAA 2580
 841  G  K  D  G  S  Y  I  T  S  D  Q  I  D  K  I  L  Q  D  K  K   860

2581 GATGGTACAGTAATTACATCTCAAGAATTGAAAAAGCTTGCTGATGAGAATAAGAGCCAA 2640
 861  D  G  T  V  I  T  S  Q  E  L  K  K  L  A  D  E  N  K  S  Q   880

2641 AAATTATCTGCTTCGGACATTGCAAGTAGCTTAAATAAGCTAGTTGGGTCAATGGCACTA 2700
 881  K  L  S  A  S  D  I  A  S  S  L  N  K  L  V  G  S  M  A  L   900

2701 TTTGGTACAGCAAATAGTGTGAGTTCTAACGCCTTACAGCCAATTACACAACCAACTCAA 2760
 901  F  G  T  A  N  S  V  S  S  N  A  L  Q  P  I  T  Q  P  T  Q   920

2761 GGAATTTTGGCTCCAAGTGTTTAG     SEQ ID NO. 1                    2784
 921  G  I  L  A  P  S  V  *    SEQ ID NO. 2                     928
```

```
MbxA    AAMGSANGAP  IAELVAGVTG  DISGILEASK  QAMFEESVANR  LQGKILEWEK  ONGGQNYFDK  GYDSR  422
LktA    AANGSVIASP  IAELVSGITG  VISTLQVSK   QAMFEEHVANK  IHNKIVEWEK  NNHGKNYFEN  GYDAR  440
ApxIIA  ASAGSLFGAP  VALLVAGVIG  LITTLEEMSK  QAMEEHVANK   VHDRIVEWEK  .KHNKNYFEQ  GYDSR  444
HlyA    AATTSLFGAR  VSALVGANTG  IESGILEASK  QAMEEHYASK   MADVIAEWEK  .KHGKNYFEEN GYDAR  447 peak 23
MbxA    YAANYANNLK  FESELNKELE  AERVIAITQQ  RWDANNIGELA  GITKLGERIK  SGKAYADAFE  DGRKV  487
LktA    YLANEQDNMK  ELLNENKELQ  AERYIAFTQQ  QWDNNIGDLA   GISRLGEKML  SGKAYVDAFE  EGKHI  505
ApxIIA  HLADLQDNMK  FLINLNKEEQ  AERVVAITQQ  RWDNQIGDLA   AISRRTDKIS  SGKAVVDAFE  EGDHQ  509
HlyA    HAAFLEDNFK  IESQYNKEYS  VERSVLIETQQ HWDTLIGELA   GVTRNGDKTE  SGKSYIDYFE  EGKRL  512

MbxA    EAG....SNI  TFDAKIGFID  ISNSNGKKTQ  ABHIFTSPLI   AGTESRERLT  NGKIYSYTNKE KFFRV  548
LktA    KAD....KLV  QLDSANGIID  VSNSNGKAKTQ HILFRIPLLI   PGTEHRERVQ  TGKIYEYITKL NTMRV  566
ApxIIA  SYD....SSV  QLEDNKNGIIN ISNITNR.KIQ SVLERTPLLI   DGEENRERIQ  EGKNSVITKL  HIDRV  569
HlyA    EKKPDEFQKQ  VFDPLKGMID  LSDS..KSST  LEKFVLPLLI   RGEEIRERRQ  SGKEYGIEL   LVKGW  575

MbxA    KNMQVID.GE  ASSKLDESKV  IQRVA....ET EG....IDEI   GLIVNAKAGN  DDIFVGQGKM  NIGG   605
LktA    DSMKITD.GA  ASSTFDLTNV  VQRIGTELDN  AGNVTKIKET   KITAKLGEGD  DNVFVGSGTI  EIGEG  630
ApxIIA  DSWTVID.GD  ASSSVDETNV  VQRIAVKFDD  AGNIIESKDT   KIDANEGAGN  DNVFGSSTI   VJDGG  633
HlyA    LKNTVKGVQQ  KGSVYDYSNL  IQHASY....  .GN.NQYREI   RIESHLGDSD  DKMELSAGSA  NIYAG  634

MbxA    DGHDRVFYSK  DGGFGNIFMD  GTSAFEAGSY  FNNRQV.ARG  DIYHEVVKRQ  ETKVGKRTET  FDYRD  669
LktA    EGYDRVHYSR  .GNYGAFHID  APKEEEQESY  FNNRFV.ETG  KAHEVTSEH   TALVGNREEK  RENR   692
ApxIIA  DGHDRVHYSR  .GFYGALVED  ATAEFGKGSY  SMKAYE.GDS  KAHLETIATH  QINVENREEK  LEMR   695
HlyA    KGHDVMYMDK  T.DTGVRTID  GEKAIFAGNY  LVTRVLGGDV  KVEQEVVKEQ  EVSVGKRTER  TQYRS  698
```

```
                                                                          peak 26
MbxA    YELRKV.GYG  VQSTDNEKSV  PEVTGSQFMD  VFKGSKEND.  FHSGEGPDLL  DGGAGDDREF  GGKGN  733
LktA    HSNNQH.HAG  MYTKDTLKAM  ELTTGITSHND TFKGSKFNDA  HNGGDGVDTI  DGNDGNDRLF  GGKGD  756
ApxIIA  REDDRF.HTG  VTVTDSLKSV  EETTGTETND  TFKGSQFDDV  EHGGNGYDTI  DGNDGDDHLF  GGAGD  759
HlyA    YEFTHINGKN  LTETDNLYSV  EELIGITTRAD KFFGSKFADI  EHGADGDHL   EDNDGNDRLY  GDKGN  763

MbxA    DRLSGDEGGD  ............................................................  742
LktA    DILDGGNGD.  ............................................................  765
ApxIIA  DMIDGGNGN.  ............................................................  768
HlyA    DTLSGGNGDD  QLYGGDGNDK  LIGGAGNNYL  NGGDGDDELQ  VQGNSLAKNV  LSGGKGNDKL  YGSEG  828

MbxA    .DLEDGGSGD  DMLNGGAGND  VYTFRKGDGN  DTLYDGTG.N  DKLAFADANL  SDIMIERTKE  GTIVK  805
LktA    .DFIDGGKGN  DLLHGGKGDD  LFVHRKGDGN  DTITDSDG.N  DKLLSESDSN  KDETFEKVKH  NEVI.  827
ApxIIA  .NFEVGGTGN  DITISGGKGND VYAHTGDGN  DSLTDSGG.Q  DKLAFSDVNL  KDLTEKKVDS  SDEI.  830
HlyA    ADLDGGFEGN  DLIKGGYGND  EYRYLSGYGH  HEIDDDGGKD  DKESLADIDF  RDVAERREGN  DEHMY  893

MbxA    RND.......  HSGSINTPRW  Y.....ITSNL QNYQSNKTDH  KIEEQLTGKDG SYFTSQQIDK  IEQDK  859
LktA    TNS.......  KKERVITQNW  FREAGFAKENA PNYKATK.BE  KTEEFTGQNF  ERITSKQVBD  I..A   882
ApxIIA  INQ.......  KGEKVRHIGMW FLEDILASTV  ANYKATN.DR  KFEELTGRGG  ERITSEQVDK  LK.K   885
HlyA    KAEGNVLSIG  HENGITFKNW  FEKE..SGDI  SNFQ........ LEQIFDKDG  RVIPISLKK   ALEYQ  949

MbxA    KDGTVFTSQE  LKKLADENKS  QKLSASDIAS  SENKLVGSMA  LFGTANSVSS  NAHQPITQP.  QGILA  924
LktA    KGNGKLTDDE LSKIVDNYEL  LKLHSKNYTN  SLDKITSSVS  AR.TSSNDSR  NVI..VA.PT  SM.D   941
ApxIIA  EGNNQESAEA  SKVVNDYNT  SKLDRQNYSN  SAKLSSSKG   SFLTSSSDFK  NNLGTYV.PS  S.ID   945
HlyA    QSNNK.ASYV  YGNDALAYGS  .QGNLNPLIN  ETISKNTLSAAE NEDVKEERAA ASLLQLSG.N  ASDFS  1011

MbxA    PSV------  ........  ........  ........  ........
LktA    QSL.SLQFAR  AA
ApxIIA  VS.NNFQVAR  AAQ
HlyA    YGRNSFTITA  SA
                927
                953
                956
                1023
```

```
  1 ATGGGTGGTGATACTTCTTTAATTAGACTTAATTTACAAACCCTTAATAGTAATTTAGTT   60
  1 M  G  G  D  T  S  L  I  R     N  L  Q  T  L  N  S  N  L  V    20

61 ATGATAGATTATGCTCAACAACCTGCTCTATCTGCTCTGGTTATCCTTGCCAAATACTAT  120
 21 M  I  D  Y  A  Q  Q  P  A  L  S  A  L  V  I  L  A  K  Y  Y    40

121 GGTATTTCTGCAAGTCCAGCAGACATTATGCATCAGTTTTCTGATAATACAAAAGGAGAC  180
 41 G  I  S  A  S  P  A  D  I  M  H  Q  F  S  D  N  T  K  G  D    60

181 CTGAATGAAATTGAATGGATGTTGGCAGCAAAGAAATTAGAATTAAAGGTAAAGATTATA  240
 61 L  N  E  I  E  W  M  L  A  A  K  K  L  E  L  K  V  K  I  I    80

241 AAACAGCCTTTAACTCGATTGTCAATGATAACACTTCCTGCTTTGGTGTGGTGTGATAAT  300
 81 K  Q  P  L  T  R  L  S  M  I  T  L  P  A  L  V  W  C  D  N   100

301 AAGCCCGATTTAGATCAAAATTTAAACTCTCATTTTATACTAACTAAAATTGATGGGGTG  360
101 K  P  D  L  D  Q  N  L  N  S  H  F  I  L  T  K  I  D  G  V   120

361 GGATCTGCTGCAAAATATCTCATCTACGATTTGATTGAGAATCGTCCCATAATATTAGAT  420
121 G  S  A  A  K  Y  L  I  Y  D  L  I  E  N  R  P  I  I  L  D   140

421 GCAAGTGAGTTTTCTGAAAGATATTCTGGTAAGTTAATGCTAGTAACTTCCCGTGCGTCA  480
141 A  S  E  F  S  E  R  Y  S  G  K  L  M  L  V  T  S  R  A  S   160

481 ATATTGGGTTCATTGGCTAAATTTGATTTTACTTGGTTTATTCCTGCGGTAATCAAATAT  540
161 I  L  G  S  L  A  K  F  D  F  T  W  F  I  P  A  V  I  K  Y   180

541 CGTTATATTTTTTTTGAAGTCATCGTTATTTCAGTGGTGCTACAGATTTTTGCTCTGATT  600
181 R  Y  I  F  F  E  V  I  V  I  S  V  V  L  Q  I  F  A  L  I   200

601 ACGCCATTGTTTTTTCAGGTTGTGATGGATAAGGTATTGGTGCATCGTGGTTTTTCTACT  660
201 T  P  L  F  F  Q  V  V  M  D  K  V  L  V  H  R  G  F  S  T   220

661 CTGGATGTGGTAGCGATTGCCTTGTTGGTAGTAAGTTTATTTGAAGTCATTTTAAGTGGT  720
221 L  D  V  V  A  I  A  L  L  V  V  S  L  F  E  V  I  L  S  G   240

721 CTACGCACTTATATTTTTGCTCATACAACCTCTCGAATTGATGTAGAGCTAGGAGCACGA  780
241 L  R  T  Y  I  F  A  H  T  T  S  R  I  D  V  E  L  G  A  R   260

781 TTATTTCGTCATCTATTAGCTCTACCGCTTGCTTATTTTGAGAGTAGAAGAGTAGGCGAT  840
261 L  F  R  H  L  L  A  L  P  L  A  Y  F  E  S  R  R  V  G  D   280

841 ACAGTTGCACGTATACGTGAATTGGAACATATCCGCAATTTCTTAACTGGTCAAGCTCTC  900
281 T  V  A  R  I  R  E  L  E  H  I  R  N  F  L  T  G  Q  A  L   300

901 ACTTCAGTTTTAGATTTGGTGTTTTCTTTTATATTCTTGTTTGTAATGTGGTATTACAGC  960
301 T  S  V  L  D  L  V  F  S  F  I  F  L  F  V  M  W  Y  Y  S   320
```

FIG. 8-2

```
961  CCTACTTTAACACTGGTAGTTTTGGCATCATTACCAATATATGCGTTTTGGTCTGCCTTT 1020
321   P  T  L  T  L  V  V  L  A  S  L  P  I  Y  A  F  W  S  A  F   340

1021 ATTAGCCCAATTTTACGCACTCGACTAAATGATCAATTTGCACGCAATGCAGATAATCAA 1080
341   I  S  P  I  L  R  T  R  L  N  Q  F  A  R  N  A  D  N  Q    360

1081 TCTTTTTTAGTGGAAAGTATTACTGCGGTTGGTACGGTAAAAGCAATGGCAGTTGAACCT 1140
361   S  F  L  V  E  S  I  T  A  V  G  T  V  K  A  M  A  V  E  P   380

1141 CAAATGACCCGTCGCTGGGATAATCAATTAGCAGCTTATGTGGTTTCTAGTTTTCGGGTA 1200
381   Q  M  T  R  R  W  D  N  Q  L  A  A  Y  V  V  S  S  F  R  V   400

1201 GCTAAGTTGGCAATGGTTGGGCAGCAAGGAGTACAACTCATTCAAAAGATGGTTATTGTG 1260
401   A  K  L  A  M  V  G  Q  Q  G  V  Q  L  I  Q  K  M  V  I  V   420

1261 GCAACTCTATGGATTGGTGCAAAATTGGTAATTGAAGGCAAGCTATCGGTAGGTCAATTA 1320
421   A  T  L  W  I  G  A  K  L  V  I  E  G  K  L  S  V  G  Q  L   440

1321 ATAGCATTTAATATGCTGGCAGGTCAGGTGGCCGCTCCTGTTATCCGCCTGGCACAGCTA 1380
441   I  A  F  N  M  L  A  G  Q     A  A  P  V  I  R  L  A  Q  L   460

1381 TGGCAAGATTTTCAGCAAGTAGGTATTTCAGTGGCGAGATTGGGTGATATTTTAAATACT 1440
461   W  Q  D  F  Q  Q  V  G  I  S  V  A  R  L  G  D  I  L  N  T   480

1441 CCAACTGAGCATTCTACATCTCGCTTAACTTTACCTGATATTAAGGGTGATATTACATTT 1500
481   P  T  E  H  S  T  S  R  L  T  L  P  D  I  K  G  D  I  T  F   500

1501 GAAAATGTTGATTTTCGCTACAAAATAGATGGGCATTTAATATTACAGAATTTAAATTTA 1560
501   E  N  V  D  F  R  Y  K  I  D  G  H  L  I  L  Q  N  L  N  L   520

1561 CAGATTAACGCTGGAGAGATACTAGGTATCGTAGGACGCTCTGGTTCAGGTAAATCAACA 1620
521   Q  I  N  A  G  E  I  L  G  I  V  G  R  S  G  S  G  K  S  T   540

1621 TTGACAAAATTAGTACAGCGTTTATATGTACCAGAAAATGGGCGAATATTAGTTGATGGA 1680
541   L  T  K  L  V  Q  R  L  Y  V  P  E  N  G  R  I  L  V  D  G   560

1681 AACGATTTGGCATTAGCTGATCCCGCTTGGCTGCGTCGCCAAGTGGGTGTTGTTTTGCAG 1740
561   N  D  L  A  L  A  D  P  A  W  L  R  R  Q  V  G  V  V  L  Q   580

1741 GAAAATGTGTTACTCAATCGTAGTATTCGAGATAATATTGCCCTAACTGATACGGGCATG 1800
581   E  N  V  L  L  N  R  S  I  R  D  N  I  A  L  T  D  T  G  M   600

1801 TCATTAGAGTTTATTATCCAGGCTGCCAAGATGTCTGGGGCACATGACTTTATTATGGAA 1860
601   S  L  E  F  I  I  Q  A  A  K  M  S  G  A  H  D  F  I  M  E   620

1861 TTGCCTGAGGGTTATGATACGATTGTTGGAGAGCAAGGTGCAGGCTTGTCAGGTGGACAA 1920
621   L  P  E  G  Y  D  T  I  V  G  E  Q  G  A  G  L  S  G  G  Q   640
```

FIG. 8-3

```
1921 CGCCAGCGTATCGCTATTGCGCGTGCTTTAATTACCAATCCGCGTATTTTGATTTTTGAT 1980
 641  R  Q  R  I  A  I  A  R  A  L  I  T  N  P  R  I  L  I  F  D      660

1981 GAAGCTACTAGTGCATTAGACTATGAGTCGGAAAGGGCTATTATGCAAAATATGCAGGCA 2040
 661  E  A  T  S  A  L  D  Y  E  S  E  R  A  I  M  Q  N  M  Q  A      680

2041 ATTTGCCAAGGTAGAACAGTGTTGATTATTGCACATCGCTTATCTACCGTAAAAATGGCA 2100
 681  I  C  Q  G  R  T  V  L  I  I  A  H  R  L  S  T  V  K  M  A      700

2101 CATCGCATTATTGCAATGGACAAGGGGAAAATTGTAGAGCAAGGCACACATCAAGAATTG 2160
 701  H  R  I  I  A  M  D  K  G  K  I  V  E  Q  G  T  H  Q  E  L      720

2161 TTGCAAAAAGAAGATGGTTACTATCGTTATTTATATGATTTGCAGAATGGATAAA          2215
 721  L  Q  K  E  D  G  Y  Y  R  Y  L  Y  D  L  Q  N  G  *
```

```
MbxB  ------MED MAQQPAESA EMEAAKKYG ISASPADDM DNEIEWML AAKKEEL 55
LktB  MEANHQRND L..... GEVA ETMEAQYHN ISLNPEELK .IS TAWLL AAKSSAL 56
ApxIB MDFYRE.ED V...... GLYA LSILAQYHN TAVNPEELK .D TAWEL AAKSEL 55
HlyB  MDSCHK.ED V...... GEVA LFILAQHHN VSVNPEEKK .CE TSWE AAKSLEL 55

MbxB  KVKIIKQPL TRBSMETEP ALNNCDNKP DLDQNLNSH FETKIEGV GSAAKYLIY DLLENRP 116
LktB  KAKHIKKEL SRDHLVNEP ALVWQDN.. ......GKH QLVKB.. TDNRYELY NLEQDAF 107
ApxIB KAKQVKKA. DREAFIALP ALVWRED.. ......GKH PLIKD... NEAKKYEIF DEETHNP 106
HlyB  KVKQVKKTL DRNEISEP AEVWRED.. ......GRH FLGTKVS.. KEANRVEIF DLEQNP 106

MbxB  IEEDASEES ERNSGKLME VTSRASILG SEAKFDFIW FIPAVIKYR YEEFEMVVI SVVEQE 177
LktB  QSLSTDEFE ACYQGQLIL VTSRASWG QLAKFDFIW FLPAVIKYR KIFLETLIV SIFLQE 168
ApxIB RLEQAEFFE SLKQGKLIL VASRASING KLAKRDFIW FLPAVIKYR KISTEIEV SIFKQLE 167
HlyB  RVLEQSEPE AAVQGHTIL IASRSSVAG KLEAKFDFIM FIPATRKYR REIEIEIW SVEQLF 167

MbxB  ALIPLFFQ VVMDKVLVH AIAGLVHSE TVATAI VIT FEVI SGI-R TYIFAHSIS 238
LktB  ALIPLERQ VVMDKVLVH TVARAI VII TVARAI VII FEIV SGIR TYVFSHSTS 229
ApxIB ALIPLFFQ VVMDKVLVH TVALAI ME KVALAI ME FEEH NBLR VIFAHSIS 228
HlyB  ALIPLFFQ VVMDKVLVH TVAI SVKW IASRSSVAG FEII SGER YIFAHSTS 228

MbxB  ARLFRHLLA KPLANFESR RELEHEHNF RELDQIRNF LTGOALTSV DLMFSEFE LEFMVNY 299
LktB  AKLERHLUS CPISYFENR RELDEKEAR RELDEKEAR LTGDALTSV DLFLSEIE AVMNNY 290
ApxIB ARLFRHLLA LPLSNFENR RELDEKFAR RELDEKFAR LTGOACTSV DLMFSEFE AVMLNY 289
HlyB  AKLERHICA LPISWFESR RRLGDIKSFL LTGOALTSV DLGFSFIE AVMKLG 289

MbxB  SFLFLEVWE ASCILYAFM GAFTSPIER TRENDQFAR NADNQSFLV ESIFAVGFM KAMAYEF 360
LktB  SRKLEHVLG GSEPGYILV STFFSPLR RRLDEKFAR SADNQAFCA ESVIFAVMNI KAMADAR 351
ApxIB SBRKTLVLG GSLQFTYGM SLFISPLR RRLDEKFAR GADNQYECV ESVIALNEP KCLAVTP 350
HlyB  SRKGTSVEE FSLPGYBALE SVEISPLR RRLGDIKSFR NADNQSFLV ESVIALNTE KAMDANSK 350
```

| | | | | | | | |
|---|---|---|---|---|---|---|---|
| MbxB | QMTRRWDNG | LAAYVVSSE | RYAKLAMVG | QQGVQLFQK | MLIVATEWL | GAKEVJEGK | ESVGQLI 421 |
| LktB | QMTDTMDKQ | LASYVSSSE | RIVALATIG | QQGVQLQIK | TJPMINLWE | GAHLVISGQ | LSTGQLI 412 |
| ApxIB | QMTNTWDKQ | LASYVSAGE | RVTLLATIG | QQGVQFIQK | VMMVITLWE | GAHLVISGQ | LSIGQLI 411 |
| HlyB | QMTNIMDKQ | LAGYVAAGE | KVIVLATIG | QQGIQLQIK | FVMTINLWE | GAHLVSSGQ | LSRGQLI 411 |
| | | | | | | | |
| MbxB | AFNMLAGQY | AAPVIREAQ | LWQDFQQVE | ISVARLGDI | LNIPTEHST | SRIFEPDIK | GDITFEN 482 |
| LktB | AFAMLSGQV | TAPVIRLAQ | LWQDFQQNG | LSVIRLGDV | LNSPIEQVQ | GKLSEPEIK | GDISFKN 473 |
| ApxIB | AFNMLSGQV | LAPVIRLAQ | LWQDFQQVG | ISVIRLGDM | ENSPIESYQ | GKLALPEIK | GDITFRN 472 |
| HlyB | AFNMLAGQI | MAPVIRLAQ | IWQDFQQVG | LSVIRLGDV | ENSPIESYH | GKLALPEIN | GDITFRN 472 |
| | | | | | | | |
| MbxB | VDFRYKIDG | HLTEQNLNE | QINAGEILG | IVGRSGSGK | STLIKLVQR | LMVPENGRI | LVDGNDE 543 |
| LktB | IRFRYKPDA | RTILLNAVAL | ENRQGEVTG | IVGRSGSGK | STLLKALQR | RVIPENGQV | E-DGHDI 534 |
| ApxIB | IRFRYKPDA | PVILNDVNL | SIQQGEVIG | IVGRSGSGK | STLTKLIQR | FIPENGQV | LIDGHDL 533 |
| HlyB | IRFRYKPDS | PVLQDNINL | SIKQGEVIG | IVGRSGSGK | STLIKLIQR | FYPENGQV | LIDGHDL 533 |
| | | | | | | | |
| MbxB | ALADPAWER | RQVGVVLQE | NWLENRSTR | DNIAITDTG | MSLEFTLQA | AKMSGAHDF | IMELPEG 604 |
| LktB | ALADPNWER | RQIGVVLQD | NVALLNRSIR | ENIALSDPG | MPMERVEYA | AKLAGAHDF | ISELREG 595 |
| ApxIB | ALADPNWER | RQVGVVLQD | NVLENRSIR | DNIALADPG | MPMEKIVHA | AKLAGAHDF | ISELREG 594 |
| HlyB | ALADPNWER | RQVGVVLQD | NVVENRSII | DNVSLANEG | MSVEKVEYA | AKLAGAHDF | ISELREG 594 |
| | | | | | | | |
| MbxB | VDIIVGEQG | AGLSGGQRQ | RIAIARALI | TNRKLLIED | EATSALDYE | SERATMQNM | QAFEQGR 665 |
| LktB | VNIIVGEQG | AGLSGGQRQ | RIALARALJ | MNPKILIED | EATSALDYE | SEHIIMQNM | QKEQQGR 656 |
| ApxIB | VNIIVGEEQG | AGLSGGQRQ | RIAIARALN | MNPKELIED | EATSALDYE | SEHIMRNM | HQEQKGR 655 |
| HlyB | VNIIVGEQG | AGLSGGQRQ | RIALARALN | NRRKILIED | EATSALDYE | SEHIMRNM | HKIQKGR 655 |
| | | | | | | | |
| MbxB | TVLIIAHRL | STVKNAHRI | LAMDGKIV | EQQTHQECA | QKEDQVIRY | DYDLENG 717 | |
| LktB | TVLIIAHRL | STVKNADRI | TVMEKGELI | EQGKHHEL | QNSNGLQSY | LHSIQLN 708 | |
| ApxIB | TVLIIAHRL | STVKNADRI | LVMEKGQIV | EDGKHHGELJ | ADPNGLVHV | LHQQSE 707 | |
| HlyB | TVLIIAHRL | STVKNADRI | LVMEKGKIV | EQEKHHKEL | SERESLISV | EYQLQSD 707 | |

FIG. 10

```
  1 ATGACGAAAAAGTTTGCAGAGCTAGGTTTAATTGCATGGCTTTGGTCTAACTCTGATATG    60
  1  M  T  K  K  F  A  E  L  G  L  I  A  W  L  W  S  N  S  D  M    20

61 CATAAACATTGGACGTTGTCTTTGTTTGCGACCAATGTTATTCCGGCAATTGAGACAGGT   120
 21  H  K  H  W  T  L  S  L  F  A  T  N  V  I  P  A  I  E  T  G    40

121 CAATATGTTATATTGAAAAGAGAAGATATGCCTGTAGCATATTGTAGTTGGGCTAAACTT   180
 41  Q  Y  V  I  L  K  R  E  D  M  P  V  A  Y  C  S  W  A  K  L    60

181 AGTTTAGAAAACGAGGTTAAATATATTAACGATGTTACTTCTCTTAAGTTAGATGACTGG   240
 61  S  L  E  N  E  V  K  Y  I  N  D  V  T  S  L  K  L  D  D  W    80

241 CAGTCAGGTGACCGAAACTGGTTTATTGACTGGATTGCTCCATTTGGCGATAGTCTTACA   300
 81  Q  S  G  D  R  N  W  F  I  D  W  I  A  P  F  G  D  S  L  T   100

301 CTCACAAAACACATGAGAACGTTATTTTCAGATGAATTGTTTAGAGCGATTCGTGTAGAT   360
101  L  T  K  H  M  R  T  L  F  S  D  E  L  F  R  A  I  R  V  D   120

361 GGAAATTCATCGCATGGTAAGATATCTGAATTTTATGGAAAGTCTGTTGATTCAAAATTA   420
121  G  N  S  S  H  G  K  I  S  E  F  Y  G  K  S  V  D  S  K  L   140

421 GCCTCAAGAATATTTGCACAATATCACGAAGATTTGACGAGCAAATTGTCAACTCAGAAT   480
141  A  S  R  I  F  A  Q  Y  H  E  D  L  T  S  K  L  S  T  Q  N   160

481 AATTTTATTATATCTAAAGATAATTAA                                     507
161  N  F  I  I  S  K  D  N  *                                    169
```

```
  1 ATGTTTATACAAGCACTTAAAGATTTTTTTATTCGCTATATAACCGTTTGGCGCAATACA   60
  1  M  F  I  Q  A  L  K  D  F     I  R  Y  I  T  V  W  R  N  T

61 TGGGCAGTTCGAGACCAACTAACCCCTCCTAAGCGTACTAAAGAAGAACTCGCTTTTCTT  120
 21  W  A  V  R  D  Q  L  T  P  P  K  R  T  K  E  E  L  A  F  L   40

121 CCTGCACATCTAGAACTCACTGACACACCTGTATCCAGATCTTCTAAGTGGACAGCTAGA  180
 41  P  A  H  L  E  L  T  D  T  P  V  S  R  S  S  K  W  T  A  R   60

181 ATAATCATGATATTTGTCCTATTTGCTTTGCTATGGTCTTGGGTTGGACAGATTGACATT  240
 61  I  I  M  I  F  V  L  F  A  L  L  W  S  W  V  G  Q  I  D  I   80

241 GTTGCTACAGCTTCAGGTAAAATTTCTTCAGGTAGCCGTAGCAAGACTATTCAATCTTTG  300
 81  V  A  T  A  S  G  K  I  S  S  G  S  R  S  K  T  I  Q  S  L  100

301 GAAACAGCGATAGTTAAAGCAGTTTATGTACGTGATGGTCAAAATGTTCAACAAGGTGAA  360
101  E  T  A  I  V  K  A  V  Y  V  R  D  G  Q  N  V  Q  Q  G  E  120

361 ATATTAGTAGATTTAGTGGGAATCGGTTCAGATAGTGATGTTGCTCAGTCCGAGAAAGCC  420
121  I  L  V  D  L  V  G  I  G  S  D  S  D  V  A  Q  S  E  K  A  140

421 CTTCGAGCAGCGCAATTATCTAAGCTACGCCTTGAAGCAATTTTATCAGCATTAAATCAC  480
141  L  R  A  A  Q  L  S  K  L  R  L  E  A  I  L  S  A  L  N  H  160

481 CGTATTAATCCTCAGATTGATGTAGCATATGCAAAGTCTTTAAATATTTCAGAATCGGAA  540
161  R  I  N  P  Q  I  D  V  A  Y  A  K  S  L  N  I  S  E  S  E  180

541 ATTAATGAAGCTCAAACTTTAGCCCAAAATCAATATCAAGCATGGTTAGCACAAGATGAA  600
181  I  N  E  A  Q  T  L  A  Q  N  Q  Y  Q  A  W  L  A  Q  D  E  200

601 CAACTAAAAATTAACCTTAAAAGGACATCAAGCAGAATTACAATCTGCTCGATCCCAAGAA  660
201  Q  L  K  L  T  L  K  G  H  Q  A  E  L  Q  S  A  R  S  Q  E  220

661 CAAAAGTTGGTTTCAGTTGGTGCAATTGAACATCAAAAGACTGATGATTATCGGAGTCTC  720
221  Q  K  L  V  S  V  G  A  I  E  H  Q  K  T  D  D  Y  R  S  L  240

721 AAAGCAGAAAATTTTATATCTGAGCATGCTTATCTAGAACAAGAAAGCAAATTACTTAGC  780
241  K  A  E  N  F  I  S  E  H  A  Y  L  E  Q  E  S  K  L  L  S  260

781 AATCAAAATGATTTACAAAGTACACGTAGTCAGATTCAAAAAATACAGGCTGCAATCATG  840
261  N  Q  N  D  L  Q  S  T  R  S  Q  I  Q  K  I  Q  A  A  I  M  280

841 CAAGCTGAACAGAACCGTATGTTATATACTCAAAATCTAAAACGTGATACATTAGAATCT  900
281  Q  A  E  Q  N  R  M  L  Y  T  Q  N  L  K  R  D  T  L  E  S  300

901 TTACGCCAAACCAATGAACAGATTAATCAATATACTGGTCAAACTAATAAAGCTAAGCAG  960
301  L  R  Q  T  N  E  Q  I  N  Q  Y  T  G  Q  T  N  K  A  K  Q  320
```

FIG. 12-2

```
 961 CGACAGAAATTGCTGAGTATTAAATCACCTGTTAATGGTACTATACAAGAGCTAACAGCT 1020
 321  R  Q  K  L  L  S  I  K  S  P  V  N  G  T  I  Q  E  L  T  A   340

1021 TATACTTTAGGTGGAGTTGTACAAGCAGCACAAAAAATTATGGTTGTGGCACCTAACGAT 1080
 341  Y  T  L  G  G  V  V  Q  A  A  Q  K  I  M  V  V  A  P  N  D   360

1081 AATCAAGTGGAAGTAGAGGTATTAGTGCTAAATAAAGATATCGGCTTTGTAAAAGCTGGG 1140
 361  N  Q  V  E  V  E  V  L  V  L  N  K  D  I  G  F  V  K  A  G   380

1141 CAGAATGTTATCATCAAAATCGAGAGTTTTCCTTATACACGTTATGGTTATTTAACAGGT 1200
 381  Q  N  V  I  I  K  I  E  S  F  P  Y  T  R  Y  G  Y  L  T  G   400

1201 AAAATAAAAAGTATTAGTCATGATGCTATAGAACATCAACATTTAGGTCTAGTGTATACT 1260
 401  K  I  K  S  I  S  H  D  A  I  E  H  Q  H  L  G  L  V  Y  T   420

1261 GCACTTGTTTCTCTTGATAAAAGCACATTAAATATAGATGGAGTAACAATCAACTTAACG 1320
 421  A  L  V  S  L  D  K  S  T  L  N  I  D  G  V  T  I  N  L  T   440

1321 CCAGGAATGAATGTTACTGCTGAAATTAAAACAGGTAAACGTCGTGTTTTGGATTATATA 1380
 441  P  G  M  N  V  T  A  E  I     T  G  K  R  R  V  L  D  Y  I   461

1381 TTAAGTCCATTGCAGACAAAAGTTGATGAAAGTTTTCGAGAACGCTAA             1428
 461  L  S  P  L  Q  T  K  V  D  E  S  F  R  E  R  *              476
```

FIG. 13-1

```
MbxD  --MFIQAEKD  FELRYIFVWR  NFMAVRDQLT  PRKRITKEELA  FLPAHEELTQ    48
LktD  MRIJWLSGIYE  FFLRYKNIWA  FVMKIRKKELD  HPNRKKDESE  FLPAHEELIE    50
ApxID MKTWLMGLYE   FFQRYKTVWI  ELNKIRHQED  TPDREKDENE   FLPAHEELIE    50
HlyD  MKTWLMGFSE   FLERYKLVWS  ETMKIRKQLD  EDVREKDENE   FLSGRSKEIK    50

MbxD  TPVSRSSKMT   ARIEMIFVLF  AELLWSWVQGI  DLVATASGKI  SSGSRSKTLQ    98
LktD  TPVSKRPRL    AYLIMEFLWV  ATIVLASVSKV  EIVATAPGKI  FFSSGRSKEJK  100
ApxID TPVSKKPRLE   AYIMEFLFL   ALVISIVSHM   EIVATATGKV  AFSDRSKEIK   100
HlyD  TPVSRRPRLM   AVFLMGEEVI  AFTLESVLGQV  ELVAFANGKL  ELSGRSKEIK   100

MbxD  SLEITAIVKAV  VRDGGQNVQQ  GEEIVDIEVGI  GSESEDVAQSE  KAEDRAAQESK  148
LktD  PIENAIVQET   FVKDGQFVEK  GQVIVSETAL   GSPADIKKTM  ASLSEAKLEN  150
ApxID PIENALVKE    EVQDGQEVEK  DQLLHIEFTAL  GADADQQKIK  SSLSETKLER  150
HlyD  PIENSIVKEI   IKEGESVRKK  GDVLKETAL    GAEAEDTLKTQ  SSLQARLEQ   150

MbxD  LRLEATHSAL   NHRINPQEDV  AYAKSL.NIS   ESEINEAQTE  AQNQYQAWLA  197
LktD  YRYQTLTAI    EKESEPVIDI  .SRTEEKDSS   EEDRERJKHE  EEEQYTTWQK  199
ApxID YRVELILEAV   AADRELIEL   .TKDEFKHAT   EEDKTRIRYL  ITEQFEAWQK  199
HlyD  IRQLESRSE    ELNKEFELKE  PDEPYFQNVS   EEEVERLTSE   IKEQFSTWQN  200

MbxD  QDEQLKEIEK   GHQAELQSAR  SQEQRLVSVG   AIEHQKTDDV  RSEKAENFES  247
LktD  QKTDKIEAYK   RKEAEKQTIF  AYMRKFEGAT   RLEQEKEKQF  KALYKQKSLS  249
ApxID QKYQKELQLQ   RREAEKQTVE  ANIRKYEGIS   RVENERKQL   KKLFNSKSTS  249
HlyD  QKYQKSENLED  KRFAERLITLE ARENRENVS    RVEKSREDDE  RSLLHKQAFA  250

MbxD  ERAYIEQESK   ELSNQNQLQS  TRSQIQKIQA   AIMQAEQNRM  QVFFQNLKRDI  297
LktD  KHELEAQENK   LIEAQNAVAV  VRSKENELEN   DLLNVKEELE  ITQFEKSDV   299
ApxID KHDVLIDENR   HESAVNELAV  YKSRENEVES   DLRQAKEEIH  EIQLFRADI   299
HlyD  KHAVLEQENK   YMEAVREERM  AKSQLEQFES   ELESAKQEYQ  LVIQLFKNEL  300
```

FIG. 13-2

```
MbxD   FESPRQNEQ  INQMFGQTNK  AKQRQKLLSI  KSPYNGTIQE  STAYTLGGVV  347
LktD   LEKIKQHIEN  ERQLRELELK  NNQRRQASMI  RAPVSGTVQQ  KIHTIGGVV   349
ApxID  LESLKQNVEA  EKQLSEELEK  NEQRQIASVL  RAPVSGTVQQ  KTHTVGGVV   349
HlyD   DKERQTDS    IELIELEK    NEERQQASYI  RAPVSGKVQQ  KVHTEGGVV   350

MbxD   QAAQKIMMVA  PNDNQVEVEV  VLNKDIGEV   KAGQNVIEKI  ESPYIRVGY   397
LktD   TTAELMIIV   PEDQMEATA   VPNKQLGEV   AAGQEVIIKV  ELFPYIRVGY  399
ApxID  TTAELMVIA   PEDDYLEVA   ITQNKQILGFI TFPYIRVGY               399
HlyD   TTAELMVIV   PQDLIEVATA  LVQNKQNYFI  LVQGNAFIKV  EAPYIRVGY   400

MbxD   LTGKIKSESH  DAIEQHLEGU  VMYTAEMVSLDK STEEN.IDAVT INTTPGMNV   446
LktD   LTGRIKIHISP DAIEQPNVGL  VENATIABDR  KNLTSPDGRK  DESSGMTIT   449
ApxID  LVGKVKMTTS  EAIEHPQEGL  WANSELIDR   KIESGKDGKE  LEGGMVSVI   449
HlyD   EVGKVKNENL  EAIEDQKEGL  VEQMENSVEE  NDLEST.GNKH IPESSGMAVI  449

MbxD   AEJAKTGKNRV LDYLDISEIQT KMDESLFRER  475
LktD   AENKIGERSM  MSXLLSQLEE  SYTESLRER   478
ApxID  ALLKTGENSV  ISYELLSPLEE SVSESLRER   478
HlyD   AEIKIGMESV  ESVLLSPLEE  SVTESLHER   478
```

Number of calves affected weekly in 1 group of vaccinated calves and in controls.

SEQUENCE LISTING

```
<160> NUMBER OF SEQ ID NOS: 41

<210> SEQ ID NO 1
<211> LENGTH: 2784
<212> TYPE: DNA
<213> ORGANISM: Moraxella bovis
<220> FEATURE:
<221> NAME/KEY: CDS
<222> LOCATION: (1)..(2781)

<400> SEQUENCE: 1 atg tcc aat ata aat gta att aaa tct aat att caa gca ggc ttg aat      48
Met Ser Asn Ile Asn Val Ile Lys Ser Asn Ile Gln Ala Gly Leu Asn
 1               5                  10                  15 tca aca aag tct gga tta aaa aat ctt tac ttg gct att ccc aaa gat      96
Ser Thr Lys Ser Gly Leu Lys Asn Leu Tyr Leu Ala Ile Pro Lys Asp
             20                  25                  30 tat gat ccg caa aaa ggt ggg act tta aat gat ttt att aaa gct gct     144
Tyr Asp Pro Gln Lys Gly Gly Thr Leu Asn Asp Phe Ile Lys Ala Ala
         35                  40                  45 gat gaa tta ggt att gct cgt tta gca gaa gag cct aat cac act gaa     192
Asp Glu Leu Gly Ile Ala Arg Leu Ala Glu Glu Pro Asn His Thr Glu
     50                  55                  60 aca gca aaa aaa tct gtt gac aca gta aat cag ttt ctc tct ctc aca     240
Thr Ala Lys Lys Ser Val Asp Thr Val Asn Gln Phe Leu Ser Leu Thr
 65                  70                  75                  80 caa act ggt att gct att tct gca aca aaa tta gaa aag ttc tta caa     288
Gln Thr Gly Ile Ala Ile Ser Ala Thr Lys Leu Glu Lys Phe Leu Gln
                 85                  90                  95 aaa cat tct acc aat aag tta gcc aaa ggg tta gac agt gta gaa aat     336
Lys His Ser Thr Asn Lys Leu Ala Lys Gly Leu Asp Ser Val Glu Asn
            100                 105                 110 att gat cgt aaa tta ggt aaa gca agt aat gta tta tca aca tta agc     384
Ile Asp Arg Lys Leu Gly Lys Ala Ser Asn Val Leu Ser Thr Leu Ser
        115                 120                 125 tct ttt ttg ggc act gca tta gcg ggt ata gaa ctt gat tct tta atc     432
```

```
                 Ser Phe Leu Gly Thr Ala Leu Ala Gly Ile Glu Leu Asp Ser Leu Ile
                     130                 135                 140 aaa aaa ggt gat gct gca cct gat gct ttg gct aaa gct agt att gac      480
Lys Lys Gly Asp Ala Ala Pro Asp Ala Leu Ala Lys Ala Ser Ile Asp
145                 150                 155                 160 ttg att aat gag ata att ggt aat cta tct cag agt act caa acg att      528
Leu Ile Asn Glu Ile Ile Gly Asn Leu Ser Gln Ser Thr Gln Thr Ile
                    165                 170                 175 gaa gca ttt tct tca cag tta gca aag tta ggt tct act ata tcg cag      576
Glu Ala Phe Ser Ser Gln Leu Ala Lys Leu Gly Ser Thr Ile Ser Gln
                180                 185                 190 gct aaa ggc ttc tct aat ata gga aac aag ttg caa aac tta aat ttt      624
Ala Lys Gly Phe Ser Asn Ile Gly Asn Lys Leu Gln Asn Leu Asn Phe
            195                 200                 205 tct aaa aca aat ctt ggt ttg gaa ata att act ggt ttg cta tca ggc      672
Ser Lys Thr Asn Leu Gly Leu Glu Ile Ile Thr Gly Leu Leu Ser Gly
        210                 215                 220 att tct gca ggc ttt gct tta gcg gat aaa aat gca tcg act ggc aaa      720
Ile Ser Ala Gly Phe Ala Leu Ala Asp Lys Asn Ala Ser Thr Gly Lys
225                 230                 235                 240 aaa gtt gct gca ggt ttt gaa tta agc aat caa gtt att ggt aat gta      768
Lys Val Ala Ala Gly Phe Glu Leu Ser Asn Gln Val Ile Gly Asn Val
                    245                 250                 255 aca aaa gca att tct tca tat gtt tta gca caa cgt gtt gct gct ggt      816
Thr Lys Ala Ile Ser Ser Tyr Val Leu Ala Gln Arg Val Ala Ala Gly
                260                 265                 270 cta tca act act ggt gct gtt gct gct tta att act tca tcg att atg      864
Leu Ser Thr Thr Gly Ala Val Ala Ala Leu Ile Thr Ser Ser Ile Met
            275                 280                 285 ttg gca att agt cct ttg gca ttt atg aat gca gca gat aaa ttc aat      912
Leu Ala Ile Ser Pro Leu Ala Phe Met Asn Ala Ala Asp Lys Phe Asn
        290                 295                 300 cat gct aat gct ctt gat gag ttt gca aaa caa ttc cga aaa ttt ggc      960
His Ala Asn Ala Leu Asp Glu Phe Ala Lys Gln Phe Arg Lys Phe Gly
305                 310                 315                 320 tat gat ggg gat cat tta ttg gct gaa tat cag cgt ggt gtg ggt act     1008
Tyr Asp Gly Asp His Leu Leu Ala Glu Tyr Gln Arg Gly Val Gly Thr
                    325                 330                 335 att gaa gct tca tta act aca att agt acg gca tta ggt gca gtt tct     1056
Ile Glu Ala Ser Leu Thr Thr Ile Ser Thr Ala Leu Gly Ala Val Ser
                340                 345                 350 gct ggt gtt tcc gct gct gct gta gga tct gct gtt ggt gca ccg att     1104
Ala Gly Val Ser Ala Ala Ala Val Gly Ser Ala Val Gly Ala Pro Ile
            355                 360                 365 gca cta tta gtt gca ggt gtt aca gga ttg atc tct gga att tta gaa     1152
Ala Leu Leu Val Ala Gly Val Thr Gly Leu Ile Ser Gly Ile Leu Glu
        370                 375                 380 gcg tct aaa cag gca atg ttt gaa agt gtt gct aac cgt tta caa ggt     1200
Ala Ser Lys Gln Ala Met Phe Glu Ser Val Ala Asn Arg Leu Gln Gly
385                 390                 395                 400 aaa att tta gag tgg gaa aag caa aat ggc ggt cag aac tat ttt gat     1248
Lys Ile Leu Glu Trp Glu Lys Gln Asn Gly Gly Gln Asn Tyr Phe Asp
                    405                 410                 415 aaa ggc tat gat tct cgt tat gct gct tat tta gct aat aac tta aaa     1296
Lys Gly Tyr Asp Ser Arg Tyr Ala Ala Tyr Leu Ala Asn Asn Leu Lys
                420                 425                 430 ttt ttg tct gag cta aat aaa gag ttg gaa gct gaa cgt gtt att gca     1344
Phe Leu Ser Glu Leu Asn Lys Glu Leu Glu Ala Glu Arg Val Ile Ala
            435                 440                 445
```

```
                                            -continued atc acc caa caa cgt tgg gat aat aat att ggt gag tta gca ggt att    1392
Ile Thr Gln Gln Arg Trp Asp Asn Asn Ile Gly Glu Leu Ala Gly Ile
    450                 455                 460 acc aaa ttg ggt gaa cgc att aag agc gga aaa gct tat gca gat gct    1440
Thr Lys Leu Gly Glu Arg Ile Lys Ser Gly Lys Ala Tyr Ala Asp Ala
465                 470                 475                 480 ttt gaa gat ggc aag aaa gtt gaa gct ggt tcc aat att act ttg gat    1488
Phe Glu Asp Gly Lys Lys Val Glu Ala Gly Ser Asn Ile Thr Leu Asp
                485                 490                 495 gct aaa act ggt atc ata gac att agt aat tca aat ggg aaa aaa acg    1536
Ala Lys Thr Gly Ile Ile Asp Ile Ser Asn Ser Asn Gly Lys Lys Thr
            500                 505                 510 caa gcg ttg cat ttc act tcg cct ttg tta aca gca gga act gaa tca    1584
Gln Ala Leu His Phe Thr Ser Pro Leu Leu Thr Ala Gly Thr Glu Ser
        515                 520                 525 cgt gaa cgt tta act aat ggt aaa tac tct tat att aat aag tta aaa    1632
Arg Glu Arg Leu Thr Asn Gly Lys Tyr Ser Tyr Ile Asn Lys Leu Lys
    530                 535                 540 ttc gga cgt gta aaa aac tgg caa gtt aca gat gga gag gct agt tct    1680
Phe Gly Arg Val Lys Asn Trp Gln Val Thr Asp Gly Glu Ala Ser Ser
545                 550                 555                 560 aaa tta gat ttc tct aaa gtt att cag cgt gta gcc gag aca gaa ggc    1728
Lys Leu Asp Phe Ser Lys Val Ile Gln Arg Val Ala Glu Thr Glu Gly
                565                 570                 575 aca gac gag att ggt cta ata gta aat gca aaa gct ggc aat gac gat    1776
Thr Asp Glu Ile Gly Leu Ile Val Asn Ala Lys Ala Gly Asn Asp Asp
            580                 585                 590 atc ttt gtt ggt caa ggt aaa atg aat att gat ggt gga gat gga cac    1824
Ile Phe Val Gly Gln Gly Lys Met Asn Ile Asp Gly Gly Asp Gly His
        595                 600                 605 gat cgt gtc ttc tat agt aaa gac gga gga ttt ggt aat att act gta    1872
Asp Arg Val Phe Tyr Ser Lys Asp Gly Gly Phe Gly Asn Ile Thr Val
    610                 615                 620 gat ggt acg agt gca aca gaa gca ggc agt tat aca gtt aat cgt aag    1920
Asp Gly Thr Ser Ala Thr Glu Ala Gly Ser Tyr Thr Val Asn Arg Lys
625                 630                 635                 640 gtt gct cga ggt gat atc tac cat gaa gtt gtg aag cgt caa gaa acc    1968
Val Ala Arg Gly Asp Ile Tyr His Glu Val Val Lys Arg Gln Glu Thr
                645                 650                 655 aag gtg ggt aaa cgt act gaa act atc cag tat cgt gat tat gaa tta    2016
Lys Val Gly Lys Arg Thr Glu Thr Ile Gln Tyr Arg Asp Tyr Glu Leu
            660                 665                 670 aga aaa gtt ggg tat ggt tat cag tct acc gat aat ttg aaa tca gta    2064
Arg Lys Val Gly Tyr Gly Tyr Gln Ser Thr Asp Asn Leu Lys Ser Val
        675                 680                 685 gaa gaa gta att ggt tct caa ttt aat gat gta ttc aaa ggt tct aaa    2112
Glu Glu Val Ile Gly Ser Gln Phe Asn Asp Val Phe Lys Gly Ser Lys
    690                 695                 700 ttc aac gac ata ttc cat agt ggt gaa ggt gat gat tta ctc gat ggt    2160
Phe Asn Asp Ile Phe His Ser Gly Glu Gly Asp Asp Leu Leu Asp Gly
705                 710                 715                 720 ggt gct ggt gac gac cgc ttg ttt ggt ggt aaa ggc aac gat cga ctt    2208
Gly Ala Gly Asp Asp Arg Leu Phe Gly Gly Lys Gly Asn Asp Arg Leu
                725                 730                 735 tct gga gat gaa ggc gat gat tta ctc gat ggc ggt tct ggt gat gat    2256
Ser Gly Asp Glu Gly Asp Asp Leu Leu Asp Gly Gly Ser Gly Asp Asp
            740                 745                 750 gta tta aat ggt ggt gct ggt aat gat gtc tat atc ttt cgg aaa ggt    2304
Val Leu Asn Gly Gly Ala Gly Asn Asp Val Tyr Ile Phe Arg Lys Gly
        755                 760                 765
```

```
gat ggt aat gat act ttg tac gat ggc acg ggc aat gat aaa tta gca    2352
Asp Gly Asn Asp Thr Leu Tyr Asp Gly Thr Gly Asn Asp Lys Leu Ala
770                 775                 780 ttt gca gat gca aat ata tct gat att atg att gaa cgt acc aaa gag    2400
Phe Ala Asp Ala Asn Ile Ser Asp Ile Met Ile Glu Arg Thr Lys Glu
785                 790                 795                 800 ggt att ata gtt aaa cga aat gat cat tca ggt agt att aac ata cca    2448
Gly Ile Ile Val Lys Arg Asn Asp His Ser Gly Ser Ile Asn Ile Pro
            805                 810                 815 aga tgg tac ata aca tca aat tta caa aat tat caa agt aat aaa aca    2496
Arg Trp Tyr Ile Thr Ser Asn Leu Gln Asn Tyr Gln Ser Asn Lys Thr
            820                 825                 830 gat cat aaa att gag caa cta att ggt aaa gat ggt agt tat atc act    2544
Asp His Lys Ile Glu Gln Leu Ile Gly Lys Asp Gly Ser Tyr Ile Thr
            835                 840                 845 tcc gat caa att gat aaa att ttg caa gat aag aaa gat ggt aca gta    2592
Ser Asp Gln Ile Asp Lys Ile Leu Gln Asp Lys Lys Asp Gly Thr Val
850                 855                 860 att aca tct caa gaa ttg aaa aag ctt gct gat gag aat aag agc caa    2640
Ile Thr Ser Gln Glu Leu Lys Lys Leu Ala Asp Glu Asn Lys Ser Gln
865                 870                 875                 880 aaa tta tct gct tcg gac att gca agt agc tta aat aag cta gtt ggg    2688
Lys Leu Ser Ala Ser Asp Ile Ala Ser Ser Leu Asn Lys Leu Val Gly
                885                 890                 895 tca atg gca cta ttt ggt aca gca aat agt gtg agt tct aac gcc tta    2736
Ser Met Ala Leu Phe Gly Thr Ala Asn Ser Val Ser Ser Asn Ala Leu
            900                 905                 910 cag cca att aca caa cca act caa gga att ttg gct cca agt gtt tag    2784
Gln Pro Ile Thr Gln Pro Thr Gln Gly Ile Leu Ala Pro Ser Val
            915                 920                 925

<210> SEQ ID NO 2
<211> LENGTH: 927
<212> TYPE: PRT
<213> ORGANISM: Moraxella bovis

<400> SEQUENCE: 2

Met Ser Asn Ile Asn Val Ile Lys Ser Asn Ile Gln Ala Gly Leu Asn
1               5                   10                  15

Ser Thr Lys Ser Gly Leu Lys Asn Leu Tyr Leu Ala Ile Pro Lys Asp
            20                  25                  30

Tyr Asp Pro Gln Lys Gly Gly Thr Leu Asn Asp Phe Ile Lys Ala Ala
        35                  40                  45

Asp Glu Leu Gly Ile Ala Arg Leu Ala Glu Glu Pro Asn His Thr Glu
    50                  55                  60

Thr Ala Lys Lys Ser Val Asp Thr Val Asn Gln Phe Leu Ser Leu Thr
65                  70                  75                  80

Gln Thr Gly Ile Ala Ile Ser Ala Thr Lys Leu Glu Lys Phe Leu Gln
                85                  90                  95

Lys His Ser Thr Asn Lys Leu Ala Lys Gly Leu Asp Ser Val Glu Asn
            100                 105                 110

Ile Asp Arg Lys Leu Gly Lys Ala Ser Asn Val Leu Ser Thr Leu Ser
        115                 120                 125

Ser Phe Leu Gly Thr Ala Leu Ala Gly Ile Glu Leu Asp Ser Leu Ile
    130                 135                 140

Lys Lys Gly Asp Ala Ala Pro Asp Ala Leu Ala Lys Ala Ser Ile Asp
145                 150                 155                 160
```

-continued

```
Leu Ile Asn Glu Ile Ile Gly Asn Leu Ser Gln Ser Thr Gln Thr Ile
                165                 170                 175
Glu Ala Phe Ser Ser Gln Leu Ala Lys Leu Gly Ser Thr Ile Ser Gln
            180                 185                 190
Ala Lys Gly Phe Ser Asn Ile Gly Asn Lys Leu Gln Asn Leu Asn Phe
        195                 200                 205
Ser Lys Thr Asn Leu Gly Leu Glu Ile Ile Thr Gly Leu Leu Ser Gly
210                 215                 220
Ile Ser Ala Gly Phe Ala Leu Ala Asp Lys Asn Ala Ser Thr Gly Lys
225                 230                 235                 240
Lys Val Ala Ala Gly Phe Glu Leu Ser Asn Gln Val Ile Gly Asn Val
                245                 250                 255
Thr Lys Ala Ile Ser Ser Tyr Val Leu Ala Gln Arg Val Ala Ala Gly
            260                 265                 270
Leu Ser Thr Thr Gly Ala Val Ala Ala Leu Ile Thr Ser Ser Ile Met
        275                 280                 285
Leu Ala Ile Ser Pro Leu Ala Phe Met Asn Ala Ala Asp Lys Phe Asn
290                 295                 300
His Ala Asn Ala Leu Asp Glu Phe Ala Lys Gln Phe Arg Lys Phe Gly
305                 310                 315                 320
Tyr Asp Gly Asp His Leu Leu Ala Glu Tyr Gln Arg Gly Val Gly Thr
                325                 330                 335
Ile Glu Ala Ser Leu Thr Thr Ile Ser Thr Ala Leu Gly Ala Val Ser
            340                 345                 350
Ala Gly Val Ser Ala Ala Val Gly Ser Ala Val Gly Ala Pro Ile
        355                 360                 365
Ala Leu Leu Val Ala Gly Val Thr Gly Leu Ile Ser Gly Ile Leu Glu
        370                 375                 380
Ala Ser Lys Gln Ala Met Phe Glu Ser Val Ala Asn Arg Leu Gln Gly
385                 390                 395                 400
Lys Ile Leu Glu Trp Glu Lys Gln Asn Gly Gly Gln Asn Tyr Phe Asp
                405                 410                 415
Lys Gly Tyr Asp Ser Arg Tyr Ala Ala Tyr Leu Ala Asn Asn Leu Lys
            420                 425                 430
Phe Leu Ser Glu Leu Asn Lys Glu Leu Glu Ala Glu Arg Val Ile Ala
        435                 440                 445
Ile Thr Gln Gln Arg Trp Asp Asn Asn Ile Gly Glu Leu Ala Gly Ile
450                 455                 460
Thr Lys Leu Gly Glu Arg Ile Lys Ser Gly Lys Ala Tyr Ala Asp Ala
465                 470                 475                 480
Phe Glu Asp Gly Lys Lys Val Glu Ala Gly Ser Asn Ile Thr Leu Asp
                485                 490                 495
Ala Lys Thr Gly Ile Ile Asp Ile Ser Asn Ser Asn Gly Lys Lys Thr
            500                 505                 510
Gln Ala Leu His Phe Thr Ser Pro Leu Leu Thr Ala Gly Thr Glu Ser
        515                 520                 525
Arg Glu Arg Leu Thr Asn Gly Lys Tyr Ser Tyr Ile Asn Lys Leu Lys
530                 535                 540
Phe Gly Arg Val Lys Asn Trp Gln Val Thr Asp Gly Glu Ala Ser Ser
545                 550                 555                 560
Lys Leu Asp Phe Ser Lys Val Ile Gln Arg Val Ala Glu Thr Glu Gly
                565                 570                 575
Thr Asp Glu Ile Gly Leu Ile Val Asn Ala Lys Ala Gly Asn Asp Asp
```

```
                580                 585                 590
Ile Phe Val Gly Gln Gly Lys Met Asn Ile Asp Gly Asp Gly His
            595                 600                 605

Asp Arg Val Phe Tyr Ser Lys Asp Gly Phe Gly Asn Ile Thr Val
610                 615                 620

Asp Gly Thr Ser Ala Thr Glu Ala Gly Ser Tyr Thr Val Asn Arg Lys
625                 630                 635                 640

Val Ala Arg Gly Asp Ile Tyr His Glu Val Lys Arg Gln Glu Thr
            645                 650                 655

Lys Val Gly Lys Arg Thr Glu Thr Ile Gln Tyr Arg Asp Tyr Glu Leu
            660                 665                 670

Arg Lys Val Gly Tyr Gly Tyr Gln Ser Thr Asp Asn Leu Lys Ser Val
            675                 680                 685

Glu Glu Val Ile Gly Ser Gln Phe Asn Asp Val Phe Lys Gly Ser Lys
            690                 695                 700

Phe Asn Asp Ile Phe His Ser Gly Glu Gly Asp Leu Leu Asp Gly
705                 710                 715                 720

Gly Ala Gly Asp Asp Arg Leu Phe Gly Gly Lys Gly Asn Asp Arg Leu
            725                 730                 735

Ser Gly Asp Glu Gly Asp Asp Leu Leu Asp Gly Gly Ser Gly Asp Asp
            740                 745                 750

Val Leu Asn Gly Gly Ala Gly Asn Asp Val Tyr Ile Phe Arg Lys Gly
            755                 760                 765

Asp Gly Asn Asp Thr Leu Tyr Asp Gly Thr Gly Asn Asp Lys Leu Ala
770                 775                 780

Phe Ala Asp Ala Asn Ile Ser Asp Ile Met Ile Glu Arg Thr Lys Glu
785                 790                 795                 800

Gly Ile Ile Val Lys Arg Asn Asp His Ser Gly Ser Ile Asn Ile Pro
            805                 810                 815

Arg Trp Tyr Ile Thr Ser Asn Leu Gln Asn Tyr Gln Ser Asn Lys Thr
            820                 825                 830

Asp His Lys Ile Glu Gln Leu Ile Gly Lys Asp Gly Ser Tyr Ile Thr
            835                 840                 845

Ser Asp Gln Ile Asp Lys Ile Leu Gln Asp Lys Lys Asp Gly Thr Val
850                 855                 860

Ile Thr Ser Gln Glu Leu Lys Lys Leu Ala Asp Glu Asn Lys Ser Gln
865                 870                 875                 880

Lys Leu Ser Ala Ser Asp Ile Ala Ser Ser Leu Asn Lys Leu Val Gly
            885                 890                 895

Ser Met Ala Leu Phe Gly Thr Ala Asn Ser Val Ser Ser Asn Ala Leu
            900                 905                 910

Gln Pro Ile Thr Gln Pro Thr Gln Gly Ile Leu Ala Pro Ser Val
            915                 920                 925

<210> SEQ ID NO 3
<211> LENGTH: 953
<212> TYPE: PRT
<213> ORGANISM: Pasteurella haemolytica

<400> SEQUENCE: 3

Met Gly Thr Arg Leu Thr Thr Leu Ser Asn Gly Leu Lys Asn Thr Leu
1               5                   10                  15

Thr Ala Thr Lys Ser Gly Leu His Lys Ala Gly Gln Ser Leu Thr Gln
            20                  25                  30
```

-continued

```
Ala Gly Ser Ser Leu Lys Thr Gly Ala Lys Lys Ile Ile Leu Tyr Ile
            35                  40                  45
Pro Gln Asn Tyr Gln Tyr Asp Thr Glu Gln Gly Asn Gly Leu Gln Asp
        50                  55                  60
Leu Val Lys Ala Ala Glu Glu Leu Gly Ile Glu Val Gln Arg Glu Glu
 65                  70                  75                  80
Arg Asn Asn Ile Ala Thr Ala Gln Thr Ser Leu Gly Thr Ile Gln Thr
                85                  90                  95
Ala Ile Gly Leu Thr Glu Arg Gly Ile Val Leu Ser Ala Pro Gln Ile
                100                 105                 110
Asp Lys Leu Leu Gln Lys Thr Lys Ala Gly Gln Ala Leu Gly Ser Ala
            115                 120                 125
Glu Ser Ile Val Gln Asn Ala Asn Lys Ala Lys Thr Val Leu Ser Gly
    130                 135                 140
Ile Gln Ser Ile Leu Gly Ser Val Leu Ala Gly Met Asp Leu Asp Glu
145                 150                 155                 160
Ala Leu Gln Asn Asn Ser Asn Gln His Ala Leu Ala Lys Ala Gly Leu
                165                 170                 175
Glu Leu Thr Asn Ser Leu Ile Glu Asn Ile Ala Asn Ser Val Lys Thr
                180                 185                 190
Leu Asp Glu Phe Gly Glu Gln Ile Ser Gln Phe Gly Ser Lys Leu Gln
            195                 200                 205
Asn Ile Lys Gly Leu Gly Thr Leu Gly Asp Lys Leu Lys Asn Ile Gly
    210                 215                 220
Gly Leu Asp Lys Ala Gly Leu Gly Leu Asp Val Ile Ser Gly Leu Leu
225                 230                 235                 240
Ser Gly Ala Thr Ala Ala Leu Val Leu Ala Asp Lys Asn Ala Ser Thr
                245                 250                 255
Ala Lys Lys Val Gly Ala Gly Phe Glu Leu Ala Asn Gln Val Val Gly
                260                 265                 270
Asn Ile Thr Lys Ala Val Ser Ser Tyr Ile Leu Ala Gln Arg Val Ala
            275                 280                 285
Ala Gly Leu Ser Ser Thr Gly Pro Val Ala Ala Leu Ile Ala Ser Thr
    290                 295                 300
Val Ser Leu Ala Ile Ser Pro Leu Ala Phe Ala Gly Ile Ala Asp Lys
305                 310                 315                 320
Phe Asn His Ala Lys Ser Leu Glu Ser Tyr Ala Glu Arg Phe Lys Lys
                325                 330                 335
Leu Gly Tyr Asp Gly Asp Asn Leu Leu Ala Glu Tyr Gln Arg Gly Thr
                340                 345                 350
Gly Thr Ile Asp Ala Ser Val Thr Ala Ile Asn Thr Ala Leu Ala Ala
            355                 360                 365
Ile Ala Gly Gly Val Ser Ala Ala Ala Gly Ser Val Ile Ala Ser
    370                 375                 380
Pro Ile Ala Leu Leu Val Ser Gly Ile Thr Gly Val Ile Ser Thr Ile
385                 390                 395                 400
Leu Gln Tyr Ser Lys Gln Ala Met Phe Glu His Val Ala Asn Lys Ile
                405                 410                 415
His Asn Lys Ile Val Glu Trp Glu Lys Asn Asn His Gly Lys Asn Tyr
                420                 425                 430
Phe Glu Asn Gly Tyr Asp Ala Arg Tyr Leu Ala Asn Leu Gln Asp Asn
            435                 440                 445
Met Lys Phe Leu Leu Asn Leu Asn Lys Glu Leu Gln Ala Glu Arg Val
```

-continued

```
            450                 455                 460
Ile Ala Ile Thr Gln Gln Trp Asp Asn Asn Ile Gly Asp Leu Ala
465                 470                 475                 480
Gly Ile Ser Arg Leu Gly Glu Lys Val Leu Ser Gly Lys Ala Tyr Val
                485                 490                 495
Asp Ala Phe Glu Glu Gly Lys His Ile Lys Ala Asp Lys Leu Val Gln
            500                 505                 510
Leu Asp Ser Ala Asn Gly Ile Ile Asp Val Ser Asn Ser Gly Lys Ala
            515                 520                 525
Lys Thr Gln His Ile Leu Phe Arg Thr Pro Leu Leu Thr Pro Gly Thr
530                 535                 540
Glu His Arg Glu Arg Val Gln Thr Gly Lys Tyr Glu Tyr Ile Thr Lys
545                 550                 555                 560
Leu Asn Ile Asn Arg Val Asp Ser Trp Lys Ile Thr Asp Gly Ala Ala
                565                 570                 575
Ser Ser Thr Phe Asp Leu Thr Asn Val Val Gln Arg Ile Gly Ile Glu
            580                 585                 590
Leu Asp Asn Ala Gly Asn Val Thr Lys Thr Lys Glu Thr Lys Ile Ile
            595                 600                 605
Ala Lys Leu Gly Glu Gly Asp Asp Asn Val Phe Val Gly Ser Gly Thr
        610                 615                 620
Thr Glu Ile Asp Gly Gly Glu Gly Tyr Asp Arg Val His Tyr Ser Arg
625                 630                 635                 640
Gly Asn Tyr Gly Ala Leu Thr Ile Asp Ala Thr Lys Glu Thr Glu Gln
                645                 650                 655
Gly Ser Tyr Thr Val Asn Arg Phe Val Glu Thr Gly Lys Ala Leu His
                660                 665                 670
Glu Val Thr Ser Thr His Thr Ala Leu Val Gly Asn Arg Glu Glu Lys
                675                 680                 685
Ile Glu Tyr Arg His Ser Asn Asn Gln His His Ala Gly Tyr Tyr Thr
            690                 695                 700
Lys Asp Thr Leu Lys Ala Val Glu Glu Ile Ile Gly Thr Ser His Asn
705                 710                 715                 720
Asp Ile Phe Lys Gly Ser Lys Phe Asn Asp Ala Phe Asn Gly Gly Asp
                725                 730                 735
Gly Val Asp Thr Ile Tyr Gly Asn Asp Gly Asn Asp Arg Leu Phe Gly
                740                 745                 750
Gly Lys Gly Asp Asp Ile Leu Asp Gly Asn Gly Asp Asp Phe Ile
                755                 760                 765
Asp Gly Gly Lys Gly Asn Asp Leu Leu His Gly Gly Lys Gly Asp Asp
770                 775                 780
Ile Phe Val His Arg Lys Gly Asp Gly Asn Asp Ile Ile Thr Asp Ser
785                 790                 795                 800
Asp Gly Asn Asp Lys Leu Ser Phe Ser Asp Ser Asn Leu Lys Asp Leu
                805                 810                 815
Thr Phe Glu Lys Val Lys His Asn Leu Val Ile Thr Asn Ser Lys Lys
            820                 825                 830
Glu Lys Val Thr Ile Gln Asn Trp Phe Arg Glu Ala Asp Phe Ala Lys
            835                 840                 845
Glu Val Pro Asn Tyr Lys Ala Thr Lys Asp Glu Lys Ile Glu Glu Ile
            850                 855                 860
Ile Gly Gln Asn Gly Glu Arg Ile Thr Ser Lys Gln Val Asp Asp Leu
865                 870                 875                 880
```

```
Ile Ala Lys Gly Asn Gly Lys Ile Thr Gln Asp Glu Leu Ser Lys Val
                885                 890                 895

Val Asp Asn Tyr Glu Leu Leu Lys His Ser Lys Asn Val Thr Asn Ser
            900                 905                 910

Leu Asp Lys Leu Ile Ser Ser Val Ser Ala Phe Thr Ser Ser Asn Asp
            915                 920                 925

Ser Arg Asn Val Leu Val Ala Pro Thr Ser Met Leu Asp Gln Ser Leu
        930                 935                 940

Ser Ser Leu Gln Phe Ala Arg Ala Ala
945                 950
```

<210> SEQ ID NO 4
<211> LENGTH: 956
<212> TYPE: PRT
<213> ORGANISM: Actinobacillus pleuropneumoniae

<400> SEQUENCE: 4

```
Met Ser Lys Ile Thr Leu Ser Ser Leu Lys Ser Ser Leu Gln Gln Gly
1               5                   10                  15

Leu Lys Asn Gly Lys Asn Lys Leu Asn Gln Ala Gly Thr Thr Leu Lys
            20                  25                  30

Asn Gly Leu Thr Gln Thr Gly His Ser Leu Gln Asn Gly Ala Lys Lys
        35                  40                  45

Leu Ile Leu Tyr Ile Pro Gln Gly Tyr Asp Ser Gly Gln Gly Asn Gly
    50                  55                  60

Val Gln Asp Leu Val Lys Ala Ala Asn Asp Leu Gly Ile Glu Val Trp
65                  70                  75                  80

Arg Glu Glu Arg Ser Asn Leu Asp Ile Ala Lys Thr Ser Phe Asp Thr
                85                  90                  95

Thr Gln Lys Ile Leu Gly Phe Thr Asp Arg Gly Ile Val Leu Phe Ala
            100                 105                 110

Pro Gln Leu Asp Asn Leu Leu Lys Lys Asn Pro Lys Ile Gly Asn Thr
        115                 120                 125

Leu Gly Ser Ala Ser Ser Ile Ser Gln Asn Ile Gly Lys Ala Asn Thr
    130                 135                 140

Val Leu Gly Gly Ile Gln Ser Ile Leu Gly Ser Val Leu Ser Gly Val
145                 150                 155                 160

Asn Leu Asn Glu Leu Leu Gln Asn Lys Asp Pro Asn Gln Leu Glu Leu
                165                 170                 175

Ala Lys Ala Gly Leu Glu Leu Thr Asn Glu Leu Val Gly Asn Ile Ala
            180                 185                 190

Ser Ser Val Gln Thr Val Asp Ala Phe Ala Glu Gln Ile Ser Lys Leu
        195                 200                 205

Gly Ser His Leu Gln Asn Val Lys Gly Leu Gly Gly Leu Ser Asn Lys
    210                 215                 220

Leu Gln Asn Leu Pro Asp Leu Gly Lys Ala Ser Leu Gly Leu Asp Ile
225                 230                 235                 240

Ile Ser Gly Leu Leu Ser Gly Ala Ser Ala Gly Leu Ile Leu Ala Asp
                245                 250                 255

Lys Glu Ala Ser Thr Glu Lys Lys Ala Ala Gly Val Glu Phe Ala
            260                 265                 270

Asn Gln Ile Ile Gly Asn Val Thr Lys Ala Val Ser Ser Tyr Ile Leu
        275                 280                 285

Ala Gln Arg Val Ala Ser Gly Leu Ser Ser Thr Gly Pro Val Ala Ala
```

```
                290                 295                 300
Leu Ile Ala Ser Thr Val Ala Leu Ala Val Ser Pro Leu Ser Phe Leu
305                 310                 315                 320
Asn Val Ala Asp Lys Phe Lys Gln Ala Asp Leu Ile Lys Ser Tyr Ser
                325                 330                 335
Glu Arg Phe Gln Lys Leu Gly Tyr Asp Gly Asp Arg Leu Leu Ala Asp
                340                 345                 350
Phe His Arg Glu Thr Gly Thr Ile Asp Ala Ser Val Thr Thr Ile Asn
                355                 360                 365
Thr Ala Leu Ala Ala Ile Ser Gly Gly Val Gly Ala Ala Ser Ala Gly
370                 375                 380
Ser Leu Val Gly Ala Pro Val Ala Leu Leu Val Ala Gly Val Thr Gly
385                 390                 395                 400
Leu Ile Thr Thr Ile Leu Glu Tyr Ser Lys Gln Ala Met Phe Glu His
                405                 410                 415
Val Ala Asn Lys Val His Asp Arg Ile Val Glu Trp Glu Lys Lys His
                420                 425                 430
Asn Lys Asn Tyr Phe Glu Gln Gly Tyr Asp Ser Arg His Leu Ala Asp
                435                 440                 445
Leu Gln Asp Asn Met Lys Phe Leu Ile Asn Leu Asn Lys Glu Leu Gln
                450                 455                 460
Ala Glu Arg Val Val Ala Ile Thr Gln Gln Arg Trp Asp Asn Gln Ile
465                 470                 475                 480
Gly Asp Leu Ala Ala Ile Ser Arg Arg Thr Asp Lys Ile Ser Ser Gly
                485                 490                 495
Lys Ala Tyr Val Asp Ala Phe Glu Glu Gly Gln His Gln Ser Tyr Asp
                500                 505                 510
Ser Ser Val Gln Leu Asp Asn Lys Asn Gly Ile Ile Asn Ile Ser Asn
                515                 520                 525
Thr Asn Arg Lys Thr Gln Ser Val Leu Phe Arg Thr Pro Leu Leu Thr
                530                 535                 540
Pro Gly Glu Glu Asn Arg Glu Arg Ile Gln Glu Gly Lys Asn Ser Tyr
545                 550                 555                 560
Ile Thr Lys Leu His Ile Gln Arg Val Asp Ser Trp Thr Val Thr Asp
                565                 570                 575
Gly Asp Ala Ser Ser Val Asp Phe Thr Asn Val Val Gln Arg Ile
                580                 585                 590
Ala Val Lys Phe Asp Asp Ala Gly Asn Ile Ile Glu Ser Lys Asp Thr
                595                 600                 605
Lys Ile Ile Ala Asn Leu Gly Ala Gly Asn Asp Asn Val Phe Val Gly
                610                 615                 620
Ser Ser Thr Thr Val Ile Asp Gly Gly Asp Gly His Asp Arg Val His
625                 630                 635                 640
Tyr Ser Arg Gly Glu Tyr Gly Ala Leu Val Ile Asp Ala Thr Ala Glu
                645                 650                 655
Thr Glu Lys Gly Ser Tyr Ser Val Lys Arg Tyr Val Gly Asp Ser Lys
                660                 665                 670
Ala Leu His Glu Thr Ile Ala Thr His Gln Thr Asn Val Gly Asn Arg
                675                 680                 685
Glu Glu Lys Ile Glu Tyr Arg Arg Glu Asp Asp Arg Phe His Thr Gly
                690                 695                 700
Tyr Thr Val Thr Asp Ser Leu Lys Ser Val Glu Glu Ile Ile Gly Ser
705                 710                 715                 720
```

-continued

```
Gln Phe Asn Asp Ile Phe Lys Gly Ser Gln Phe Asp Val Phe His
                725                 730                 735
Gly Gly Asn Gly Val Asp Thr Ile Asp Gly Asn Asp Gly Asp Asp His
            740                 745                 750
Leu Phe Gly Gly Ala Gly Asp Val Ile Asp Gly Gly Asn Gly Asn
        755                 760                 765
Asn Phe Leu Val Gly Gly Thr Gly Asn Asp Ile Ile Ser Gly Gly Lys
    770                 775                 780
Asp Asn Asp Ile Tyr Val His Lys Thr Gly Asp Gly Asn Asp Ser Ile
785                 790                 795                 800
Thr Asp Ser Gly Gly Gln Asp Lys Leu Ala Phe Ser Asp Val Asn Leu
                805                 810                 815
Lys Asp Leu Thr Phe Lys Lys Val Asp Ser Ser Leu Glu Ile Ile Asn
            820                 825                 830
Gln Lys Gly Glu Lys Val Arg Ile Gly Asn Trp Phe Leu Glu Asp Asp
        835                 840                 845
Leu Ala Ser Thr Val Ala Asn Tyr Lys Ala Thr Asn Asp Arg Lys Ile
    850                 855                 860
Glu Glu Ile Ile Gly Lys Gly Gly Glu Arg Ile Thr Ser Glu Gln Val
865                 870                 875                 880
Asp Lys Leu Ile Lys Glu Gly Asn Asn Gln Ile Ser Ala Glu Ala Leu
                885                 890                 895
Ser Lys Val Val Asn Asp Tyr Asn Thr Ser Lys Asp Arg Gln Asn Val
            900                 905                 910
Ser Asn Ser Leu Ala Lys Leu Ile Ser Ser Val Gly Ser Phe Thr Ser
        915                 920                 925
Ser Ser Asp Phe Arg Asn Asn Leu Gly Thr Tyr Val Pro Ser Ser Ile
    930                 935                 940
Asp Val Ser Asn Asn Ile Gln Leu Ala Arg Ala Ala
945                 950                 955

<210> SEQ ID NO 5
<211> LENGTH: 1023
<212> TYPE: PRT
<213> ORGANISM: Escherichia coli

<400> SEQUENCE: 5

Met Pro Thr Ile Thr Ala Ala Gln Ile Lys Ser Thr Leu Gln Ser Ala
  1               5                  10                  15
Lys Gln Ser Ala Ala Asn Lys Leu His Ser Ala Gly Gln Ser Thr Lys
                20                  25                  30
Asp Ala Leu Lys Lys Ala Glu Gln Thr Arg Asn Ala Gly Asn Arg
            35                  40                  45
Leu Ile Leu Leu Ile Pro Lys Asp Tyr Lys Gly Gln Gly Ser Ser Leu
        50                  55                  60
Asn Asp Leu Val Arg Thr Ala Asp Glu Leu Gly Ile Glu Val Gln Tyr
 65                  70                  75                  80
Asp Glu Lys Asn Gly Thr Ala Ile Thr Lys Gln Val Phe Gly Thr Ala
                85                  90                  95
Glu Lys Leu Ile Gly Leu Thr Glu Arg Gly Val Thr Ile Phe Ala Pro
            100                 105                 110
Gln Leu Asp Lys Leu Leu Gln Lys Tyr Gln Lys Ala Gly Asn Lys Leu
        115                 120                 125
Gly Gly Ser Ala Glu Asn Ile Gly Asp Asn Leu Gly Lys Ala Gly Ser
```

-continued

```
            130                 135                 140
Val Leu Ser Thr Phe Gln Asn Phe Leu Gly Thr Ala Leu Ser Ser Met
145                 150                 155                 160

Lys Ile Asp Glu Leu Ile Lys Lys Gln Lys Ser Gly Gly Asn Val Ser
                165                 170                 175

Ser Ser Glu Leu Ala Lys Ala Ser Ile Glu Leu Ile Asn Gln Leu Val
                180                 185                 190

Asp Thr Ala Ala Ser Leu Asn Asn Val Asn Ser Phe Ser Gln Gln Leu
                195                 200                 205

Asn Lys Leu Gly Ser Val Leu Ser Asn Thr Lys His Leu Asn Gly Val
210                 215                 220

Gly Asn Lys Leu Gln Asn Leu Pro Asn Leu Asp Asn Ile Gly Ala Gly
225                 230                 235                 240

Leu Asp Thr Val Ser Gly Ile Leu Ser Ala Ile Ser Ala Ser Phe Ile
                245                 250                 255

Leu Ser Asn Ala Asp Ala Asp Thr Gly Thr Lys Ala Ala Ala Gly Val
                260                 265                 270

Glu Leu Thr Thr Lys Val Leu Gly Asn Val Gly Lys Gly Ile Ser Gln
                275                 280                 285

Tyr Ile Ile Ala Gln Arg Ala Ala Gln Gly Leu Ser Thr Ser Ala Ala
                290                 295                 300

Ala Ala Gly Leu Ile Ala Ser Val Val Thr Leu Ala Ile Ser Pro Leu
305                 310                 315                 320

Ser Phe Leu Ser Ile Ala Asp Lys Phe Lys Arg Ala Asn Lys Ile Glu
                325                 330                 335

Glu Tyr Ser Gln Arg Phe Lys Lys Leu Gly Tyr Asp Gly Asp Ser Leu
                340                 345                 350

Leu Ala Ala Phe His Lys Glu Thr Gly Ala Ile Asp Ala Ser Leu Thr
                355                 360                 365

Arg Ile Ser Thr Val Leu Ala Ser Val Ser Ser Gly Ile Ser Ala Ala
                370                 375                 380

Ala Thr Thr Ser Leu Val Gly Ala Pro Val Ser Ala Leu Val Gly Ala
385                 390                 395                 400

Val Thr Gly Ile Ile Ser Gly Ile Leu Glu Ala Ser Lys Gln Ala Met
                405                 410                 415

Phe Glu His Val Ala Ser Lys Met Ala Asp Val Ile Ala Glu Trp Glu
                420                 425                 430

Lys Lys His Gly Lys Asn Tyr Phe Glu Asn Gly Tyr Asp Ala Arg His
                435                 440                 445

Ala Ala Phe Leu Glu Asp Asn Phe Lys Ile Leu Ser Gln Tyr Asn Lys
450                 455                 460

Glu Tyr Ser Val Glu Arg Ser Val Leu Ile Thr Gln Gln His Trp Asp
465                 470                 475                 480

Thr Leu Ile Gly Glu Leu Ala Gly Val Thr Arg Asn Gly Asp Lys Thr
                485                 490                 495

Leu Ser Gly Lys Ser Tyr Ile Asp Tyr Tyr Glu Glu Gly Lys Arg Leu
                500                 505                 510

Glu Lys Lys Pro Asp Glu Phe Gln Lys Gln Val Phe Asp Pro Leu Lys
                515                 520                 525

Gly Asn Ile Asp Leu Ser Asp Ser Lys Ser Ser Thr Leu Leu Lys Phe
530                 535                 540

Val Thr Pro Leu Leu Thr Pro Gly Glu Glu Ile Arg Glu Arg Arg Gln
545                 550                 555                 560
```

-continued

Ser Gly Lys Tyr Glu Tyr Ile Thr Glu Leu Leu Val Lys Gly Val Asp
                565                 570                 575

Lys Trp Thr Val Lys Gly Val Gln Asp Lys Gly Ser Val Tyr Asp Tyr
            580                 585                 590

Ser Asn Leu Ile Gln His Ala Ser Val Gly Asn Asn Gln Tyr Arg Glu
            595                 600                 605

Ile Arg Ile Glu Ser His Leu Gly Asp Gly Asp Lys Val Phe Leu
        610                 615                 620

Ser Ala Gly Ser Ala Asn Ile Tyr Ala Gly Lys Gly His Asp Val Val
625                 630                 635                 640

Tyr Tyr Asp Lys Thr Asp Thr Gly Tyr Leu Thr Ile Asp Gly Thr Lys
            645                 650                 655

Ala Thr Glu Ala Gly Asn Tyr Thr Val Thr Arg Val Leu Gly Gly Asp
            660                 665                 670

Val Lys Val Leu Gln Glu Val Val Lys Glu Gln Glu Val Ser Val Gly
            675                 680                 685

Lys Arg Thr Glu Lys Thr Gln Tyr Arg Ser Tyr Glu Phe Thr His Ile
        690                 695                 700

Asn Gly Lys Asn Leu Thr Glu Thr Asp Asn Leu Tyr Ser Val Glu Glu
705                 710                 715                 720

Leu Ile Gly Thr Thr Arg Ala Asp Lys Phe Phe Gly Ser Lys Phe Ala
                725                 730                 735

Asp Ile Phe His Gly Ala Asp Gly Asp His Ile Glu Gly Asn Asp
            740                 745                 750

Gly Asn Asp Arg Leu Tyr Gly Asp Lys Gly Asn Asp Thr Leu Ser Gly
        755                 760                 765

Gly Asn Gly Asp Asp Gln Leu Tyr Gly Gly Asp Gly Asn Asp Lys Leu
        770                 775                 780

Ile Gly Gly Ala Gly Asn Asn Tyr Leu Asn Gly Gly Asp Gly Asp Asp
785                 790                 795                 800

Glu Leu Gln Val Gln Gly Asn Ser Leu Ala Lys Asn Val Leu Ser Gly
                805                 810                 815

Gly Lys Gly Asn Asp Lys Leu Tyr Gly Ser Glu Gly Ala Asp Leu Leu
            820                 825                 830

Asp Gly Gly Glu Gly Asn Asp Leu Leu Lys Gly Gly Tyr Gly Asn Asp
            835                 840                 845

Ile Tyr Arg Tyr Leu Ser Gly Tyr Gly His His Ile Ile Asp Asp Asp
        850                 855                 860

Gly Gly Lys Asp Asp Lys Leu Ser Leu Ala Asp Ile Asp Phe Arg Asp
865                 870                 875                 880

Val Ala Phe Arg Arg Glu Gly Asn Asp Leu Ile Met Tyr Lys Ala Glu
                885                 890                 895

Gly Asn Val Leu Ser Ile His Lys Asn Gly Ile Thr Phe Lys Asn
            900                 905                 910

Trp Phe Glu Lys Glu Ser Gly Asp Ile Ser Asn His Gln Ile Glu Gln
        915                 920                 925

Ile Phe Asp Lys Asp Gly Arg Val Ile Thr Pro Asp Ser Leu Lys Lys
        930                 935                 940

Ala Leu Glu Tyr Gln Gln Ser Asn Asn Lys Ala Ser Tyr Val Tyr Gly
945                 950                 955                 960

Asn Asp Ala Leu Ala Tyr Gly Ser Gln Gly Asn Leu Asn Pro Leu Ile
                965                 970                 975

```
Asn Glu Ile Ser Lys Ile Ile Ser Ala Ala Gly Asn Phe Asp Val Lys
            980                 985                 990
Glu Glu Arg Ala Ala Ala Ser Leu Leu Gln Leu Ser Gly Asn Ala Ser
        995                1000                1005
Asp Phe Ser Tyr Gly Arg Asn Ser Ile Thr Leu Thr Ala Ser Ala
    1010                1015                1020

<210> SEQ ID NO 6
<211> LENGTH: 12
<212> TYPE: PRT
<213> ORGANISM: Moraxella bovis

<400> SEQUENCE: 6

Phe Leu Ser Glu Leu Asn Lys Glu Leu Glu Ala Glu
1               5                   10

<210> SEQ ID NO 7
<211> LENGTH: 12
<212> TYPE: PRT
<213> ORGANISM: Pasteurella haemolytica

<400> SEQUENCE: 7

Phe Leu Leu Asn Leu Asn Lys Glu Leu Gln Ala Glu
1               5                   10

<210> SEQ ID NO 8
<211> LENGTH: 12
<212> TYPE: PRT
<213> ORGANISM: Escherichia coli

<400> SEQUENCE: 8

Ile Leu Ser Gln Tyr Asn Lys Glu Tyr Ser Val Glu
1               5                   10

<210> SEQ ID NO 9
<211> LENGTH: 12
<212> TYPE: PRT
<213> ORGANISM: Actinobacillus pleuropneumoniae

<400> SEQUENCE: 9

Phe Leu Ile Asn Leu Asn Lys Glu Leu Gln Ala Glu
1               5                   10

<210> SEQ ID NO 10
<211> LENGTH: 12
<212> TYPE: PRT
<213> ORGANISM: Actinobacillus pleuropneumoniae

<400> SEQUENCE: 10

Leu Leu Ser Gln Tyr Asn Lys Glu Tyr Ser Val Glu
1               5                   10

<210> SEQ ID NO 11
<211> LENGTH: 12
<212> TYPE: PRT
<213> ORGANISM: Actinobacillus suis

<400> SEQUENCE: 11

Phe Leu Ile Asn Leu Asn Lys Glu Leu Gln Ala Glu
1               5                   10

<210> SEQ ID NO 12
<211> LENGTH: 9
<212> TYPE: PRT
```

```
<213> ORGANISM: Artificial Sequence
<220> FEATURE:
<223> OTHER INFORMATION: Description of Artificial Sequence: consensus
      sequence
<221> NAME/KEY: MOD_RES
<222> LOCATION: (3)
<223> OTHER INFORMATION: L, Y, A or V
<221> NAME/KEY: MOD_RES
<222> LOCATION: (7)..(8)
<223> OTHER INFORMATION: L, Y, A or V

<400> SEQUENCE: 12

Phe Leu Xaa Asn Lys Glu Xaa Xaa Glu
 1               5

<210> SEQ ID NO 13
<211> LENGTH: 14
<212> TYPE: PRT
<213> ORGANISM: Moraxella bovis

<400> SEQUENCE: 13

Phe Asn Asp Ile Phe His Ser Gly Glu Gly Asp Asp Leu Leu
 1               5                  10

<210> SEQ ID NO 14
<211> LENGTH: 14
<212> TYPE: PRT
<213> ORGANISM: Actinobacillus pleuropneumoniae

<400> SEQUENCE: 14

Phe Arg Asp Ile Phe His Gly Ala Asp Gly Asp Asp Leu Leu
 1               5                  10

<210> SEQ ID NO 15
<211> LENGTH: 14
<212> TYPE: PRT
<213> ORGANISM: Actinobacillus  actinomycetemcomitans

<400> SEQUENCE: 15

Phe Asn Asp Val Phe His Gly His Asp Gly Asp Asp Leu Ile
 1               5                  10

<210> SEQ ID NO 16
<211> LENGTH: 14
<212> TYPE: PRT
<213> ORGANISM: Actinobacillus pleuropneumoniae

<400> SEQUENCE: 16

Phe Arg Asp Ile Phe His Gly Ala Asp Gly Asp Leu Leu
 1               5                  10

<210> SEQ ID NO 17
<211> LENGTH: 11
<212> TYPE: PRT
<213> ORGANISM: Artificial Sequence
<220> FEATURE:
<223> OTHER INFORMATION: Description of Artificial Sequence: consensus
      sequence
<221> NAME/KEY: MOD_RES
<222> LOCATION: (11)
<223> OTHER INFORMATION: L or I

<400> SEQUENCE: 17

Phe Asp Phe His Gly Ala Asp Gly Asp Asp Xaa
 1               5                  10

<210> SEQ ID NO 18
```

```
<211> LENGTH: 737
<212> TYPE: PRT
<213> ORGANISM: Moraxella bovis

<400> SEQUENCE: 18
```

| | | | | | | | | | | | | | | |
|---|---|---|---|---|---|---|---|---|---|---|---|---|---|---|
|Met|Gly|Gly|Asp|Thr|Ser|Leu|Ile|Arg|Leu|Asn|Leu|Gln|Thr|Leu|Asn|
|1| | | |5| | | | |10| | | | |15| |

Ser Asn Leu Val Met Ile Asp Tyr Ala Gln Gln Pro Ala Leu Ser Ala
            20                  25                  30

Leu Val Ile Leu Ala Lys Tyr Tyr Gly Ile Ser Ala Ser Pro Ala Asp
        35                  40                  45

Ile Met His Gln Phe Ser Asp Asn Thr Lys Gly Asp Leu Asn Glu Ile
    50                  55                  60

Glu Trp Met Leu Ala Ala Lys Lys Leu Glu Leu Lys Val Lys Ile Ile
65                  70                  75                  80

Lys Gln Pro Leu Thr Arg Leu Ser Met Ile Thr Leu Pro Ala Leu Val
                85                  90                  95

Trp Cys Asp Asn Lys Pro Asp Leu Asp Gln Asn Leu Asn Ser His Phe
            100                 105                 110

Ile Leu Thr Lys Ile Asp Gly Val Gly Ser Ala Ala Lys Tyr Leu Ile
        115                 120                 125

Tyr Asp Leu Ile Glu Asn Arg Pro Ile Ile Leu Asp Ala Ser Glu Phe
    130                 135                 140

Ser Glu Arg Tyr Ser Gly Lys Leu Met Leu Val Thr Ser Arg Ala Ser
145                 150                 155                 160

Ile Leu Gly Ser Leu Ala Lys Phe Asp Phe Thr Trp Phe Ile Pro Ala
                165                 170                 175

Val Ile Lys Tyr Arg Tyr Ile Phe Phe Glu Val Ile Val Ile Ser Val
            180                 185                 190

Val Leu Gln Ile Phe Ala Leu Ile Thr Pro Leu Phe Phe Gln Val Val
        195                 200                 205

Met Asp Lys Val Leu Val His Arg Gly Phe Ser Thr Leu Asp Val Val
    210                 215                 220

Ala Ile Ala Leu Leu Val Val Ser Leu Phe Glu Val Ile Leu Ser Gly
225                 230                 235                 240

Leu Arg Thr Tyr Ile Phe Ala His Thr Thr Ser Arg Ile Asp Val Glu
                245                 250                 255

Leu Gly Ala Arg Leu Phe Arg His Leu Leu Ala Leu Pro Leu Ala Tyr
            260                 265                 270

Phe Glu Ser Arg Arg Val Gly Asp Thr Val Ala Arg Ile Arg Glu Leu
        275                 280                 285

Glu His Ile Arg Asn Phe Leu Thr Gly Gln Ala Leu Thr Ser Val Leu
    290                 295                 300

Asp Leu Val Phe Ser Phe Ile Phe Leu Phe Val Met Trp Tyr Tyr Ser
305                 310                 315                 320

Pro Thr Leu Thr Leu Val Val Leu Ala Ser Leu Pro Ile Tyr Ala Phe
                325                 330                 335

Trp Ser Ala Phe Ile Ser Pro Ile Leu Arg Thr Arg Leu Asn Asp Gln
            340                 345                 350

Phe Ala Arg Asn Ala Asp Asn Gln Ser Phe Leu Val Glu Ser Ile Thr
        355                 360                 365

Ala Val Gly Thr Val Lys Ala Met Ala Val Glu Pro Gln Met Thr Arg
    370                 375                 380

Arg Trp Asp Asn Gln Leu Ala Ala Tyr Val Val Ser Ser Phe Arg Val

-continued

```
                385                 390                 395                 400
Ala Lys Leu Ala Met Val Gly Gln Gln Gly Val Gln Leu Ile Gln Lys
                    405                 410                 415
Met Val Ile Val Ala Thr Leu Trp Ile Gly Ala Lys Leu Val Ile Glu
                    420                 425                 430
Gly Lys Leu Ser Val Gly Gln Leu Ile Ala Phe Asn Met Leu Ala Gly
                    435                 440                 445
Gln Val Ala Ala Pro Val Ile Arg Leu Ala Gln Leu Trp Gln Asp Phe
                    450                 455                 460
Gln Gln Val Gly Ile Ser Val Ala Arg Leu Gly Asp Ile Leu Asn Thr
465                 470                 475                 480
Pro Thr Glu His Ser Thr Ser Arg Leu Thr Leu Pro Asp Ile Lys Gly
                    485                 490                 495
Asp Ile Thr Phe Glu Asn Val Asp Phe Arg Tyr Lys Ile Asp Gly His
                    500                 505                 510
Leu Ile Leu Gln Asn Leu Asn Leu Gln Ile Asn Ala Gly Glu Ile Leu
                    515                 520                 525
Gly Ile Val Gly Arg Ser Gly Ser Gly Lys Ser Thr Leu Thr Lys Leu
                    530                 535                 540
Val Gln Arg Leu Tyr Val Pro Glu Asn Gly Arg Ile Leu Val Asp Gly
545                 550                 555                 560
Asn Asp Leu Ala Leu Ala Asp Pro Ala Trp Leu Arg Arg Gln Val Gly
                    565                 570                 575
Val Val Leu Gln Glu Asn Val Leu Leu Asn Arg Ser Ile Arg Asp Asn
                    580                 585                 590
Ile Ala Leu Thr Asp Thr Gly Met Ser Leu Glu Phe Ile Ile Gln Ala
                    595                 600                 605
Ala Lys Met Ser Gly Ala His Asp Phe Ile Met Glu Leu Pro Glu Gly
                    610                 615                 620
Tyr Asp Thr Ile Val Gly Glu Gln Gly Ala Gly Leu Ser Gly Gly Gln
625                 630                 635                 640
Arg Gln Arg Ile Ala Ile Ala Arg Ala Leu Ile Thr Asn Pro Arg Ile
                    645                 650                 655
Leu Ile Phe Asp Glu Ala Thr Ser Ala Leu Asp Tyr Glu Ser Glu Arg
                    660                 665                 670
Ala Ile Met Gln Asn Met Gln Ala Ile Cys Gln Gly Arg Thr Val Leu
                    675                 680                 685
Ile Ile Ala His Arg Leu Ser Thr Val Lys Met Ala His Arg Ile Ile
                    690                 695                 700
Ala Met Asp Lys Gly Lys Ile Val Glu Gln Gly Thr His Gln Glu Leu
705                 710                 715                 720
Leu Gln Lys Glu Asp Gly Tyr Tyr Arg Tyr Leu Tyr Asp Leu Gln Asn
                    725                 730                 735
Gly
```

<210> SEQ ID NO 19
<211> LENGTH: 708
<212> TYPE: PRT
<213> ORGANISM: Pasteurella haemolytica

<400> SEQUENCE: 19

```
Met Glu Ala Asn His Gln Arg Asn Asp Leu Gly Leu Val Ala Leu Thr
1               5                   10                  15
Met Leu Ala Gln Tyr His Asn Ile Ser Leu Asn Pro Glu Glu Ile Lys
```

-continued

```
                     20                  25                  30
His Lys Phe Asp Leu Asp Gly Lys Gly Leu Ser Leu Thr Ala Trp Leu
                 35                  40                  45

Leu Ala Ala Lys Ser Leu Ala Leu Lys Ala Lys His Ile Lys Lys Glu
 50                  55                  60

Ile Ser Arg Leu His Leu Val Asn Leu Pro Ala Leu Val Trp Gln Asp
 65                  70                  75                  80

Asn Gly Lys His Phe Leu Leu Val Lys Val Asp Thr Asp Asn Asn Arg
                 85                  90                  95

Tyr Leu Thr Tyr Asn Leu Glu Gln Asp Ala Pro Gln Ile Leu Ser Thr
                100                 105                 110

Asp Glu Phe Glu Ala Cys Tyr Gln Gly Gln Leu Ile Leu Val Thr Ser
                115                 120                 125

Arg Ala Ser Val Val Gly Gln Leu Ala Lys Phe Asp Phe Thr Trp Phe
                130                 135                 140

Ile Pro Ala Val Ile Lys Tyr Arg Lys Ile Phe Leu Glu Thr Leu Ile
145                 150                 155                 160

Val Ser Ile Phe Leu Gln Ile Phe Ala Leu Ile Thr Pro Leu Phe Phe
                165                 170                 175

Gln Val Val Met Asp Lys Val Leu Val His Arg Gly Phe Ser Thr Leu
                180                 185                 190

Asn Ile Ile Thr Val Ala Leu Ala Ile Val Ile Phe Glu Ile Val
                195                 200                 205

Leu Ser Gly Leu Arg Thr Tyr Val Phe Ser His Ser Thr Ser Arg Ile
                210                 215                 220

Asp Val Glu Leu Gly Ala Lys Leu Phe Arg His Leu Leu Ser Leu Pro
225                 230                 235                 240

Ile Ser Tyr Phe Glu Asn Arg Arg Val Gly Asp Thr Val Ala Arg Val
                245                 250                 255

Arg Glu Leu Asp Gln Ile Arg Asn Phe Leu Thr Gly Gln Ala Leu Thr
                260                 265                 270

Ser Val Leu Asp Leu Leu Phe Ser Phe Ile Phe Phe Ala Val Met Trp
                275                 280                 285

Tyr Tyr Ser Pro Lys Leu Thr Leu Val Ile Leu Gly Ser Leu Pro Cys
290                 295                 300

Tyr Ile Leu Trp Ser Ile Phe Ile Ser Pro Ile Leu Arg Arg Arg Leu
305                 310                 315                 320

Asp Glu Lys Phe Ala Arg Ser Ala Asp Asn Gln Ala Phe Leu Val Glu
                325                 330                 335

Ser Val Thr Ala Ile Asn Met Ile Lys Ala Met Ala Val Ala Pro Gln
                340                 345                 350

Met Thr Asp Thr Trp Asp Lys Gln Leu Ala Ser Tyr Val Ser Ser Ser
                355                 360                 365

Phe Arg Val Thr Val Leu Ala Thr Ile Gly Gln Gln Gly Val Gln Leu
                370                 375                 380

Ile Gln Lys Thr Val Met Val Ile Asn Leu Trp Leu Gly Ala His Leu
385                 390                 395                 400

Val Ile Ser Gly Asp Leu Ser Ile Gly Gln Leu Ile Ala Phe Asn Met
                405                 410                 415

Leu Ser Gly Gln Val Ile Ala Pro Val Ile Arg Leu Ala Gln Leu Trp
                420                 425                 430

Gln Asp Phe Gln Gln Val Gly Ile Ser Val Thr Arg Leu Gly Asp Val
                435                 440                 445
```

-continued

```
Leu Asn Ser Pro Thr Glu Gln Tyr Gln Gly Lys Leu Ser Leu Pro Glu
    450                 455                 460

Ile Lys Gly Asp Ile Ser Phe Lys Asn Ile Arg Phe Arg Tyr Lys Pro
465                 470                 475                 480

Asp Ala Pro Thr Ile Leu Asn Asn Val Asn Leu Glu Ile Arg Gln Gly
                485                 490                 495

Glu Val Ile Gly Ile Val Gly Arg Ser Gly Ser Gly Lys Ser Thr Leu
            500                 505                 510

Thr Lys Leu Leu Gln Arg Phe Tyr Ile Pro Glu Asn Gly Gln Val Leu
        515                 520                 525

Ile Asp Gly His Asp Leu Ala Leu Ala Asp Pro Asn Trp Leu Arg Arg
    530                 535                 540

Gln Ile Gly Val Val Leu Gln Asp Asn Val Leu Leu Asn Arg Ser Ile
545                 550                 555                 560

Arg Glu Asn Ile Ala Leu Ser Asp Pro Gly Met Pro Met Glu Arg Val
                565                 570                 575

Ile Tyr Ala Ala Lys Leu Ala Gly Ala His Asp Phe Ile Ser Glu Leu
            580                 585                 590

Arg Glu Gly Tyr Asn Thr Ile Val Gly Glu Gln Gly Ala Gly Leu Ser
        595                 600                 605

Gly Gly Gln Arg Gln Arg Ile Ala Ile Ala Arg Ala Leu Val Asn Asn
    610                 615                 620

Pro Lys Ile Leu Ile Phe Asp Glu Ala Thr Ser Ala Leu Asp Tyr Glu
625                 630                 635                 640

Ser Glu His Ile Ile Met Gln Asn Met Gln Lys Ile Cys Gln Gly Arg
                645                 650                 655

Thr Val Ile Leu Ile Ala His Arg Leu Ser Thr Val Lys Asn Ala Asp
            660                 665                 670

Arg Ile Ile Val Met Glu Lys Gly Glu Ile Val Glu Gln Gly Lys His
        675                 680                 685

His Glu Leu Leu Gln Asn Ser Asn Gly Leu Tyr Ser Tyr Leu His Gln
    690                 695                 700

Leu Gln Leu Asn
705

<210> SEQ ID NO 20
<211> LENGTH: 707
<212> TYPE: PRT
<213> ORGANISM: Actinobacillus pleuropneumoniae

<400> SEQUENCE: 20

Met Asp Phe Tyr Arg Glu Glu Asp Tyr Gly Leu Tyr Ala Leu Thr Ile
1               5                   10                  15

Leu Ala Gln Tyr His Asn Ile Ala Val Asn Pro Glu Glu Leu Lys His
            20                  25                  30

Lys Phe Asp Leu Glu Gly Lys Gly Leu Asp Leu Thr Ala Trp Leu Leu
        35                  40                  45

Ala Ala Lys Ser Leu Glu Leu Lys Ala Lys Gln Val Lys Lys Ala Ile
    50                  55                  60

Asp Arg Leu Ala Phe Ile Ala Leu Pro Ala Leu Val Trp Arg Glu Asp
65                  70                  75                  80

Gly Lys His Phe Ile Leu Thr Lys Ile Asp Asn Glu Ala Lys Lys Tyr
                85                  90                  95

Leu Ile Phe Asp Leu Glu Thr His Asn Pro Arg Ile Leu Glu Gln Ala
```

-continued

```
                100                 105                 110
Glu Phe Glu Ser Leu Tyr Gln Gly Lys Leu Ile Leu Val Ala Ser Arg
            115                 120                 125
Ala Ser Ile Val Gly Lys Leu Ala Lys Phe Asp Phe Thr Trp Phe Ile
            130                 135                 140
Pro Ala Val Ile Lys Tyr Arg Lys Ile Phe Ile Glu Thr Leu Ile Val
145                 150                 155                 160
Ser Ile Phe Leu Gln Ile Phe Ala Leu Ile Thr Pro Leu Phe Phe Gln
                165                 170                 175
Val Val Met Asp Lys Val Leu Val His Arg Gly Phe Ser Thr Leu Asn
            180                 185                 190
Val Ile Thr Val Ala Leu Ala Ile Val Val Leu Phe Glu Ile Val Leu
            195                 200                 205
Asn Gly Leu Arg Thr Tyr Ile Phe Ala His Ser Thr Ser Arg Ile Asp
        210                 215                 220
Val Glu Leu Gly Ala Arg Leu Phe Arg His Leu Leu Ala Leu Pro Ile
225                 230                 235                 240
Ser Tyr Phe Glu Asn Arg Arg Val Gly Asp Thr Val Ala Arg Val Arg
                245                 250                 255
Glu Leu Asp Gln Ile Arg Asn Phe Leu Thr Gly Gln Ala Leu Thr Ser
            260                 265                 270
Val Leu Asp Leu Met Phe Ser Phe Ile Phe Ala Val Met Trp Tyr
        275                 280                 285
Tyr Ser Pro Lys Leu Thr Leu Val Ile Leu Gly Ser Leu Pro Phe Tyr
        290                 295                 300
Met Gly Trp Ser Ile Phe Ile Ser Pro Ile Leu Arg Arg Leu Asp
305                 310                 315                 320
Glu Lys Phe Ala Arg Gly Ala Asp Asn Gln Ser Phe Leu Val Glu Ser
                325                 330                 335
Val Thr Ala Ile Asn Thr Ile Lys Ala Leu Ala Val Thr Pro Gln Met
            340                 345                 350
Thr Asn Thr Trp Asp Lys Gln Leu Ala Ser Tyr Val Ser Ala Gly Phe
            355                 360                 365
Arg Val Thr Thr Leu Ala Thr Ile Gly Gln Gln Gly Val Gln Phe Ile
        370                 375                 380
Gln Lys Val Val Met Val Ile Thr Leu Trp Leu Gly Ala His Leu Val
385                 390                 395                 400
Ile Ser Gly Asp Leu Ser Ile Gly Gln Leu Ile Ala Phe Asn Met Leu
                405                 410                 415
Ser Gly Gln Val Ile Ala Pro Val Ile Arg Leu Ala Gln Leu Trp Gln
            420                 425                 430
Asp Phe Gln Gln Val Gly Ile Ser Val Thr Arg Leu Gly Asp Val Leu
            435                 440                 445
Asn Ser Pro Thr Glu Ser Tyr Gln Gly Lys Leu Ala Leu Pro Glu Ile
        450                 455                 460
Lys Gly Asp Ile Thr Phe Arg Asn Ile Arg Phe Arg Tyr Lys Pro Asp
465                 470                 475                 480
Ala Pro Val Ile Leu Asn Asp Val Asn Leu Ser Ile Gln Gln Gly Glu
                485                 490                 495
Val Ile Gly Ile Val Gly Arg Ser Gly Ser Gly Lys Ser Thr Leu Thr
            500                 505                 510
Lys Leu Ile Gln Arg Phe Tyr Ile Pro Glu Asn Gly Gln Val Leu Ile
        515                 520                 525
```

```
Asp Gly His Asp Leu Ala Leu Ala Asp Pro Asn Trp Leu Arg Arg Gln
        530                 535                 540

Val Gly Val Val Leu Gln Asp Asn Val Leu Leu Asn Arg Ser Ile Arg
545                 550                 555                 560

Asp Asn Ile Ala Leu Ala Asp Pro Gly Met Pro Met Glu Lys Ile Val
                565                 570                 575

His Ala Ala Lys Leu Ala Gly Ala His Glu Phe Ile Ser Glu Leu Arg
            580                 585                 590

Glu Gly Tyr Asn Thr Ile Val Gly Glu Gln Gly Ala Gly Leu Ser Gly
        595                 600                 605

Gly Gln Arg Gln Arg Ile Ala Ile Ala Arg Ala Leu Val Asn Asn Pro
    610                 615                 620

Lys Ile Leu Ile Phe Asp Glu Ala Thr Ser Ala Leu Asp Tyr Glu Ser
625                 630                 635                 640

Glu His Ile Ile Met Arg Asn Met His Gln Ile Cys Lys Gly Arg Thr
                645                 650                 655

Val Ile Ile Ile Ala His Arg Leu Ser Thr Val Lys Asn Ala Asp Arg
            660                 665                 670

Ile Ile Val Met Glu Lys Gly Gln Ile Val Glu Gln Gly Lys His Lys
        675                 680                 685

Glu Leu Leu Ala Asp Pro Asn Gly Leu Tyr His Tyr Leu His Gln Leu
    690                 695                 700

Gln Ser Glu
705

<210> SEQ ID NO 21
<211> LENGTH: 707
<212> TYPE: PRT
<213> ORGANISM: Escherichia coli

<400> SEQUENCE: 21

Met Asp Ser Cys His Lys Ile Asp Tyr Gly Leu Tyr Ala Leu Glu Ile
  1               5                  10                  15

Leu Ala Gln Tyr His Asn Val Ser Val Asn Pro Glu Glu Ile Lys His
            20                  25                  30

Arg Phe Asp Thr Asp Gly Thr Gly Leu Gly Leu Thr Ser Trp Leu Leu
        35                  40                  45

Ala Ala Lys Ser Leu Glu Leu Lys Val Lys Gln Val Lys Lys Thr Ile
    50                  55                  60

Asp Arg Leu Asn Phe Ile Ser Leu Pro Ala Leu Val Trp Arg Glu Asp
65                  70                  75                  80

Gly Arg His Phe Ile Leu Thr Lys Val Ser Lys Glu Ala Asn Arg Tyr
                85                  90                  95

Leu Ile Phe Asp Leu Glu Gln Arg Asn Pro Arg Val Leu Glu Gln Ser
            100                 105                 110

Glu Phe Glu Ala Leu Tyr Gln Gly His Ile Ile Leu Ile Ala Ser Arg
        115                 120                 125

Ser Ser Val Ala Gly Lys Leu Ala Lys Phe Asp Phe Thr Trp Phe Ile
    130                 135                 140

Pro Ala Ile Ile Lys Tyr Arg Arg Ile Phe Ile Glu Thr Leu Val Val
145                 150                 155                 160

Ser Val Phe Leu Gln Leu Phe Ala Leu Ile Thr Pro Leu Phe Phe Gln
                165                 170                 175

Val Val Met Asp Lys Val Leu Val His Arg Gly Phe Ser Thr Leu Asn
```

```
                180                 185                 190
Val Ile Thr Val Ala Leu Ser Val Val Val Phe Glu Ile Ile Leu
            195                 200                 205

Ser Gly Leu Arg Thr Tyr Ile Phe Ala His Ser Thr Ser Arg Ile Asp
210                 215                 220

Val Glu Leu Gly Ala Lys Leu Phe Arg His Leu Leu Ala Leu Pro Ile
225                 230                 235                 240

Ser Tyr Phe Glu Ser Arg Arg Val Gly Asp Thr Val Ala Arg Val Arg
                245                 250                 255

Glu Leu Asp Gln Ile Arg Asn Phe Leu Thr Gly Gln Ala Leu Thr Ser
            260                 265                 270

Val Leu Asp Leu Leu Phe Ser Phe Ile Phe Phe Ala Val Met Trp Tyr
            275                 280                 285

Tyr Ser Pro Lys Leu Thr Leu Val Ile Leu Phe Ser Leu Pro Cys Tyr
            290                 295                 300

Ala Ala Trp Ser Val Phe Ile Ser Pro Ile Leu Arg Arg Arg Leu Asp
305                 310                 315                 320

Asp Lys Phe Ser Arg Asn Ala Asp Asn Gln Ser Phe Leu Val Glu Ser
                325                 330                 335

Val Thr Ala Ile Asn Thr Ile Lys Ala Met Ala Val Ser Pro Gln Met
            340                 345                 350

Thr Asn Ile Trp Asp Lys Gln Leu Ala Gly Tyr Val Ala Ala Gly Phe
            355                 360                 365

Lys Val Thr Val Leu Ala Thr Ile Gly Gln Gln Gly Ile Gln Leu Ile
            370                 375                 380

Gln Lys Thr Val Met Ile Ile Asn Leu Trp Leu Gly Ala His Leu Val
385                 390                 395                 400

Ile Ser Gly Asp Leu Ser Ile Gly Gln Leu Ile Ala Phe Asn Met Leu
                405                 410                 415

Ala Gly Gln Ile Val Ala Pro Val Ile Arg Leu Ala Gln Ile Trp Gln
            420                 425                 430

Asp Phe Gln Gln Val Gly Ile Ser Val Thr Arg Leu Gly Asp Val Leu
            435                 440                 445

Asn Ser Pro Thr Glu Ser Tyr His Gly Lys Leu Ala Leu Pro Glu Ile
450                 455                 460

Asn Gly Asp Ile Thr Phe Arg Asn Ile Arg Phe Arg Tyr Lys Pro Asp
465                 470                 475                 480

Ser Pro Val Ile Leu Asp Asn Ile Asn Leu Ser Ile Lys Gln Gly Glu
                485                 490                 495

Val Ile Gly Ile Val Gly Arg Ser Gly Ser Gly Lys Ser Thr Leu Thr
            500                 505                 510

Lys Leu Ile Gln Arg Phe Tyr Ile Pro Glu Asn Gly Gln Val Leu Ile
            515                 520                 525

Asp Gly His Asp Leu Ala Leu Ala Asp Pro Asn Trp Leu Arg Arg Gln
            530                 535                 540

Val Gly Val Val Leu Gln Asp Asn Val Leu Leu Asn Arg Ser Ile Ile
545                 550                 555                 560

Asp Asn Ile Ser Leu Ala Asn Pro Gly Met Ser Val Glu Lys Val Ile
                565                 570                 575

Tyr Ala Ala Lys Leu Ala Gly Ala His Asp Phe Ile Ser Glu Leu Arg
            580                 585                 590

Glu Gly Tyr Asn Thr Ile Val Gly Glu Gln Gly Ala Gly Leu Ser Gly
            595                 600                 605
```

Gly Gln Arg Gln Arg Ile Ala Ile Ala Arg Ala Leu Val Asn Asn Pro
    610                 615                 620

Lys Ile Leu Ile Phe Asp Glu Ala Thr Ser Ala Leu Asp Tyr Glu Ser
625                 630                 635                 640

Glu His Ile Ile Met Arg Asn Met His Lys Ile Cys Lys Gly Arg Thr
                645                 650                 655

Val Ile Ile Ile Ala His Arg Leu Ser Thr Val Lys Asn Ala Asp Arg
            660                 665                 670

Ile Ile Val Met Glu Lys Gly Lys Ile Val Glu Gln Gly Lys His Lys
        675                 680                 685

Glu Leu Leu Ser Glu Pro Glu Ser Leu Tyr Ser Tyr Leu Tyr Gln Leu
    690                 695                 700

Gln Ser Asp
705

<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 22
aatgacgata tctttgttgg tcaaggtaaa                                     30

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Primer
<221> NAME/KEY: modified_base
<222> LOCATION: (18)
<223> OTHER INFORMATION: a, t, c, g, other or unknown

<400> SEQUENCE: 23
aayaaagart trgargcnga r                                              21

<210> SEQ ID NO 24
<211> LENGTH: 32
<212> TYPE: DNA
<213> ORGANISM: Artificial Sequence
<220> FEATURE:
<223> OTHER INFORMATION: Description of Artificial Sequence: Primer
<221> NAME/KEY: modified_base
<222> LOCATION: (6)
<223> OTHER INFORMATION: a, t, c, g, other or unknown

<400> SEQUENCE: 24
ccytcnccrc trtgraadat rtcrttraat tt                                  32

<210> SEQ ID NO 25
<211> LENGTH: 27
<212> TYPE: DNA
<213> ORGANISM: Artificial Sequence
<220> FEATURE:
<223> OTHER INFORMATION: Description of Artificial Sequence: Primer
<221> NAME/KEY: modified_base
<222> LOCATION: (15)
<223> OTHER INFORMATION: a, t, c, g, other or unknown
<221> NAME/KEY: modified_base
<222> LOCATION: (18)
<223> OTHER INFORMATION: a, t, c, g, other or unknown
<221> NAME/KEY: modified_base
<222> LOCATION: (24)

```
<223> OTHER INFORMATION: a, t, c, g, other or unknown

<400> SEQUENCE: 25
athgaytgga thgcnccntt yggngay                                          27

<210> SEQ ID NO 26
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 26
actttatcca tcacracttg raaraa                                           26

<210> SEQ ID NO 27
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 27
gatcatatgt ccaatataaa tgtaattaaa tctaa                                 35

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 28
atcactagtt ccataatcta taaccaatga                                       30

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: consensus
      sequence
<221> NAME/KEY: MOD_RES
<222> LOCATION: (1)..(2)
<223> OTHER INFORMATION: Any amino acid
<221> NAME/KEY: MOD_RES
<222> LOCATION: (5)
<223> OTHER INFORMATION: Any amino acid
<221> NAME/KEY: MOD_RES
<222> LOCATION: (7)
<223> OTHER INFORMATION: N or D
<221> NAME/KEY: MOD_RES
<222> LOCATION: (9)
<223> OTHER INFORMATION: Any amino acid

<400> SEQUENCE: 29

Xaa Xaa Gly Gly Xaa Gly Xaa Asp Xaa
 1               5

<210> SEQ ID NO 30
<211> LENGTH: 2215
<212> TYPE: DNA
<213> ORGANISM: Moraxella bovis
<220> FEATURE:
<221> NAME/KEY: CDS
<222> LOCATION: (1)..(2211)

<400> SEQUENCE: 30
```

-continued

| | |
|---|---|
| atg ggt ggt gat act tct tta att aga ctt aat tta caa acc ctt aat<br>Met Gly Gly Asp Thr Ser Leu Ile Arg Leu Asn Leu Gln Thr Leu Asn<br>1               5                  10                  15 | 48 |
| agt aat tta gtt atg ata gat tat gct caa caa cct gct cta tct gct<br>Ser Asn Leu Val Met Ile Asp Tyr Ala Gln Gln Pro Ala Leu Ser Ala<br>            20                  25                  30 | 96 |
| ctg gtt atc ctt gcc aaa tac tat ggt att tct gca agt cca gca gac<br>Leu Val Ile Leu Ala Lys Tyr Tyr Gly Ile Ser Ala Ser Pro Ala Asp<br>        35                  40                  45 | 144 |
| att atg cat cag ttt tct gat aat aca aaa gga gac ctg aat gaa att<br>Ile Met His Gln Phe Ser Asp Asn Thr Lys Gly Asp Leu Asn Glu Ile<br>    50                  55                  60 | 192 |
| gaa tgg atg ttg gca gca aag aaa tta gaa tta aag gta aag att ata<br>Glu Trp Met Leu Ala Ala Lys Lys Leu Glu Leu Lys Val Lys Ile Ile<br>65                  70                  75                  80 | 240 |
| aaa cag cct tta act cga ttg tca atg ata aca ctt cct gct ttg gtg<br>Lys Gln Pro Leu Thr Arg Leu Ser Met Ile Thr Leu Pro Ala Leu Val<br>                85                  90                  95 | 288 |
| tgg tgt gat aat aag ccc gat tta gat caa aat tta aac tct cat ttt<br>Trp Cys Asp Asn Lys Pro Asp Leu Asp Gln Asn Leu Asn Ser His Phe<br>            100                 105                 110 | 336 |
| ata cta act aaa att gat ggg gtg gga tct gct gca aaa tat ctc atc<br>Ile Leu Thr Lys Ile Asp Gly Val Gly Ser Ala Ala Lys Tyr Leu Ile<br>        115                 120                 125 | 384 |
| tac gat ttg att gag aat cgt ccc ata ata tta gat gca agt gag ttt<br>Tyr Asp Leu Ile Glu Asn Arg Pro Ile Ile Leu Asp Ala Ser Glu Phe<br>    130                 135                 140 | 432 |
| tct gaa aga tat tct ggt aag tta atg cta gta act tcc cgt gcg tca<br>Ser Glu Arg Tyr Ser Gly Lys Leu Met Leu Val Thr Ser Arg Ala Ser<br>145                 150                 155                 160 | 480 |
| ata ttg ggt tca ttg gct aaa ttt gat ttt act tgg ttt att cct gcg<br>Ile Leu Gly Ser Leu Ala Lys Phe Asp Phe Thr Trp Phe Ile Pro Ala<br>                165                 170                 175 | 528 |
| gta atc aaa tat cgt tat att ttt ttt gaa gtc atc gtt att tca gtg<br>Val Ile Lys Tyr Arg Tyr Ile Phe Phe Glu Val Ile Val Ile Ser Val<br>            180                 185                 190 | 576 |
| gtg cta cag att ttt gct ctg att acg cca ttg ttt ttt cag gtt gtg<br>Val Leu Gln Ile Phe Ala Leu Ile Thr Pro Leu Phe Phe Gln Val Val<br>        195                 200                 205 | 624 |
| atg gat aag gta ttg gtg cat cgt ggt ttt tct act ctg gat gtg gta<br>Met Asp Lys Val Leu Val His Arg Gly Phe Ser Thr Leu Asp Val Val<br>    210                 215                 220 | 672 |
| gcg att gcc ttg ttg gta gta agt tta ttt gaa gtc att tta agt ggt<br>Ala Ile Ala Leu Leu Val Val Ser Leu Phe Glu Val Ile Leu Ser Gly<br>225                 230                 235                 240 | 720 |
| cta cgc act tat att ttt gct cat aca acc tct cga att gat gta gag<br>Leu Arg Thr Tyr Ile Phe Ala His Thr Thr Ser Arg Ile Asp Val Glu<br>                245                 250                 255 | 768 |
| cta gga gca cga tta ttt cgt cat cta tta gct cta ccg ctt gct tat<br>Leu Gly Ala Arg Leu Phe Arg His Leu Leu Ala Leu Pro Leu Ala Tyr<br>            260                 265                 270 | 816 |
| ttt gag agt aga aga gta ggc gat aca gtt gca cgt ata cgt gaa ttg<br>Phe Glu Ser Arg Arg Val Gly Asp Thr Val Ala Arg Ile Arg Glu Leu<br>        275                 280                 285 | 864 |
| gaa cat atc cgc aat ttc tta act ggt caa gct ctc act tca gtt tta<br>Glu His Ile Arg Asn Phe Leu Thr Gly Gln Ala Leu Thr Ser Val Leu<br>    290                 295                 300 | 912 |
| gat ttg gtg ttt tct ttt ata ttc ttg ttt gta atg tgg tat tac agc<br>Asp Leu Val Phe Ser Phe Ile Phe Leu Phe Val Met Trp Tyr Tyr Ser<br>305                 310                 315                 320 | 960 |

```
cct act tta aca ctg gta gtt ttg gca tca tta cca ata tat gcg ttt     1008
Pro Thr Leu Thr Leu Val Val Leu Ala Ser Leu Pro Ile Tyr Ala Phe
            325                 330                 335 tgg tct gcc ttt att agc cca att tta cgc act cga cta aat gat caa     1056
Trp Ser Ala Phe Ile Ser Pro Ile Leu Arg Thr Arg Leu Asn Asp Gln
            340                 345                 350 ttt gca cgc aat gca gat aat caa tct ttt tta gtg gaa agt att act     1104
Phe Ala Arg Asn Ala Asp Asn Gln Ser Phe Leu Val Glu Ser Ile Thr
            355                 360                 365 gcg gtt ggt acg gta aaa gca atg gca gtt gaa cct caa atg acc cgt     1152
Ala Val Gly Thr Val Lys Ala Met Ala Val Glu Pro Gln Met Thr Arg
            370                 375                 380 cgc tgg gat aat caa tta gca gct tat gtg gtt tct agt ttt cgg gta     1200
Arg Trp Asp Asn Gln Leu Ala Ala Tyr Val Val Ser Ser Phe Arg Val
385                 390                 395                 400 gct aag ttg gca atg gtt ggg cag caa gga gta caa ctc att caa aag     1248
Ala Lys Leu Ala Met Val Gly Gln Gln Gly Val Gln Leu Ile Gln Lys
            405                 410                 415 atg gtt att gtg gca act cta tgg att ggt gca aaa ttg gta att gaa     1296
Met Val Ile Val Ala Thr Leu Trp Ile Gly Ala Lys Leu Val Ile Glu
            420                 425                 430 ggc aag cta tcg gta ggt caa tta ata gca ttt aat atg ctg gca ggt     1344
Gly Lys Leu Ser Val Gly Gln Leu Ile Ala Phe Asn Met Leu Ala Gly
            435                 440                 445 cag gtg gcc gct cct gtt atc cgc ctg gca cag cta tgg caa gat ttt     1392
Gln Val Ala Ala Pro Val Ile Arg Leu Ala Gln Leu Trp Gln Asp Phe
            450                 455                 460 cag caa gta ggt att tca gtg gcg aga ttg ggt gat att tta aat act     1440
Gln Gln Val Gly Ile Ser Val Ala Arg Leu Gly Asp Ile Leu Asn Thr
465                 470                 475                 480 cca act gag cat tct aca tct cgc tta act tta cct gat att aag ggt     1488
Pro Thr Glu His Ser Thr Ser Arg Leu Thr Leu Pro Asp Ile Lys Gly
            485                 490                 495 gat att aca ttt gaa aat gtt gat ttt cgc tac aaa ata gat ggg cat     1536
Asp Ile Thr Phe Glu Asn Val Asp Phe Arg Tyr Lys Ile Asp Gly His
            500                 505                 510 tta ata tta cag aat tta aat tta cag att aac gct gga gag ata cta     1584
Leu Ile Leu Gln Asn Leu Asn Leu Gln Ile Asn Ala Gly Glu Ile Leu
            515                 520                 525 ggt atc gta gga cgc tct ggt tca ggt aaa tca aca ttg aca aaa tta     1632
Gly Ile Val Gly Arg Ser Gly Ser Gly Lys Ser Thr Leu Thr Lys Leu
            530                 535                 540 gta cag cgt tta tat gta cca gaa aat ggg cga ata tta gtt gat gga     1680
Val Gln Arg Leu Tyr Val Pro Glu Asn Gly Arg Ile Leu Val Asp Gly
545                 550                 555                 560 aac gat ttg gca tta gct gat ccc gct tgg ctg cgt cgc caa gtg ggt     1728
Asn Asp Leu Ala Leu Ala Asp Pro Ala Trp Leu Arg Arg Gln Val Gly
            565                 570                 575 gtt gtt ttg cag gaa aat gtg tta ctc aat cgt agt att cga gat aat     1776
Val Val Leu Gln Glu Asn Val Leu Leu Asn Arg Ser Ile Arg Asp Asn
            580                 585                 590 att gcc cta act gat acg ggc atg tca tta gag ttt att atc cag gct     1824
Ile Ala Leu Thr Asp Thr Gly Met Ser Leu Glu Phe Ile Ile Gln Ala
            595                 600                 605 gcc aag atg tct ggg gca cat gac ttt att atg gaa ttg cct gag ggt     1872
Ala Lys Met Ser Gly Ala His Asp Phe Ile Met Glu Leu Pro Glu Gly
            610                 615                 620 tat gat acg att gtt gga gag caa ggt gca ggc ttg tca ggt gga caa     1920
Tyr Asp Thr Ile Val Gly Glu Gln Gly Ala Gly Leu Ser Gly Gly Gln
```

```
cgc cag cgt atc gct att gcg cgt gct tta att acc aat ccg cgt att     1968
Arg Gln Arg Ile Ala Ile Ala Arg Ala Leu Ile Thr Asn Pro Arg Ile
            645                 650                 655 ttg att ttt gat gaa gct act agt gca tta gac tat gag tcg gaa agg     2016
Leu Ile Phe Asp Glu Ala Thr Ser Ala Leu Asp Tyr Glu Ser Glu Arg
            660                 665                 670 gct att atg caa aat atg cag gca att tgc caa ggt aga aca gtg ttg     2064
Ala Ile Met Gln Asn Met Gln Ala Ile Cys Gln Gly Arg Thr Val Leu
            675                 680                 685 att att gca cat cgc tta tct acc gta aaa atg gca cat cgc att att     2112
Ile Ile Ala His Arg Leu Ser Thr Val Lys Met Ala His Arg Ile Ile
            690                 695                 700 gca atg gac aag ggg aaa att gta gag caa ggc aca cat caa gaa ttg     2160
Ala Met Asp Lys Gly Lys Ile Val Glu Gln Gly Thr His Gln Glu Leu
705                 710                 715                 720 ttg caa aaa gaa gat ggt tac tat cgt tat tta tat gat ttg cag aat     2208
Leu Gln Lys Glu Asp Gly Tyr Tyr Arg Tyr Leu Tyr Asp Leu Gln Asn
                725                 730                 735 gga taaa                                                             2215
Gly

<210> SEQ ID NO 31
<211> LENGTH: 507
<212> TYPE: DNA
<213> ORGANISM: Moraxella bovis
<220> FEATURE:
<221> NAME/KEY: CDS
<222> LOCATION: (1)..(504)

<400> SEQUENCE: 31 atg acg aaa aag ttt gca gag cta ggt tta att gca tgg ctt tgg tct      48
Met Thr Lys Lys Phe Ala Glu Leu Gly Leu Ile Ala Trp Leu Trp Ser
1               5                   10                  15 aac tct gat atg cat aaa cat tgg acg ttg tct ttg ttt gcg acc aat      96
Asn Ser Asp Met His Lys His Trp Thr Leu Ser Leu Phe Ala Thr Asn
                20                  25                  30 gtt att ccg gca att gag aca ggt caa tat gtt ata ttg aaa aga gaa     144
Val Ile Pro Ala Ile Glu Thr Gly Gln Tyr Val Ile Leu Lys Arg Glu
            35                  40                  45 gat atg cct gta gca tat tgt agt tgg gct aaa ctt agt tta gaa aac     192
Asp Met Pro Val Ala Tyr Cys Ser Trp Ala Lys Leu Ser Leu Glu Asn
        50                  55                  60 gag gtt aaa tat att aac gat gtt act tct ctt aag tta gat gac tgg     240
Glu Val Lys Tyr Ile Asn Asp Val Thr Ser Leu Lys Leu Asp Asp Trp
65                  70                  75                  80 cag tca ggt gac cga aac tgg ttt att gac tgg att gct cca ttt ggc     288
Gln Ser Gly Asp Arg Asn Trp Phe Ile Asp Trp Ile Ala Pro Phe Gly
                85                  90                  95 gat agt ctt aca ctc aca aaa cac atg aga acg tta ttt tca gat gaa     336
Asp Ser Leu Thr Leu Thr Lys His Met Arg Thr Leu Phe Ser Asp Glu
            100                 105                 110 ttg ttt aga gcg att cgt gta gat gga aat tca tcg cat ggt aag ata     384
Leu Phe Arg Ala Ile Arg Val Asp Gly Asn Ser Ser His Gly Lys Ile
        115                 120                 125 tct gaa ttt tat gga aag tct gtt gat tca aaa tta gcc tca aga ata     432
Ser Glu Phe Tyr Gly Lys Ser Val Asp Ser Lys Leu Ala Ser Arg Ile
    130                 135                 140 ttt gca caa tat cac gaa gat ttg acg agc aaa ttg tca act cag aat     480
Phe Ala Gln Tyr His Glu Asp Leu Thr Ser Lys Leu Ser Thr Gln Asn
145                 150                 155                 160
```

```
aat ttt att ata tct aaa gat aat taa                          507
Asn Phe Ile Ile Ser Lys Asp Asn
            165
```

<210> SEQ ID NO 32
<211> LENGTH: 168
<212> TYPE: PRT
<213> ORGANISM: Moraxella bovis

<400> SEQUENCE: 32

```
Met Thr Lys Lys Phe Ala Glu Leu Gly Leu Ile Ala Trp Leu Trp Ser
 1               5                  10                  15

Asn Ser Asp Met His Lys His Trp Thr Leu Ser Leu Phe Ala Thr Asn
                20                  25                  30

Val Ile Pro Ala Ile Glu Thr Gly Gln Tyr Val Ile Leu Lys Arg Glu
            35                  40                  45

Asp Met Pro Val Ala Tyr Cys Ser Trp Ala Lys Leu Ser Leu Glu Asn
        50                  55                  60

Glu Val Lys Tyr Ile Asn Asp Val Thr Ser Leu Lys Leu Asp Asp Trp
 65                  70                  75                  80

Gln Ser Gly Asp Arg Asn Trp Phe Ile Asp Trp Ile Ala Pro Phe Gly
                85                  90                  95

Asp Ser Leu Thr Leu Thr Lys His Met Arg Thr Leu Phe Ser Asp Glu
            100                 105                 110

Leu Phe Arg Ala Ile Arg Val Asp Gly Asn Ser Ser His Gly Lys Ile
        115                 120                 125

Ser Glu Phe Tyr Gly Lys Ser Val Asp Ser Lys Leu Ala Ser Arg Ile
    130                 135                 140

Phe Ala Gln Tyr His Glu Asp Leu Thr Ser Lys Leu Ser Thr Gln Asn
145                 150                 155                 160

Asn Phe Ile Ile Ser Lys Asp Asn
            165
```

<210> SEQ ID NO 33
<211> LENGTH: 167
<212> TYPE: PRT
<213> ORGANISM: Pasteurella haemolytica

<400> SEQUENCE: 33

```
Met Asn Gln Ser Tyr Phe Asn Leu Leu Gly Asn Ile Thr Trp Leu Trp
 1               5                  10                  15

Met Asn Ser Ser Leu His Lys Glu Trp Ser Cys Glu Leu Leu Ala Arg
                20                  25                  30

Asn Val Ile Pro Ala Ile Glu Asn Glu Gln Tyr Met Leu Leu Ile Asp
            35                  40                  45

Asn Gly Ile Pro Ile Ala Tyr Cys Ser Trp Ala Asp Leu Asn Leu Glu
        50                  55                  60

Thr Glu Val Lys Tyr Ile Lys Asp Ile Asn Ser Leu Thr Pro Glu Glu
 65                  70                  75                  80

Trp Gln Ser Gly Asp Arg Arg Trp Ile Ile Asp Trp Val Ala Pro Phe
                85                  90                  95

Gly His Ser Gln Leu Leu Tyr Lys Lys Met Cys Gln Lys Tyr Pro Asp
            100                 105                 110

Met Ile Val Arg Ser Ile Arg Phe Tyr Pro Lys Gln Lys Glu Leu Gly
        115                 120                 125

Lys Ile Ala Tyr Phe Lys Gly Gly Lys Leu Asp Lys Lys Thr Ala Lys
```

```
                130             135             140
Lys Arg Phe Asp Thr Tyr Gln Glu Glu Leu Ala Thr Ala Leu Lys Asn
145                 150                 155                 160

Glu Phe Asn Phe Ile Lys Lys
                165

<210> SEQ ID NO 34
<211> LENGTH: 172
<212> TYPE: PRT
<213> ORGANISM: Actinobacillus pleuropneumoniae

<400> SEQUENCE: 34

Met Ser Lys Lys Ile Asn Gly Phe Glu Val Leu Gly Glu Val Ala Trp
  1               5                  10                  15

Leu Trp Ala Ser Ser Pro Leu His Arg Lys Trp Pro Leu Ser Leu Leu
                 20                  25                  30

Ala Ile Asn Val Leu Pro Ala Ile Glu Ser Asn Gln Tyr Val Leu Leu
             35                  40                  45

Lys Arg Asp Gly Phe Pro Ile Ala Phe Cys Ser Trp Ala Asn Leu Asn
 50                  55                  60

Leu Glu Asn Glu Ile Lys Tyr Leu Asp Asp Val Ala Ser Leu Val Ala
 65                  70                  75                  80

Asp Asp Trp Thr Ser Gly Asp Arg Arg Trp Phe Ile Asp Trp Ile Ala
                 85                  90                  95

Pro Phe Gly Asp Ser Ala Ala Leu Tyr Lys His Met Arg Asp Asn Phe
            100                 105                 110

Pro Asn Glu Leu Phe Arg Ala Ile Arg Val Asp Pro Asp Ser Arg Val
        115                 120                 125

Gly Lys Ile Ser Glu Phe His Gly Gly Lys Ile Asp Lys Lys Leu Ala
130                 135                 140

Ser Lys Ile Phe Gln Gln Tyr His Phe Glu Leu Met Ser Glu Leu Lys
145                 150                 155                 160

Asn Lys Gln Asn Phe Lys Phe Ser Leu Val Asn Ser
                165                 170

<210> SEQ ID NO 35
<211> LENGTH: 170
<212> TYPE: PRT
<213> ORGANISM: Escherichia coli

<400> SEQUENCE: 35

Met Asn Arg Asn Asn Pro Leu Glu Val Leu Gly His Val Ser Trp Leu
  1               5                  10                  15

Trp Ala Ser Ser Pro Leu His Arg Asn Trp Pro Val Ser Leu Phe Ala
                 20                  25                  30

Ile Asn Val Leu Pro Ala Ile Arg Ala Asn Gln Tyr Ala Leu Leu Thr
             35                  40                  45

Arg Asp Asn Tyr Pro Val Ala Tyr Cys Ser Trp Ala Asn Leu Ser Leu
 50                  55                  60

Glu Asn Glu Ile Lys Tyr Leu Asn Asp Val Thr Ser Leu Val Ala Glu
 65                  70                  75                  80

Asp Trp Thr Ser Gly Asp Arg Lys Trp Phe Ile Val Trp Ile Ala Pro
                 85                  90                  95

Phe Gly Asp Asn Gly Ala Leu Tyr Lys Tyr Met Arg Lys Lys Phe Pro
            100                 105                 110

Asp Glu Leu Phe Arg Ala Ile Arg Val Asp Pro Lys Thr His Val Gly
```

-continued

```
                115                 120                       125
Lys Val Ser Glu Phe His Gly Gly Lys Ile Asp Lys Gln Leu Ala Asn
            130                 135                 140

Lys Ile Phe Lys Gln Tyr His His Glu Leu Ile Thr Glu Val Lys Asn
145                 150                 155                 160

Lys Ser Asp Phe Asn Phe Ser Leu Thr Gly
                165                 170
```

<210> SEQ ID NO 36
<211> LENGTH: 1428
<212> TYPE: DNA
<213> ORGANISM: Moraxella bovis
<220> FEATURE:
<221> NAME/KEY: CDS
<222> LOCATION: (1)..(1425)

<400> SEQUENCE: 36

```
atg ttt ata caa gca ctt aaa gat ttt ttt att cgc tat ata acc gtt         48
Met Phe Ile Gln Ala Leu Lys Asp Phe Phe Ile Arg Tyr Ile Thr Val
 1               5                  10                  15 tgg cgc aat aca tgg gca gtt cga gac caa cta acc cct cct aag cgt         96
Trp Arg Asn Thr Trp Ala Val Arg Asp Gln Leu Thr Pro Pro Lys Arg
            20                  25                  30 act aaa gaa gaa ctc gct ttt ctt cct gca cat cta gaa ctc act gac        144
Thr Lys Glu Glu Leu Ala Phe Leu Pro Ala His Leu Glu Leu Thr Asp
        35                  40                  45 aca cct gta tcc aga tct tct aag tgg aca gct aga ata atc atg ata        192
Thr Pro Val Ser Arg Ser Ser Lys Trp Thr Ala Arg Ile Ile Met Ile
    50                  55                  60 ttt gtc cta ttt gct ttg cta tgg tct tgg gtt gga cag att gac att        240
Phe Val Leu Phe Ala Leu Leu Trp Ser Trp Val Gly Gln Ile Asp Ile
65                  70                  75                  80 gtt gct aca gct tca ggt aaa att tct tca ggt agc cgt agc aag act        288
Val Ala Thr Ala Ser Gly Lys Ile Ser Ser Gly Ser Arg Ser Lys Thr
                85                  90                  95 att caa tct ttg gaa aca gcg ata gtt aaa gca gtt tat gta cgt gat        336
Ile Gln Ser Leu Glu Thr Ala Ile Val Lys Ala Val Tyr Val Arg Asp
            100                 105                 110 ggt caa aat gtt caa caa ggt gaa ata tta gta gat tta gtg gga atc        384
Gly Gln Asn Val Gln Gln Gly Glu Ile Leu Val Asp Leu Val Gly Ile
        115                 120                 125 ggt tca gat agt gat gtt gct cag tcc gag aaa gcc ctt cga gca gcg        432
Gly Ser Asp Ser Asp Val Ala Gln Ser Glu Lys Ala Leu Arg Ala Ala
    130                 135                 140 caa tta tct aag cta cgc ctt gaa gca att tta tca gca tta aat cac        480
Gln Leu Ser Lys Leu Arg Leu Glu Ala Ile Leu Ser Ala Leu Asn His
145                 150                 155                 160 cgt att aat cct cag att gat gta gca tat gca aag tct tta aat att        528
Arg Ile Asn Pro Gln Ile Asp Val Ala Tyr Ala Lys Ser Leu Asn Ile
                165                 170                 175 tca gaa tcg gaa att aat gaa gct caa act tta gcc caa aat caa tat        576
Ser Glu Ser Glu Ile Asn Glu Ala Gln Thr Leu Ala Gln Asn Gln Tyr
            180                 185                 190 caa gca tgg tta gca caa gat gaa caa cta aaa tta acc tta aaa gga        624
Gln Ala Trp Leu Ala Gln Asp Glu Gln Leu Lys Leu Thr Leu Lys Gly
        195                 200                 205 cat caa gca gaa tta caa tct gct cga tcc caa gaa caa aag ttg gtt        672
His Gln Ala Glu Leu Gln Ser Ala Arg Ser Gln Glu Gln Lys Leu Val
    210                 215                 220 tca gtt ggt gca att gaa cat caa aag act gat gat tat cgg agt ctc        720
Ser Val Gly Ala Ile Glu His Gln Lys Thr Asp Asp Tyr Arg Ser Leu
```

```
Ser Val Gly Ala Ile Glu His Gln Lys Thr Asp Asp Tyr Arg Ser Leu
225                 230                 235                 240 aaa gca gaa aat ttt ata tct gag cat gct tat cta gaa caa gaa agc    768
Lys Ala Glu Asn Phe Ile Ser Glu His Ala Tyr Leu Glu Gln Glu Ser
                245                 250                 255 aaa tta ctt agc aat caa aat gat tta caa agt aca cgt agt cag att    816
Lys Leu Leu Ser Asn Gln Asn Asp Leu Gln Ser Thr Arg Ser Gln Ile
            260                 265                 270 caa aaa ata cag gct gca atc atg caa gct gaa cag aac cgt atg tta    864
Gln Lys Ile Gln Ala Ala Ile Met Gln Ala Glu Gln Asn Arg Met Leu
        275                 280                 285 tat act caa aat cta aaa cgt gat aca tta gaa tct tta cgc caa acc    912
Tyr Thr Gln Asn Leu Lys Arg Asp Thr Leu Glu Ser Leu Arg Gln Thr
    290                 295                 300 aat gaa cag att aat caa tat act ggt caa act aat aaa gct aag cag    960
Asn Glu Gln Ile Asn Gln Tyr Thr Gly Gln Thr Asn Lys Ala Lys Gln
305                 310                 315                 320 cga cag aaa ttg ctg agt att aaa tca cct gtt aat ggt act ata caa   1008
Arg Gln Lys Leu Leu Ser Ile Lys Ser Pro Val Asn Gly Thr Ile Gln
                325                 330                 335 gag cta aca gct tat act tta ggt gga gtt gta caa gca gca caa aaa   1056
Glu Leu Thr Ala Tyr Thr Leu Gly Gly Val Val Gln Ala Ala Gln Lys
            340                 345                 350 att atg gtt gtg gca cct aac gat aat caa gtg gaa gta gag gta tta   1104
Ile Met Val Val Ala Pro Asn Asp Asn Gln Val Glu Val Glu Val Leu
        355                 360                 365 gtg cta aat aaa gat atc ggc ttt gta aaa gct ggg cag aat gtt atc   1152
Val Leu Asn Lys Asp Ile Gly Phe Val Lys Ala Gly Gln Asn Val Ile
    370                 375                 380 atc aaa atc gag agt ttt cct tat aca cgt tat ggt tat tta aca ggt   1200
Ile Lys Ile Glu Ser Phe Pro Tyr Thr Arg Tyr Gly Tyr Leu Thr Gly
385                 390                 395                 400 aaa ata aaa agt att agt cat gat gct ata gaa cat caa cat tta ggt   1248
Lys Ile Lys Ser Ile Ser His Asp Ala Ile Glu His Gln His Leu Gly
                405                 410                 415 cta gtg tat act gca ctt gtt tct ctt gat aaa agc aca tta aat ata   1296
Leu Val Tyr Thr Ala Leu Val Ser Leu Asp Lys Ser Thr Leu Asn Ile
            420                 425                 430 gat gga gta aca atc aac tta acg cca gga atg aat gtt act gct gaa   1344
Asp Gly Val Thr Ile Asn Leu Thr Pro Gly Met Asn Val Thr Ala Glu
        435                 440                 445 att aaa aca ggt aaa cgt cgt gtt ttg gat tat ata tta agt cca ttg   1392
Ile Lys Thr Gly Lys Arg Arg Val Leu Asp Tyr Ile Leu Ser Pro Leu
    450                 455                 460 cag aca aaa gtt gat gaa agt ttt cga gaa cgc taa                   1428
Gln Thr Lys Val Asp Glu Ser Phe Arg Glu Arg
465                 470                 475

<210> SEQ ID NO 37
<211> LENGTH: 475
<212> TYPE: PRT
<213> ORGANISM: Moraxella bovis

<400> SEQUENCE: 37

Met Phe Ile Gln Ala Leu Lys Asp Phe Phe Ile Arg Tyr Ile Thr Val
1               5                   10                  15

Trp Arg Asn Thr Trp Ala Val Arg Asp Gln Leu Thr Pro Pro Lys Arg
            20                  25                  30

Thr Lys Glu Glu Leu Ala Phe Leu Pro Ala His Leu Glu Leu Thr Asp
        35                  40                  45
```

-continued

```
Thr Pro Val Ser Arg Ser Ser Lys Trp Thr Ala Arg Ile Ile Met Ile
     50                  55                  60

Phe Val Leu Phe Ala Leu Leu Trp Ser Trp Val Gly Gln Ile Asp Ile
 65                  70                  75                  80

Val Ala Thr Ala Ser Gly Lys Ile Ser Ser Gly Arg Ser Lys Thr
                 85                  90                  95

Ile Gln Ser Leu Glu Thr Ala Ile Val Lys Ala Val Tyr Val Arg Asp
                100                 105                 110

Gly Gln Asn Val Gln Gln Gly Glu Ile Leu Val Asp Leu Val Gly Ile
                115                 120                 125

Gly Ser Asp Ser Asp Val Ala Gln Ser Glu Lys Ala Leu Arg Ala Ala
                130                 135                 140

Gln Leu Ser Lys Leu Arg Leu Glu Ala Ile Leu Ser Ala Leu Asn His
145                 150                 155                 160

Arg Ile Asn Pro Gln Ile Asp Val Ala Tyr Ala Lys Ser Leu Asn Ile
                165                 170                 175

Ser Glu Ser Glu Ile Asn Glu Ala Gln Thr Leu Ala Gln Asn Gln Tyr
                180                 185                 190

Gln Ala Trp Leu Ala Gln Asp Glu Gln Leu Lys Leu Thr Leu Lys Gly
                195                 200                 205

His Gln Ala Glu Leu Gln Ser Ala Arg Ser Gln Glu Gln Lys Leu Val
                210                 215                 220

Ser Val Gly Ala Ile Glu His Gln Lys Thr Asp Asp Tyr Arg Ser Leu
225                 230                 235                 240

Lys Ala Glu Asn Phe Ile Ser Glu His Ala Tyr Leu Glu Gln Glu Ser
                245                 250                 255

Lys Leu Leu Ser Asn Gln Asn Asp Leu Gln Ser Thr Arg Ser Gln Ile
                260                 265                 270

Gln Lys Ile Gln Ala Ala Ile Met Gln Ala Glu Gln Asn Arg Met Leu
                275                 280                 285

Tyr Thr Gln Asn Leu Lys Arg Asp Thr Leu Glu Ser Leu Arg Gln Thr
                290                 295                 300

Asn Glu Gln Ile Asn Gln Tyr Thr Gly Gln Thr Asn Lys Ala Lys Gln
305                 310                 315                 320

Arg Gln Lys Leu Leu Ser Ile Lys Ser Pro Val Asn Gly Thr Ile Gln
                325                 330                 335

Glu Leu Thr Ala Tyr Thr Leu Gly Gly Val Val Gln Ala Ala Gln Lys
                340                 345                 350

Ile Met Val Val Ala Pro Asn Asp Asn Gln Val Glu Val Glu Val Leu
                355                 360                 365

Val Leu Asn Lys Asp Ile Gly Phe Val Lys Ala Gly Gln Asn Val Ile
                370                 375                 380

Ile Lys Ile Glu Ser Phe Pro Tyr Thr Arg Tyr Gly Tyr Leu Thr Gly
385                 390                 395                 400

Lys Ile Lys Ser Ile Ser His Asp Ala Ile Glu His Gln His Leu Gly
                405                 410                 415

Leu Val Tyr Thr Ala Leu Val Ser Leu Asp Lys Ser Thr Leu Asn Ile
                420                 425                 430

Asp Gly Val Thr Ile Asn Leu Thr Pro Gly Met Asn Val Thr Ala Glu
                435                 440                 445

Ile Lys Thr Gly Lys Arg Arg Val Leu Asp Tyr Ile Leu Ser Pro Leu
                450                 455                 460
```

```
Gln Thr Lys Val Asp Glu Ser Phe Arg Glu Arg
465                 470                 475
```

<210> SEQ ID NO 38
<211> LENGTH: 478
<212> TYPE: PRT
<213> ORGANISM: Pasteurella haemolytica

<400> SEQUENCE: 38

```
Met Lys Ile Trp Leu Ser Gly Ile Tyr Glu Phe Phe Leu Arg Tyr Lys
  1               5                  10                  15

Asn Ile Trp Ala Glu Val Trp Lys Ile Arg Lys Glu Leu Asp His Pro
             20                  25                  30

Asn Arg Lys Lys Asp Glu Ser Glu Phe Leu Pro Ala His Leu Glu Leu
         35                  40                  45

Ile Glu Thr Pro Val Ser Lys Lys Pro Arg Leu Ile Ala Tyr Leu Ile
     50                  55                  60

Met Leu Phe Leu Val Val Ala Ile Val Leu Ala Ser Val Ser Lys Val
 65                  70                  75                  80

Glu Ile Val Ala Thr Ala Pro Gly Lys Leu Thr Phe Ser Gly Arg Ser
                 85                  90                  95

Lys Glu Ile Lys Pro Ile Glu Asn Ala Ile Val Gln Glu Ile Phe Val
            100                 105                 110

Lys Asp Gly Gln Phe Val Glu Lys Gly Gln Leu Leu Val Ser Leu Thr
        115                 120                 125

Ala Leu Gly Ser Asp Ala Asp Ile Lys Lys Thr Met Ala Ser Leu Ser
    130                 135                 140

Leu Ala Lys Leu Glu Asn Tyr Arg Tyr Gln Thr Leu Leu Thr Ala Ile
145                 150                 155                 160

Glu Lys Glu Ser Leu Pro Val Ile Asp Leu Ser Arg Thr Glu Phe Lys
                165                 170                 175

Asp Ser Ser Glu Glu Asp Arg Leu Arg Ile Lys His Leu Ile Glu Glu
            180                 185                 190

Gln Tyr Thr Thr Trp Gln Lys Gln Lys Thr Gln Lys Thr Leu Ala Tyr
        195                 200                 205

Lys Arg Lys Glu Ala Glu Lys Gln Thr Ile Phe Ala Tyr Val Arg Lys
    210                 215                 220

Tyr Glu Gly Ala Thr Arg Ile Glu Gln Glu Lys Leu Lys Asp Phe Lys
225                 230                 235                 240

Ala Leu Tyr Lys Gln Lys Ser Leu Ser Lys His Glu Leu Leu Ala Gln
                245                 250                 255

Glu Asn Lys Leu Ile Glu Ala Gln Asn Ala Val Ala Val Tyr Arg Ser
            260                 265                 270

Lys Leu Asn Glu Leu Glu Asn Asp Leu Leu Asn Val Lys Glu Glu Leu
        275                 280                 285

Glu Leu Ile Thr Gln Phe Phe Lys Ser Asp Val Leu Glu Lys Leu Lys
    290                 295                 300

Gln His Ile Glu Asn Glu Arg Gln Leu Arg Leu Glu Leu Glu Lys Asn
305                 310                 315                 320

Asn Gln Arg Arg Gln Ala Ser Met Ile Arg Ala Pro Val Ser Gly Thr
                325                 330                 335

Val Gln Gln Leu Lys Ile His Thr Ile Gly Gly Val Val Thr Thr Ala
            340                 345                 350

Glu Thr Leu Met Ile Ile Val Pro Glu Asp Asp Val Leu Glu Ala Thr
        355                 360                 365
```

```
Ala Leu Val Pro Asn Lys Asp Ile Gly Phe Val Ala Ala Gly Gln Glu
    370                 375                 380

Val Ile Ile Lys Val Glu Thr Phe Pro Tyr Thr Arg Tyr Gly Tyr Leu
385                 390                 395                 400

Thr Gly Arg Ile Lys His Ile Ser Pro Asp Ala Ile Glu Gln Pro Asn
                405                 410                 415

Val Gly Leu Val Phe Asn Ala Thr Ile Ala Ile Asp Arg Lys Asn Leu
            420                 425                 430

Thr Ser Pro Asp Gly Arg Lys Ile Asp Leu Ser Ser Gly Met Thr Ile
        435                 440                 445

Thr Ala Glu Ile Lys Thr Gly Glu Arg Ser Val Met Ser Tyr Leu Leu
    450                 455                 460

Ser Pro Leu Glu Glu Ser Val Thr Glu Ser Leu Arg Glu Arg
465                 470                 475
```

<210> SEQ ID NO 39
<211> LENGTH: 478
<212> TYPE: PRT
<213> ORGANISM: Actinobacillus pleuropneumoniae

<400> SEQUENCE: 39

```
Met Lys Thr Trp Leu Met Gly Leu Tyr Glu Phe Phe Gln Arg Tyr Lys
1               5                   10                  15

Thr Val Trp Thr Glu Ile Trp Lys Ile Arg His Gln Leu Asp Thr Pro
                20                  25                  30

Asp Arg Glu Lys Asp Glu Asn Glu Phe Leu Pro Ala His Leu Glu Leu
            35                  40                  45

Ile Glu Thr Pro Val Ser Lys Lys Pro Arg Leu Ile Ala Tyr Leu Ile
        50                  55                  60

Met Leu Phe Leu Phe Leu Ala Leu Val Ile Ser Ile Val Ser His Val
65                  70                  75                  80

Glu Ile Val Ala Thr Ala Thr Gly Lys Leu Ala Phe Ser Asp Arg Ser
                85                  90                  95

Lys Glu Ile Lys Pro Ile Glu Asn Ala Leu Val Lys Glu Ile Phe Val
                100                 105                 110

Gln Asp Gly Gln Phe Val Glu Lys Asp Gln Leu Leu Leu His Leu Thr
            115                 120                 125

Ala Leu Gly Ala Asp Ala Asp Gln Gln Lys Thr Lys Ser Ser Leu Ser
130                 135                 140

Leu Thr Lys Leu Glu Arg Tyr Arg Tyr Glu Ile Leu Leu Glu Ala Val
145                 150                 155                 160

Ala Ala Asp Arg Leu Pro Leu Ile Glu Leu Thr Lys Asp Glu Phe Lys
                165                 170                 175

His Ala Thr Glu Glu Asp Lys Thr Arg Ile Arg Tyr Leu Ile Thr Glu
            180                 185                 190

Gln Phe Glu Ala Trp Gln Lys Gln Lys Tyr Gln Lys Glu Leu Ala Leu
        195                 200                 205

Gln Arg Arg Glu Ala Glu Lys Gln Thr Val Leu Ala Asn Ile Arg Lys
    210                 215                 220

Tyr Glu Gly Ile Ser Arg Val Glu Asn Glu Arg Leu Lys Asp Leu Lys
225                 230                 235                 240

Lys Leu Phe Asn Ser Lys Ser Thr Ser Lys His Asp Val Leu Thr Gln
                245                 250                 255

Glu Asn Arg His Ile Glu Ala Val Asn Glu Leu Ala Val Tyr Lys Ser
```

```
                    260                 265                 270
Arg Leu Asn Glu Val Glu Ser Asp Leu Arg Gln Ala Lys Glu Glu Ile
            275                 280                 285
His Leu Ile Thr Gln Leu Phe Arg Ala Asp Ile Leu Glu Lys Leu Lys
        290                 295                 300
Gln Asn Val Glu Ala Glu Lys Gln Leu Ser Leu Glu Leu Glu Lys Asn
305                 310                 315                 320
Glu Gln Arg Gln Ile Ala Ser Val Ile Arg Ala Pro Val Ser Gly Thr
                325                 330                 335
Val Gln Gln Leu Lys Thr His Thr Val Gly Val Val Thr Thr Ala
            340                 345                 350
Glu Thr Leu Met Val Ile Ala Pro Glu Asp Asp Val Leu Glu Val Thr
        355                 360                 365
Ala Leu Ile Gln Asn Lys Asp Ile Gly Phe Ile Glu Val Gly Gln Asp
        370                 375                 380
Ala Val Ile Lys Val Glu Thr Phe Pro Tyr Thr Arg Tyr Gly Tyr Leu
385                 390                 395                 400
Met Gly Lys Val Lys Asn Ile Thr Leu Glu Ala Ile Glu His Pro Gln
                405                 410                 415
Leu Gly Leu Val Phe Asn Ser Ile Ser Ile Asp Arg Lys Thr Leu
            420                 425                 430
Ser Gly Lys Asp Gly Lys Glu Ile Glu Leu Gly Ser Gly Met Ser Val
        435                 440                 445
Thr Ala Glu Ile Lys Thr Gly Glu Arg Ser Val Ile Ser Tyr Leu Leu
        450                 455                 460
Ser Pro Leu Glu Glu Ser Val Ser Glu Ser Leu Arg Glu Arg
465                 470                 475

<210> SEQ ID NO 40
<211> LENGTH: 478
<212> TYPE: PRT
<213> ORGANISM: Escherichia coli

<400> SEQUENCE: 40

Met Lys Thr Trp Leu Met Gly Phe Ser Glu Phe Leu Leu Arg Tyr Lys
1               5                   10                  15
Leu Val Trp Ser Glu Thr Trp Lys Ile Arg Lys Gln Leu Asp Thr Pro
            20                  25                  30
Val Arg Glu Lys Asp Glu Asn Glu Phe Leu Pro Ala His Leu Glu Leu
        35                  40                  45
Ile Glu Thr Pro Val Ser Arg Arg Pro Arg Leu Val Ala Tyr Phe Ile
    50                  55                  60
Met Gly Phe Leu Val Ile Ala Phe Ile Leu Ser Val Leu Gly Gln Val
65                  70                  75                  80
Glu Ile Val Ala Thr Ala Asn Gly Lys Leu Thr Leu Ser Gly Arg Ser
                85                  90                  95
Lys Glu Ile Lys Pro Ile Glu Asn Ser Ile Val Lys Glu Ile Ile Val
            100                 105                 110
Lys Glu Gly Glu Ser Val Arg Lys Gly Asp Val Leu Lys Leu Thr
        115                 120                 125
Ala Leu Gly Ala Glu Ala Asp Thr Leu Lys Thr Gln Ser Ser Leu Leu
    130                 135                 140
Gln Ala Arg Leu Glu Gln Ile Arg Tyr Gln Ile Leu Ser Arg Ser Ile
145                 150                 155                 160
```

```
Glu Leu Asn Lys Leu Pro Glu Leu Lys Leu Pro Asp Glu Pro Tyr Phe
            165                 170                 175

Gln Asn Val Ser Glu Glu Val Leu Arg Leu Thr Ser Leu Ile Lys
        180                 185                 190

Glu Gln Phe Ser Thr Trp Gln Asn Gln Lys Tyr Gln Lys Glu Leu Asn
            195                 200                 205

Leu Asp Lys Lys Arg Ala Glu Arg Leu Thr Ile Leu Ala Arg Ile Asn
210                 215                 220

Arg Tyr Glu Asn Val Ser Arg Val Glu Lys Ser Arg Leu Asp Asp Phe
225                 230                 235                 240

Arg Ser Leu Leu His Lys Gln Ala Ile Ala Lys His Ala Val Leu Glu
                245                 250                 255

Gln Glu Asn Lys Tyr Val Glu Ala Ala Asn Glu Leu Arg Val Tyr Lys
            260                 265                 270

Ser Gln Leu Glu Gln Ile Glu Ser Glu Ile Leu Ser Ala Lys Glu Glu
        275                 280                 285

Tyr Gln Leu Val Thr Gln Leu Phe Lys Asn Glu Ile Leu Asp Lys Leu
        290                 295                 300

Arg Gln Thr Thr Asp Ser Ile Glu Leu Leu Thr Leu Glu Leu Glu Lys
305                 310                 315                 320

Asn Glu Glu Arg Gln Gln Ala Ser Val Ile Arg Ala Pro Val Ser Gly
                325                 330                 335

Lys Val Gln Gln Leu Lys Val His Thr Glu Gly Gly Val Val Thr Thr
            340                 345                 350

Ala Glu Thr Leu Met Val Ile Val Pro Glu Asp Asp Thr Leu Glu Val
            355                 360                 365

Thr Ala Leu Val Gln Asn Lys Asp Ile Gly Phe Ile Asn Val Gly Gln
        370                 375                 380

Asn Ala Ile Ile Lys Val Glu Ala Phe Pro Tyr Thr Arg Tyr Gly Tyr
385                 390                 395                 400

Leu Val Gly Lys Val Lys Asn Ile Asn Leu Asp Ala Ile Glu Asp Gln
                405                 410                 415

Lys Leu Gly Leu Val Phe Asn Val Ile Val Ser Val Glu Glu Asn Asp
            420                 425                 430

Leu Ser Thr Gly Asn Lys His Ile Pro Leu Ser Ser Gly Met Ala Val
        435                 440                 445

Thr Ala Glu Ile Lys Thr Gly Met Arg Ser Val Ile Ser Tyr Leu Leu
    450                 455                 460

Ser Pro Leu Glu Glu Ser Val Thr Glu Ser Leu His Glu Arg
465                 470                 475

<210> SEQ ID NO 41
<211> LENGTH: 24
<212> TYPE: DNA
<213> ORGANISM: Artificial Sequence
<220> FEATURE:
<223> OTHER INFORMATION: Description of Artificial Sequence: Primer
<221> NAME/KEY: modified_base
<222> LOCATION: (14)
<223> OTHER INFORMATION: a, t, c, g, other or unknown

<400> SEQUENCE: 41
tagtaaatta aatnactwaa cact                                          24
```

MORAXELLA BOVIS CYTOTOXIN, CYTOTOXIN GENE, ANTIBODIES AND VACCINES FOR PREVENTION AND TREATMENT OF MORAXELLA BOVIS INFECTIONS

BACKGROUND OF THE INVENTION

1. Field of the Invention

The current invention concerns *Moraxella bovis* cytotoxin and a gene encoding *Moraxella bovis* cytotoxin. In particular, the invention concerns identification, isolation, cloning and identification of nucleotide sequence of the *Moraxella bovis* gene mbxA and adjacent genes mbxB, mbxC and mbxD, partial purification of the native cytotoxin, preparation of a purified native and recombinant *Moraxella bovis* cytotoxin, an amino acid sequence of the cytotoxins, preparation of antibodies against the *Moraxella bovis* cytotoxin, preparation of vaccines against *Moraxella bovis* and a method for prevention and treatment of infectious bovine keratoconjunctivitis caused by *Moraxella bovis*.

2. Background and Related Disclosures

Infectious bovine keratoconjunctivitis (IBK) also called pinkeye, caused by *Moraxella bovis* (*M. bovis*) infection ranks as one of the most important cattle diseases in the United States and abroad. Annual estimated incidence of the disease is 5% of all beef cattle with greater than 50% of all herds affected. Epizootics also occur with case attack rates approaching 90-100% of yearling cattle. Affected cattle do not eat and fail to gain weight. Economic losses due to lower market weights of affected cattle and calves and ocular scarring and treatment associated expenses are estimated to exceed $150,000,000 annually. Effective control measures that could substantially reduce this expense are not available as the commercially available vaccines have low efficacy.

Animals affected with IBK exhibit corneal ulceration, edema, ocular pain, photophobia and lacrimation. Control of IBK using antimicrobial treatments has been only partially successful. Antimicrobials have been used to eliminate the carrier state in experimental and field trials, but these treatments have drawbacks that include emergence of resistant bacteria in cattle and the general environment, potential for adulteration of the nation's food supply, high cost and marginal economic benefit.

Topical and oral administration of antibiotics has proven somewhat effective for treatment of pinkeye, but the high cost and losses associated with the ongoing disease often outweigh the benefits of such treatment. Topical therapy alone does not eliminate *M. bovis* from non-ocular sites such as nasal choanae and vagina where it is known to reside.

Consequently, an effective vaccine or antibody for prevention and treatment of IBK would be an important component of a successful IBK control program.

So far, vaccines prepared from killed or live bacteria, isolated pili, or ribosomes have had limited benefit for immunization of cattle in the field (*Proc. Am. Assoc. Bov. Pract.*, 20:26-32 (1987)). Nevertheless, a large body of field and experimental data exist to show that acquired resistance to pinkeye does develop after the natural occurrence of the infection.

At least two attributes, namely pili and cytotoxin (leukotoxin/hemolysin/cytolysin), of the *M. bovis* organism are important in the pathogenesis of IBK. *M. bovis* pili facilitate adhesion of the bacterium to the corneal epithelium and are required for colonization. Pili are highly immunogenic, but have antigenic diversity due to the presence of at least two structural pilin genes and variability in the amino acid composition of the pilin molecule. Variability in pilus gene expression is regulated by a site-specific DNA inversion system. Limited antigenic cross-reactivity was found in vaccines prepared from heterologous pili. *M. bovis* pili in monovalent or multivalent formulations have demonstrated variable efficacy, attributed to pilus gene inversion that occurs during infection (*Vet. Microbiol.*, 45:129-138 (1995)). The emergence of novel pili serotypes during epizootics of IBK has been documented (*Am. J. Vet. Res.*, 50:1437-1441 (1989)). These studies suggest that because of the pili heterogeneity pilus based vaccines will not be 100% effective at preventing IBK.

The *Moraxella bovis* cytotoxin (hemolysin) is an important component of immunity to IBK (*FEMS Microbiol. Lett.*, 124:69-74 (1994)).

*Moraxella bovis* produces a heat labile, approximately 100 kD cytotoxin (hemolysin) that causes cell lysis by forming pores in cell membranes via a calcium-dependent process (*Infect. Immunol.*, 59:1148-1152 (1991)). In vitro, culture filtrates from broth cultures of hemolytic but not nonhemolytic strains of *M. bovis* cause lysis of bovine neutrophils (*Am. J. Vet. Res.*, 51:191-196 (1990)). In vivo, the ocular damage caused by a purified hemolytic and cytotoxic fraction of *M. bovis* mimics the lesions seen in naturally occurring IBK (*Vet. Microbiol.*, 42:15-33 (1994)). Unlike the pilin molecule, the *M. bovis* cytotoxin appears to be more conserved between different *M. bovis* isolates. Serologic studies show that antihemolytic antibodies recognize hemolysin from different strains of *M. bovis* (*Am. J. Vet. Res.*, 46:1011-1014 (1985)) and, thus, form an important component of immunity to IBK (*FEMS Microbiol. Lett.*, 124:69-74 (1994)).

In view of the severity of consequences of infectious bovine keratoconjunctivitis, it would be important to have available an effective vaccine and/or anti-*Moraxella bovis* antibodies that could prevent this condition.

This invention, therefore, concerns an effective IBK vaccine, anti-*Moraxella bovis* antibodies and to that end an isolation and partial purification of the native *Moraxella bovis* cytotoxin, a characterization of the *M. bovis* cytotoxin gene, identification of *M. bovis* cytotoxin amino acid sequence, preparation of recombinant *M. bovis* cytotoxin and determination of its efficacy in a vaccine for prophylaxis and treatment of IBK.

All patents, patent applications and publications cited herein are hereby incorporated by reference in their entirety.

SUMMARY

One aspect of the current invention is a vaccine for prevention of infectious bovine keratoconjunctivitis comprising a purified native or recombinant *Moraxella bovis* cytotoxin.

Still another aspect of the current invention is a DNA sequence of the *Moraxella bovis* gene depicted by SEQ ID NO: 1.

Still another aspect of the current invention is a DNA sequence of the *Moraxella bovis* gene B depicted by SEQ ID NO: 30.

Still another aspect of the current invention is a DNA sequence of the *Moraxella bovis* gene C depicted by SEQ ID NO: 31.

Still another aspect of the current invention is a DNA sequence of the *Moraxella bovis* gene D depicted by SEQ ID NO: 36.

Yet another aspect of the current invention is an amino acid sequence of *Moraxella bovis* cytotoxin A depicted by SEQ ID NO: 2 or a partially purified native or recombinantly prepared cytotoxin comprising SEQ ID NO: 2.

Yet another aspect of the current invention is an amino acid sequence of *Moraxella bovis* cytotoxin B depicted by SEQ ID NO: 30 or a partially purified native or recombinantly prepared cytotoxin comprising SEQ ID NO: 18.

Yet another aspect of the current invention is an amino acid sequence of *Moraxella bovis* cytotoxin C depicted by SEQ ID NO: 31 or a partially purified native or recombinantly prepared cytotoxin comprising SEQ ID NO: 32.

Yet another aspect of the current invention is an amino acid sequence of *Moraxella bovis* cytotoxin D depicted by SEQ ID NO: 36 or a partially purified native or recombinantly prepared cytotoxin comprising SEQ ID NO: 37.

Still another aspect of the current invention is a method for purification or partial purification of the *Moraxella bovis* cytotoxin and its stabilization.

Still another aspect of the current invention is a method for prevention of IBK in cattle and calves by vaccinating said cattle or calves with a vaccine comprising a partially purified native or recombinant *Moraxella bovis* cytotoxin comprising SEQ ID NO: 2.

BRIEF DESCRIPTION OF FIGURES

FIG. 3 shows nucleotide (SEQ ID NO: 1) and deduced amino acid (SEQ ID NO: 2) sequences of *M. bovis* RTXA (MbxA) gene.

FIG. 4 shows the alignment of the deduced amino acid sequence of *M. bovis* RTXA (MbxA) gene (SEQ ID NO: 2) and RTX toxins of *M. (Pasteurella) haemolytica* (LktA) (SEQ ID NO: 3), *A. pleuropneumoniae* (ApxIA) (SEQ ID NO: 4) and *E. coli* (HlyA)(SEQ ID NO: 5).

FIG. 8 shows nucleotide (SEQ ID NO: 30) and deduced amino acid (SEQ ID NO: 18) sequences of *M. bovis* RTXB (MbxB) gene.

FIG. 9 shows the alignment of the deduced amino acid sequence of *M. bovis* RTXB (MbxB) gene (SEQ ID NO: 18) and RTX toxins from *M. (Pasteurella) haemolytica* (LktB) (SEQ ID NO: 19), *A. pleuropneumoniae* (ApxIIB) (SEQ ID NO:20) and *E. coli* (HlyB)(SEQ ID NO: 21).

FIG. 10 shows nucleotide (SEQ ID NO: 31) and deduced amino acid (SEQ ID Nos: 32) sequences of *M. bovis* RTXC (MbxC) gene.

FIG. 11 shows the alignment of the deduced amino acid sequence (SEQ ID NO: 32) of *M. bovis* RTXC (MbxC) gene and RTX toxins of *M. (Pasteurella) haemolytica* (LktC) (SEQ ID NO: 33), *A. pleuropneumoniae* (ApxIIC) (SEQ ID NO:34) and *E. coli* (HlyC)(SEQ ID NO: 35).

FIG. 12 shows nucleotide (SEQ ID NO: 36) and deduced amino acid (SEQ ID NO: 37) sequences of *M. bovis* RTXD (MbxD) gene.

FIG. 13 shows the alignment of the deduced amino acid sequence (SEQ ID NO: 37) of *M. bovis* RTXD (MbxD) gene and RTX toxins of *M. (Pasteurella) haemolytica* (LktD) gene (SEQ ID NO: 38), *A. pleuropneumoniae* (ApxIID) gene (SEQ ID NO: 39) and *E. coli* (HlyD) gene (SEQ ID NO: 40).

DEFINITIONS

Figure 1:
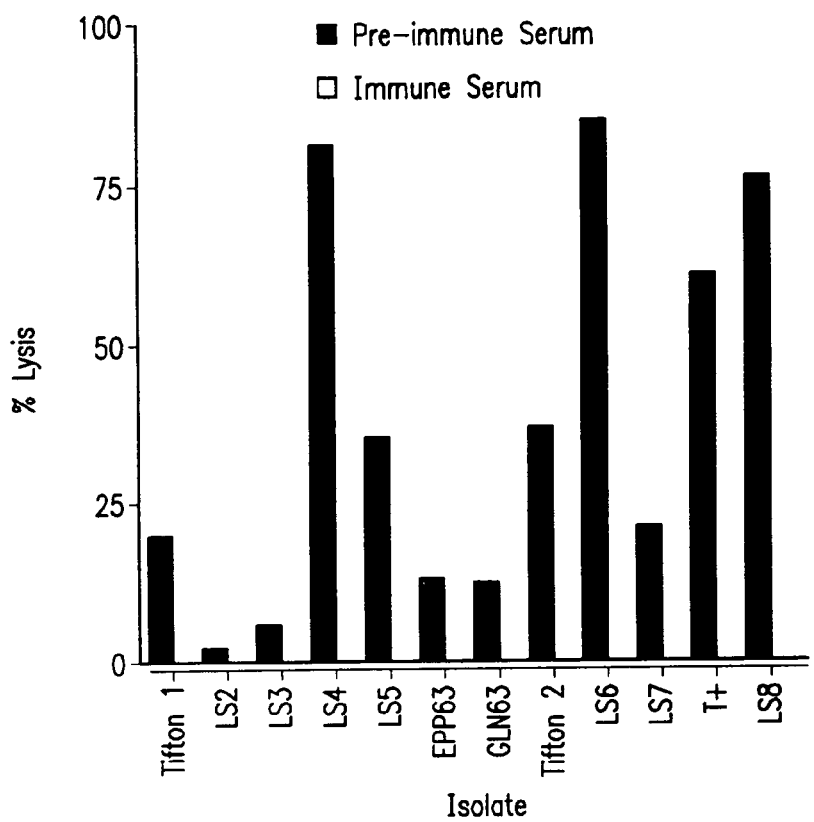
FIG. 1 is a graph illustrating neutralization of *M. bovis* leukotoxin in bacterial filter permeates by anti T+ serum.

As used herein:

"Cytotoxin," "cytolysin" or "hemolysin" means a protein produced by *Moraxella bovis* that is lytic for cells. The cytotoxin gene encodes 927 amino acids depicted by SEQ ID NO: 2 and is homologous to the internal regions of the published repeats in the structural toxin (RTX) toxins of *E. coli*, *M. (Pasteurella) haemolytica* and Actinobacillus species.

"Antigen" or "*M. bovis* antigen" means *M. bovis* cytotoxin as defined above.

"Functionality" or "functional characteristics" means the interaction of antibodies against *M. bovis* cytotoxin, such that the antibody inhibits the activity of *M. bovis* cytotoxin and retards/prevents development of IBK.

"ISCOM" means a partially purified cytotoxin formulated in an immunostimulating complex comprising *Quillaja saponins* (Quil A), cholesterol and phospholipids.

"IBK" means infectious bovine keratoconjunctivitis (pinkeye) caused by *Moraxella bovis*.

"*M. bovis*" or "*Moraxella bovis*" means the etiologic agent of IBK which expresses a cytotoxin that lyses corneal epithelial cells and neutrophils and results in corneal ulceration in cattle and calves. Pathogenic isolates of *M. bovis* are hemolytic; non-pathogenic isolates are nonhemolytic.

"mbxA" means a gene encoding *M. bovis* cytotoxin, said gene comprising a nucleotide sequence of 2784 base pairs depicted as SEQ ID NO: 1.

"MbxA" means a protein encoded by mbxA gene described as SEQ ID NO: 2.

"Leukotoxic" activity means biological activity which causes lysis of bovine neutrophils and lymphoma cells.

"Hemolytic" activity means biological activity which causes lysis of red blood cells.

"Corneotoxic" activity means biological activity which causes lysis of corneal epithelial cells.

"KDO" means 2-keto-3-deoxyoctonate.

"Antibodies" means proteins which structurally interact with the target antigen, i.e., *M. bovis* cytotoxin, and are produced when the antigen is introduced into an animal, such that they stimulate the immune system. The term also includes antibodies produced in vitro, such as recombinant antibodies, antibodies produced by hybridoma cell cultures and chimeric proteins, as well as hybridoma cells and chimeric constructs introduced into the host to provide an in vivo antibody.

"Antibodies to *M. bovis* antigen" means proteins which structurally interact with the target antigen and inhibit or detect infectious bovine keratoconjunctivitis.

"Monoclonal antibodies" means the monovalent antibodies produced by B cells fused to immortalized cells producing specific antibody to *M. bovis* antigen.

"Polyclonal antibodies" means antibodies directed at *M. bovis* antigen which are not monovalent and are the products of multiple B cells in character.

"*M. bovis* antigen DNA" means the sequence of about 2784 nucleotides identified as SEQ ID NO: 1 which encodes a protein comprising an amino acid sequence depicted by SEQ ID NO: 2.

"Vaccine" means a protein, recombinant protein, DNA, RNA, or a fragment thereof preserved from *M. bovis* cytotoxin which, upon administration to a host, is able to provoke an immune response including but not limited to the production of antibodies, cytokines and other cellular responses.

"Prevention or prophylaxis" means the passive or active immunization with antibodies or vaccines of the invention such that disease or infection does not occur.

"Treatment" means therapeutic use of any protein or antibody to inhibit existing infection in a cattle or calf host.

DETAILED DESCRIPTION OF THE INVENTION

This invention relates generally to infectious bovine keratoconjunctivitis, to vaccines, antibodies, purified or partially purified native or recombinant proteins, DNAs, RNAs and methods for prophylaxis and treatment of infectious bovine keratoconjunctivitis (IBK).

More specifically, the invention concerns identification, isolation, and purification or partial purification of native *M. bovis* antigen (cytotoxin) which causes IBK in cattle and calves, determination of its biological activity, identification and isolation of an *M. bovis* genes mbxA, mbxb, mbxC and mbxD, and determination of their nucleotide sequences, deducing their amino acid sequences based on the DNA sequences, partial sequencing of native partially purified cytotoxin, cloning of *M. bovis* genes mbxA, mbxb, mbxC and MbxD, expression of recombinant proteins, identification of the amino acid sequences of the expressed proteins and their purification, and preparation of *M. bovis* cytotoxin containing vaccines or polyclonal or monoclonal antibodies against such cytotoxin.

I. Native *Moraxella bovis* Cytotoxin

*Moraxella bovis* is a bacteria isolated from a cattle infected with *Moraxella bovis* and suffering from infectious bovine keratoconjunctivitis. *M. bovis* strains are pathogenic or nonpathogenic and different isolates may be found in different regions.

A. *M. bovis* Strains and Isolates

A cytolytic strain *M. bovis* (T+) and its noncytolytic subculture (T−), as well as cytolytic strains EPP63 and GLN63 were obtained from Dr. G. W. Pugh, Ames, Iowa. Additional isolates Tifton 1, Tifton 2, GA3, LS-2, LS-3, LS-4, LS-5, LS-6, LS-7 and LS-8 were obtained from field specimens submitted for determination of IBK infections from various states. The strains were isolated according to Example 1.

B. Characteristics of Native *M. bovis* Cytotoxin

*Moraxella bovis* produces a toxin, herein called cytotoxin, which causes cell lysis.

The cytotoxin of *Moraxella bovis* (M. bovis) is a transmembrane pore forming molecule that shares antigenic homology to the *E. coli* α-hemolysin, and is excreted in particulate complexes with the proteins during log phase growth. The cytotoxin has leukotoxic, corneotoxic, and hemolytic activities. Once released into the media, the liberated cytotoxin and protein aggregates can be separated from the whole bacteria by filtration through polycarbonate membranes of a mean pore diameter 0.22 µM, and can be retained by filters with molecular weight cut-offs that are >100 kDa.

Cytotoxin is an unstable molecule with activity dissipating rapidly after removal from the bacterial cell. Its pathogenic activity is irreversibly inactivated by a number of chemical, enzymatic, and physical treatments, including trypsin, sodium dodecyl sulfate, high incubation temperature (>37° C.), and calcium chelation.

The molecular complexity and the lability of the cell free cytotoxin has precluded purification to a monomolecular state.

C. Immunogenicity of *M. bovis* Strains

To investigate the immunogenic potential of cytotoxin, characterization of cytotoxin of *M. bovis* strains from diverse regions of the United States were undertaken.

For this purpose, leukotoxins were obtained from nine field strains and three isolates. These leukotoxins were submitted to neutralization assay as described in Example 21 with immune serum or pre-immune serum. Results are seen in FIG. 1.

FIG. 1 illustrates neutralization of *M. bovis* leukotoxin in bacterial filter permeates from isolates Tifton 1, Tifton 2, LS-2, LS-3, LS-4, LS-5, LS-6, LS-7, LS-8 and in three cytolytic strains T+, EPP63 and GLN63 with immune rabbit anti-T+ serum compared to neutralization of these permeates with pre-immune serum from the same rabbit. The pre-immune serum was used as the negative control. In this study, the same bacterial filter permeates were incubated with either the immune serum or pre-immune serum under the same conditions. The leukotoxic activity was measured by LDH assay.

As seen in FIG. 1, the undiluted anti-T+ diafiltered retentate serum inhibited the cytotoxic activity of all strains and isolates. No such inhibition was observed in samples incubated with pre-immune serum.

These results clearly confirm that the leukotoxic activity of cytotoxin is shared by *M. bovis* strains and isolates and suggest that a vaccine containing such cytotoxin would immunize the cattle against IBK.

II. Cytotoxin Gene, Protein, Recombinant Protein and DNA

Following the discovery and confirmation that the cytotoxin protein is an antigen which could be used as a vaccine for cross-strain protection against IBK, cloning, characterization and sequencing of the *M. bovis* cytotoxin genes, expression of the proteins encoded by these genes and the amino acid sequencing of HPLC purified peptides derived from native cytotoxin was undertaken.

A. Isolation of *M. bovis* Cytotoxin for Amino Acid Sequence Analysis

For amino acid sequence analysis, the *M. bovis* cytotoxin/cytotoxin peptides were partially purified by the procedure described in Example 14. To identify proteins that were unique to the hemolytic strain T+, purified culture extracts from hemolytic T+ and nonhemolytic T− *M. bovis* strains were compared by Western blotting using the procedure described in Example 15.

Figure 2:
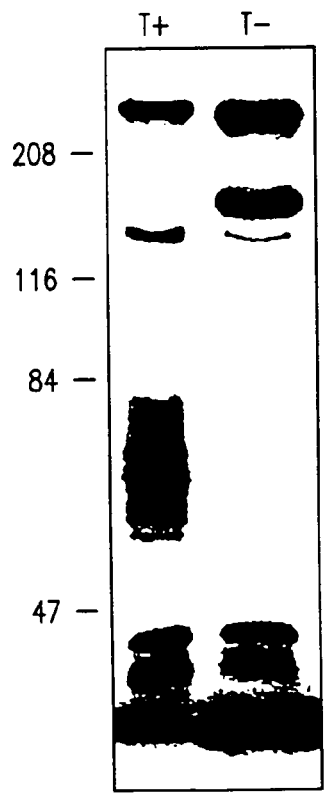
FIG. 2 is an autoradiogram of the pooled and concentrated void volume fraction of diafiltered retentate from T+ and T− cultures chromatographed on a Superose 6HR column.

Several candidate proteins for the *M. bovis* cytotoxin with molecular masses ranging from 55 to 75 kDa were identified as shown in FIG. 2.

FIG. 2 is the autoradiogram of the pooled and concentrated void volume fraction of diafiltered retentate from T+ and T− cultures chromatographed on a Superose 6 column.

The rabbit antiserum to column purified cytotoxin, in 1:400 dilution, was used as the primary antibody. Molecular mass markers 47, 84, 116 and 208 kDa are indicated. Protein bands in T+ lane ranging from 55 to 75 kDa were found to represent *M. bovis* cytotoxin protein/peptides that were unique to T+ diafiltered retentate. A 70 kDa protein in Superose 6 chromatographed T+ diafiltered retentate was subsequently identified on a Coomassie blue stained SDS polyacrylamide gel and was the source for two peptides designated peptides #23 and #26. These peptides were sequenced by N-terminal Edman degradation chemistry.

The respective amino acid sequences for two tryptic peptides #23 and #26 that were derived from the 70 kDa band were FLSELNKELEAE (SEQ ID NO: 6) and FNDIF-HSGEGDDLLDSGA (SEQ ID NO: 13).

BLAST database searches identified relatedness between the two peptides and the deduced amino acid sequences from RTX A genes of *E. coli*, *M. haemolytica*, *A. suis*, *A. pleuropneumoniae*, and *A. actinomycetemcomitans*. These alignments also predicted that peptide #23 was amino to peptide #26. Sequence and orientation-specific degenerate PCR primers 23A and 26A designed from reverse translating the amino acid sequences for peptides #23 and #26, respectively, amplified an approximately 850 bp fragment of genomic DNA from *M. bovis* Tifton I strain.

The deduced amino acid encoded by this region exhibited homology to the RTX family of bacterial exoproteins. Complete cloning and sequencing of mbxA was subsequently performed using a PCR based approach as described herein.

B. Homology with RTX Toxins

Amino acid sequencing of HPLC purified peptides derived from the purified cytotoxin protein has yielded amino acid sequences which show homology to internal regions of the published RTX toxins of *E. coli*, *M. haemolytica* and *Actinobacillus* spp. Regions of homology are seen in Table 4 and Table 5.

Table 5 shows amino acid sequence of *M. bovis* cytotoxin peptide peak #26 aligned with known published amino acid sequences of RTX toxins.

Obtained results show that a relationship exists between the *M. bovis* cytotoxin and the RTX family of toxins. These results are further supported by the earlier findings of other investigators that a monoclonal antibody to the RTX toxin of *E. coli*, namely alpha-hemolysin, recognized a protein in hemolytic and cytolytic extracts from hemolytic but not nonhemolytic *M. bovis* (*Vet. Microbiol.*, 43:183-196 (1995)).

C. Deduced Amino Acid Sequences

Amino acid sequences of products MbxA, MbxB, MbxC and MbxD of the four genes mbxA, mbxb, mbxC and mbxD were deduced. The peptide MbxA is the structural cytotoxin. Peptides MbxB, MbxC and MbxD are involved in *M. bovis* cytotoxin activity.

Specifically, MbxA peptide is encoded by the mbxA gene. DNA sequence of the mbxA gene was determined according to the Example 17. Plasmid DNA was isolated with Qiagen plasmid minipreps (Qiagen, Valencia, Calif.). The DNA sequence of the complete cytotoxin gene was obtained by sequencing PCR products directly or PCR products cloned into pCR2.1-TOPO (Invitrogen) with a TOPO TA cloning kit (Invitrogen). PCR primers C-down and B-up, corresponding to conserved regions within respective RTX C and B genes of other RTX toxin producing bacteria, were used for PCR amplification. These primers amplified a 4 kb region that contained an open reading frame (ORF) of 2784 nucleotide bases including stop codon depicted as sequence SEQ ID NO: 1, seen in FIG. 3. This gene was designated mbxA.

The MbxA protein encoded by mbxA gene was deduced to be 927 amino acids with a predicted molecular mass of 98.8 kDa (SEQ ID NO: 2).

TABLE 4

Amino Acid Alignment

| | | | | | | | | | | | | |
|---|---|---|---|---|---|---|---|---|---|---|---|---|
| *M. bovis* cytotoxin | F | L | S | E | L | N | K | E | L | E | A | E | SEQ ID NO: 6 |
| *M. haemolytica* leukotoxin | F | L | L | N | L | N | K | E | L | Q | A | E | SEQ ID NO: 7 |
| *E. coli* alpha hemolysin | I | L | S | Q | Y | N | K | E | Y | S | V | E | SEQ ID NO. 8 |
| *A. pleuropneumoniae* hemolysin | F | L | I | N | L | N | K | E | L | Q | A | E | SEQ ID NO: 9 |
| *A. pleuropneumoniae* hemolysin | L | L | S | Q | Y | N | K | E | Y | S | V | E | SEQ ID NO: 10 |
| *A. suis* cytotoxin | F | L | I | N | L | N | K | E | L | Q | A | E | SEQ ID NO: 11 |
| Consensus sequence | F | L | . | . | L/Y | N | K | E | L/Y | . | A/V | E | SEQ ID NO. 12 |

Table 4 shows amino acid sequence of *M. bovis* cytotoxin peptide #23 aligned with known published RTX toxin amino acid sequences.

There was approximately 40-50% identity between deduced amino acid sequences of mbxA and other RTXA genes. Specifically, there was 50.4% identity with *M.*

TABLE 5

Alignment of Fragment #26

| | | | | | | | | | | | | | |
|---|---|---|---|---|---|---|---|---|---|---|---|---|---|
| *M. bovis* cytotoxin | F | N | D | I | F | H | S | G | E | G | D | D | L | L | SEQ ID NO: 13 |
| *A. pleuropneumoniae* serotype 8 cytolysin | F | R | D | I | F | H | G | A | D | G | D | D | L | L | SEQ ID NO: 14 |
| *A. actinomycetemcomitans* leukotoxin | F | N | D | V | F | H | G | H | D | G | D | D | L | I | SEQ ID NO: 15 |
| *A. pleuropneumoniae* serotype 2 cytolysin | F | R | D | I | F | H | G | A | D | G | D | D | L | L | SEQ ID NO: 16 |
| Consensus sequence | F | . | D | . | F | H | G | A | D | G | D | D | | L/i | SEQ ID NO: 17 | haemolytica LktA, 49.1% with A. pleuropneumoniae ApxIIA, 48.7% with A. suis ClyIIA, 43.5% with E. Coli HlyA, and 40.9% with A. actinomycetemcomitans LtA. A sequence alignment of MbxA with LktA, ApxIIA, and HlyA is shown in FIG. 4.

FIG. 4 shows alignment of the deduced amino acid sequences of MbxA and RTX toxins of M. (Pasteurella) haemolytica (LktA), A. pleuropneumoniae (ApxIIA) and E.coli (HlyA). Black boxes indicate identical amino acids. Gray boxes indicate highly similar amino acids.

The location of peptides #23 and #26 derived from trypsin digestion of the 70 kDa protein are indicated except that the residue at position 720 was designated serine by N-terminal Edman degradation chemistry. The sequences corresponding to 6 glycine rich repeats are indicated on the top MbxA sequence by double lines. The expressed recombinant internal peptide corresponded to amino acid 438 through 713. The expressed recombinant carboxy peptide corresponded to amino acids 643 through 927. Lysines at positions 536 and 660 (marked by *) are hypothetical acylation modification sites as determined by relatedness of the neighboring amino acids to published consensus sequences (*Infect. Immun.*, 64:3081-7 (1996) and *Microbiol. Mol. Biol. Rev.*, 62:309-33 (1998)) surrounding modified lysine residues of HlyA.

MbxA protein has been found to have as much as 50% identity with other RTX toxins and this homology extends over the length of the protein. The carboxy terminus of MbxA features glycine rich repeats that are characteristic of RTX proteins. Specifically, there are six glycine-rich repeats in the carboxy terminal 325 amino acids of MbxA. Four of these exactly match the predicted L/V-X-G-G-X-G-N/D-D-X (SEQ ID NO: 29) consensus for glycine repeats in RTX toxins.

Figure 5:
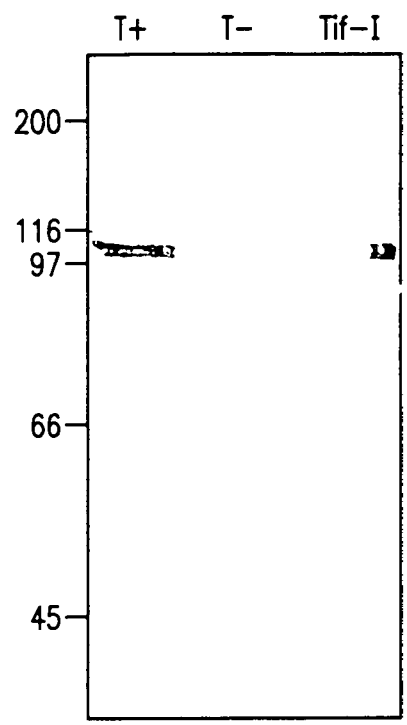
FIG. 5 is an autoradiogram demonstrating MbxA presence in culture supernatants of T+, and Tifton I and absence in T− culture supernatants.

Identification of MbxA protein in M. bovis in culture supernatants is illustrated in FIG. 5.

FIG. 5 is an autoradiogram demonstrating cytotoxin MbxA in culture supernatants of T+ and Tifton I. Three hour culture supernatants from T+, T− and Tifton I (Tif I) were electrophoresed on a 3.9%/7.5% SDS-polyacrylamide gel, and transblotted to Immobilon-P (Millipore) and probed with rabbit antisera against the expressed recombinant carboxy peptide (1:250 dilution). Molecular mass markers 45 kDa, 66 kDa, 97 kDa, 116 kDa and 200 kDa are indicated. Two proteins with molecular masses of 102 and 105 kDa were present in culture supernatants from both T+ and Tifton I. No immunoreactive proteins were present in the T− culture supernatant. These proteins were concluded to represent full length MbxA protein.

Figure 6:
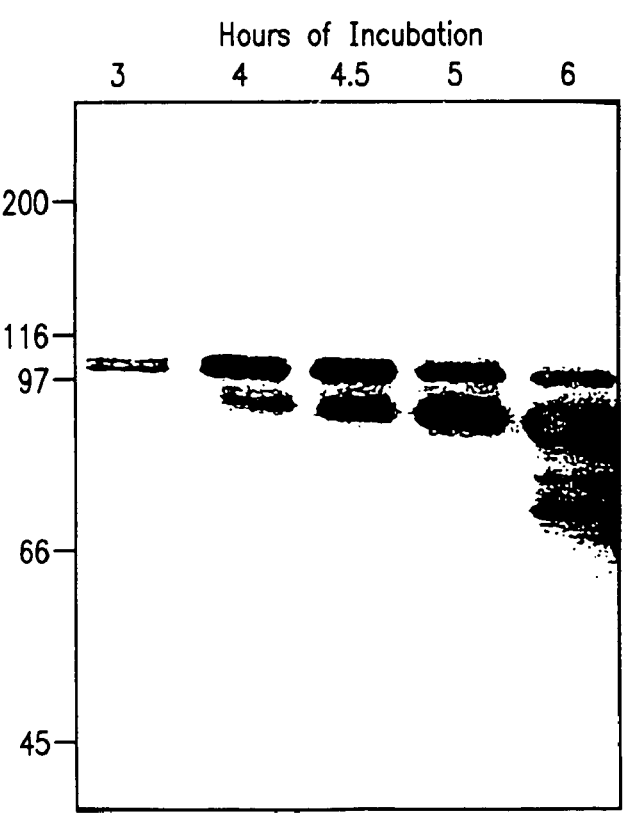
FIG. 6 is an autoradiogram of culture supernatants from a Tifton I broth culture at 3, 4, 4.5, 5 and 6 hours time points.

During longer incubations (4-6 hours), smaller immunoreactive proteins with molecular masses ranging from 52 to 91 kDa were identified in the culture supernatant as shown in FIG. 6.

FIG. 6 is an autoradiogram of culture supernatants from a Tifton I broth culture at 3, 4, 4.5, 5 and 6 hour time points. The blot was probed with rabbit antiserum against the expressed recombinant internal peptide encoded by MbxA gene (amino acids 438 through 713). Molecular mass markers 45, 66, 97, 116 and 200 kDa are indicated.

The appearance of proteins that were smaller than the 102 and 105 kDa predicted full length cytotoxin, following 4-6 hours of incubation, as seen in FIG. 6, has been attributed to proteolysis. Hemolytic M. bovis produces numerous hydrolytic enzymes including C4 esterase, C8 esterase-lipase, C14 lipase, phosphoamidase, phosphatase, leucine and valine aminopeptidases and gelatinase. Proteolysis is believed to account for the difference in mass between the 70 kDa protein selected for amino acid sequencing and the 98.8 kDa molecular mass predicted for full length MbxA. The data indicate that M. bovis could also express smaller molecular mass proteins that share epitopes with the internal region MbxA.

To confirm that MbxA encoded the M. bovis cytotoxin, neutralization assays were performed with antisera that was preabsorbed with the recombinant expressed carboxy terminus of MbxA (carboxy peptide). Results are seen in FIG. 7.

Figures 7A, 7B:
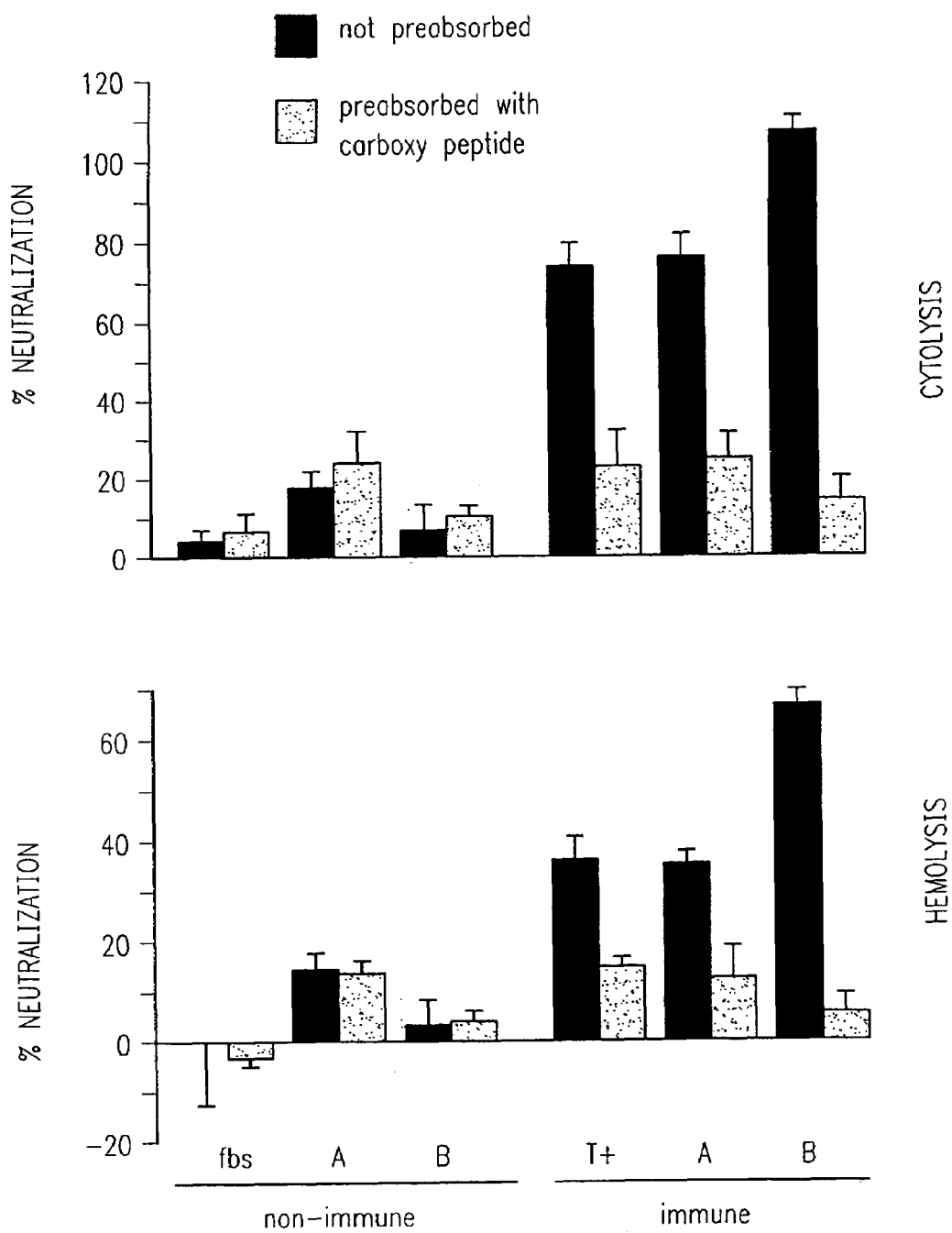
FIG. 7 shows the percent neutralization of cytolysis (FIG. 7A) and hemolysis (FIG. 7B) by non-immune and immune sera alone or preabsorbed with a recombinant expressed carboxy terminus of MbxA.

FIG. 7 shows percent neutralization (±1 standard deviation) of cytolysis (FIG. 7A) and hemolysis (FIG. 7B) by non-immune sera alone or preabsorbed with the carboxy peptide. Cytotoxin was tested for neutralization with non-immune fetal bovine serum (FBS); with preimmune sera A and B obtained from two rabbits A and B; with immune rabbit anti T+ sera obtained from T+ rabbit polyclonal antisera to culture filtrates from M. bovis strain T+; and with immune sera A and B obtained from rabbits A and B vaccinated with the carboxy peptide.

As seen in FIG. 7, rabbit anti T+ sera lost over 50% of its hemolytic and cytolytic neutralizing capacity following preabsorption with the carboxy peptide. Rabbit antisera against the carboxy peptide neutralized the hemolytic and cytolytic activity of native M. bovis cytotoxin. The neutralizing capacity of the sera designated A and B obtained from rabbit A and rabbit B was nearly equivalent to, or higher than the neutralizing capacity of the rabbit anti T+ antisera. Similar to rabbit anti T+ antisera preabsorbed with the carboxy peptide, rabbit A and B sera preabsorbed with the carboxy peptide lost over 60% of lysis neutralizing capacity relative to the unabsorbed samples.

The high percent neutralization of cytolysis for rabbit B serum occurred because the serum exhibited less cytolysis than the cytolysis negative control (TBS $CaCl_2$ buffer). The percent neutralization of hemolysis was <0 for fetal bovine serum because these samples exhibited more hemolysis than the hemolysis positive control (Tifton I diafiltered retentate +TBS $CaCl_2$ buffer). When incubated with indicator cells, the carboxy peptide alone was neither hemolytic nor cytolytic.

D. Cytotoxin Protein MbxA and other Proteins

Cytotoxin protein MbxA comprises 927 amino acids depicted as SEQ ID NO: 2. Amino acid SEQ ID NO: 2 comprises two peptides identified as peptide #23 and peptide #26.

Peptide #23 of MbxA cytotoxin is depicted by the amino acid sequence identified as SEQ ID NO: 6. The amino acid sequence of peptide #23 aligns with known published RTX amino acid sequences of M. haemolytica leukotoxin (SEQ ID NO: 7), E. coli alpha hemolysin (SEQ ID NO: 8), A. pleuropneumoniae hemolysin (SEQ ID NO: 9), A. pleuropneumoniae hemolysin (SEQ ID NO: 10), A. suis cytotoxin (SEQ ID NO: 11), as shown in Table 4 (supra), which also lists a consensus sequence identified as SEQ ID NO: 12.

Peptide #26 of MbxA cytotoxin is depicted by the amino acid sequence identified as SEQ ID NO: 13. The peptide #26 aligns with A. pleuropneumoniae serotype 8 cytolysin (SEQ ID NO: 14), A. actinomycetemcomitans leukotoxin (SEQ ID NO: 15) and A. pleuropneumoniae serotype 2 cytolysin (SEQ ID NO: 16), as seen in Table 5 (supra). Table 5 also lists a consensus sequence (SEQ ID NO: 17).

Additionally, the deduced amino acid sequences of products of *M. bovis* RTXB (MbxB), RTXC (MbxC) and RTXD (MbxD) genes were determined.

The deduced amino acid sequence of product of *M. bovis* RTXB gene(MbxB) is depicted by SEQ ID NO: 18. The MbxB protein encoded by mbxB gene was deduced to be 739 amino acids Amino acid sequence of the MbxB protein is seen in FIG. 8.

Deduced amino acid sequence MbxB aligned with other products of the RTXB genes, as seen in FIG. 9. FIG. 9 shows an alignment of *M. bovis* (MbxB) with the deduced amino acid sequences of RTXB genes from *M. (Pasteurella) haemolytica* (LktB) (SEQ ID NO: 19), *A. pleuropneumoniae* (ApxIB) (SEQ ID NO: 20) and *E. coli* (HlyB) (SEQ ID NO: 21). Black boxes in FIG. 9 indicate identical amino acids. Gray boxes indicate highly similar amino acids.

The deduced amino acid sequence of product of *M. bovis* RTXC gene (MbxC) is depicted by SEQ ID NO: 32. The MbxC protein encoded by mbxC gene was deduced to be 169 amino acids. Amino acid sequence of the MbxC protein is seen in FIG. 10.

Figure 11:
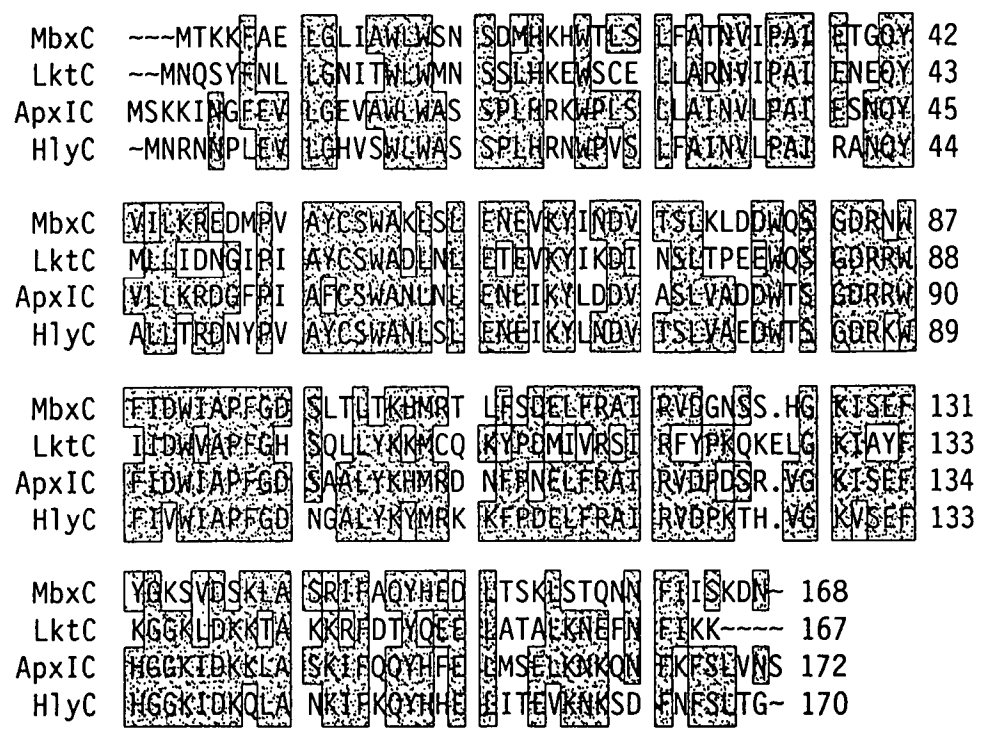

Deduced amino acid sequence MbxC aligned with other products of the RTXC genes, as seen in FIG. 10. FIG. 10 shows an alignment of *M. bovis* (MbxC) with the deduced amino acid sequences of RTXC genes from *M. (Pasteurella) haemolytica* (LktC) (SEQ ID NO: 33), A. pleuropneumoniae (ApxIC) (SEQ ID NO: 34) and *E. coli* (HlyC) (SEQ ID NO: 35), as seen in FIG. 11. Black boxes in FIG. 11 indicate identical amino acids. Gray boxes indicate highly similar amino acids.

The deduced amino acid sequence of MbxD protein encoded by the *M. bovis* RTXD gene (MbxD) is depicted by SEQ ID NO: 37. The MbxD protein encoded by mbxD gene was deduced to be 476 amino acids. Amino acid sequence of the MbxD protein is seen in FIG. 12.

Deduced amino acid sequence MbxD aligned with other products of the RTXD genes is seen in FIG. 13. FIG. 13 shows an alignment of *M. bovis* (MbxD) with the deduced amino acid sequences of RTXD genes from *M. (Pasteurella) haemolytica* (LktB) (SEQ ID NO: 38), *A. pleuropneumoniae* (ApxIB) (SEQ ID NO: 39) and *E. coil* (HlyB) (SEQ ID NO: 40). Black boxes in FIG. 13 indicate identical amino acids. Gray boxes indicate highly similar amino acids.

The above findings conclusively documents the presence of RTX gene (mbxA) and other RTX genes in *M. bovis*. The mbxA gene encodes a protein MbxA which has been found to be the etiologic agent of infectious bovine keratoconjunctivitis. The data also show that the protein expressed from this gene is responsible for the hemolytic and cytolytic activity present in culture extracts from pathogenic *M. bovis*, and thus proves that the *M. bovis* cytotoxin is an RTX toxin.

E. Cytotoxin Gene mbxA and mbxB, mbxc and mbxD Genes

Cytotoxin gene mbxA and othe RTX genes, namely mbxB, mbxC and mbxD belong to a family of RTX genes encoding bacterial pore-forming toxins. RTX genes are composed of four genes organized 5'-C-A-B-D-3'. The mbxC gene is located upstream of mbxA. The mbxB and mbxD are located downstream of mbxA.

The product of the RTXA gene is the structural toxin which is activated by the RTXC gene product to become hemolytic. Such activation is mediated by fatty acylation of conserved lysines. The activated toxin is secreted by membrane transport proteins encoded by RTXB and RTXD genes and a third protein TolC.

The cytotoxin gene mbxA, disclosed herein, has similar properties to other RTX genes and, as described above, its encoded protein MbxA has 50% identity with the deduced amino acid sequence of *M. haemolytica* leukotoxin. MbxA protein has 6 glycine-rich repeats in the carboxy terminus and two putative lysine acylation sites which are necessary for toxin activation.

RTX toxin gene mbxA was now shown to encode the *M. bovis* cytotoxin.

1. Structures of the mbxA, mbxB, mbxC and mbxD Genes

DNA sequence identified as SEQ ID NO: 1 represents the *M. bovis* RTXA gene mtxA. The nucleotide sequence of the mtxA gene is shown in FIG. 3. The gene mtxA comprises an ORF of 2784 nucleotides including stop codon.

The sequence of the cytotoxin gene was determined according to the procedure described in Example 18, using primers identified by the nucleotide sequences SEQ ID Nos: 23-26.

DNA sequence identified as SEQ ID NO: 30 represents the *M. bovis* RTXB gene mtxB. The nucleotide sequence of the mtxB gene is shown in FIG. 8. The gene mtxB comprises an ORF of 2215 nucleotides including stop codon.

DNA sequence identified as SEQ ID NO: 31 represents the *M. bovis* RTXC gene mtxC. The nucleotide sequence of the mtxC gene is shown in FIG. 10. The gene mtxC comprises an ORF of 507 nucleotides including stop codon.

DNA sequence identified as SEQ ID NO: 36 represents the *M. bovis* RTX D gene mtxD. The nucleotide sequence of the mtxD gene is shown in FIG. 12. The gene mtxD comprises an ORF of 1428 nucleotides including stop codon.

Corresponding protein products encoded by these genes are described above.

2. Cloning of mbxA, mbxb, mbxC and mbxD Genes and Expression of Recombinant Proteins In order to produce highly purified recombinant cytotoxin peptides, portions of the cytotoxin gene were cloned into expression vectors according to procedures described in Example 18. An internal peptide and carboxy peptide were expressed corresponding to amino acids 438 through 713 and 643 through 927, respectively.

3. Confirmation of Recombinant Protein Identity

Identity of produced recombinant protein was confirmed by neutralization studies, described in Example 21 and in FIG. 7.

Preparation of recombinant protein was done according to Example 18.

III. Biologically Derived or Recombinant Anti-*Moraxella bovis* Vaccines

A. Cytotoxin Vaccines

Vaccine is a biologically derived or recombinantly prepared agent useful for artificially acquired immunization in a host. The current invention describes the production of biologically derived and recombinant vaccines for active immunization of cattle and calves against IBK and includes the preparation of passive immune products for treatment of established infections.

The scope of the invention is, therefore, intended to include biologically derived or recombinantly prepared vaccines based on the antigens (a native or recombinant cytotoxin or a fragment thereof) of the invention.

The native vaccine is produced from isolated and partially purified native cytotoxin. The recombinant vaccine is produced by identifying the relevant cytotoxin or a fragment thereof, cloning them and expressing them using suitable vectors. This approach yields immunogens which are pure and reproducible in sufficiently large quantities to allow preparation of a vaccine for active immunization.

Recombinant vaccines are useful for immunization of the cattle or calves to produce the host's own antibodies against an *M. bovis* infection. Additionally, the recombinant vaccines may be used for production of passive immunotherapeutic agents.

These vaccines are also useful for primary protection against *M. bovis* infection in calves. Providing the herd with anti-*M. bovis* immunity decreases the risk for outbreaks of IBK in areas where the infection is prevalent.

In addition, mbxA DNA or RNA may be introduced into cattle so that propagation and/or expression of the encoded protein occurs in the host using a foreign expression system according to the methods known in the art.

The vaccine of the invention contains a cytotoxin identified by the invention, modified in such a way that it is incapable of producing the IBK symptoms but is capable of eliciting the production of specific protective antibodies against the disease when introduced in the body.

A DNA or RNA vaccine for prevention and treatment of infections caused by *M. bovis* is developed by utilizing newly identified and isolated DNA (SEQ ID NO: 1) and amino acid (SEQ ID NO: 2) sequences of the cytotoxin made by the *M. bovis* pathogen.

The antigen proteins used for preparation of vaccines correspond to cytotoxin or a cytotoxin fragment, which are identified by being a target of the polyclonal or monoclonal antibodies of the invention capable of preventing or ameliorating the disease.

A hybrid vector comprising a DNA segment that encodes the protein antigen able to bind selectively and specifically to anti-*M. bovis* antibodies operatively coupled to the vector can also be prepared and expressed. This includes preparation of recombinant vaccines using the viral expression vector outside of the host body and the preparation of DNA vaccines in procaryotic or eukaryotic hosts carrying the hybrid vector which may be introduced into the cattle or calf or a direct introduction of DNA or RNA into cattle or calf cells generating the host's own expression or translation of DNA or RNA, respectively, and production of proteins eliciting appropriate antibodies.

B. DNA and RNA Vaccines

DNA or RNA vaccines for immunization against *M. bovis* are prepared as described in *Science*, 259:1745 (1993), hereby incorporated by reference. DNA or RNA vaccines for development of immunity for cattle and calves against IBK are produced according to the methods described ibid.

Briefly, animals are injected, preferably intramuscularly, with DNA vectors encoding the deactivated anti-*M. bovis* antigen DNA or RNA and the antigen is produced. Th produced antigen elicits its own immune responses in the form of a formation of a specific antibody against anti-*M. bovis* antigen, thereby providing its own (native) immunity and/or cell mediated responses.

C. Field Trials with Vaccines

Both in vitro and in vivo studies were performed in order to determine whether the native or recombinantly produced cytotoxin can be used as agent for provoking active immunity against *M. bovis* and for preparation of vaccines.

As described above, antibodies to both native partially purified and recombinantly produced cytotoxins were tested for their cytolytic and/or hemolytic inhibitory activity in neutralization studies described in Examples 7-13, and both were shown to be inhibited with antibodies raised against native or recombinant protein. Both proteins also induced production of antibodies that recognize cytotoxin/cytotoxin peptides.

Field trials were performed for testing both the partially purified native and recombinantly produced cytotoxin.

1. Native Cytotoxin Vaccines

*M. bovis* cytotoxin is a labile protein of which activity rapidly disappears when removed from the bacterial cell. This property previously prevented its complete characterization. To overcome this, a method for partial purification and stabilization of cytotoxin was developed and such partially purified and stabilized cytotoxin was used for preparation of a vaccine for field trials.

In order to determine suitability of such partially purified native *M. bovis* antigen (cytotoxin) for vaccination against *M. bovis*, two field trials were performed where the cytotoxin was administered as a vaccine formulated according to Example 23.

The first field trial was performed on 82 cattle to determine the suitability of the cytotoxin in a vaccine to prevent IBK. In this trial the vaccine was a partially purified cytotoxin formulated either in Quil A adjuvant or in an immunostimulating complex (ISCOM), a matrix that is composed of Quillaja saponins (Quil A), cholesterol, phospholipids and the antigen of interest. ISCOM based vaccines utilizing antigens of Bovine Herpes Virus-1, Bovine Virus Diarrhea Virus and Bovine Leukemia Virus are known to be successful immunogens in cattle.

Prior to the field trial testing the *M. bovis* cytotoxin vaccine, a preliminary study had shown that calves vaccinated with a cytotoxin vaccine developed higher titre IgA concentrations than calves vaccinated with a cytotoxin in oil adjuvant. Results of the first field trial showed that calves receiving the cytotoxin vaccine had a significantly reduced requirement for treatment of IBK and had significantly reduced the severity of clinical IBK as compared to control calves.

To further evaluate the efficacy of an ISCOM vaccine using partially purified *M. bovis* cytotoxin, a second field trial was conducted according to Example 23.

Briefly, a group of 104 calves on a farm with a historically high (>50%) incidence of IBK were randomly assigned to receive one of three different vaccine compositions: A) saline (controls); B) ISCOM-cytotoxin; and C) ISCOM alone (adjuvant).

Calves were vaccinated on days 0 and 21. The individual responsible for all subsequent examinations of the calves was blinded as to treatment group assignments. The calves were then examined once weekly throughout the summer.

Figure 14:
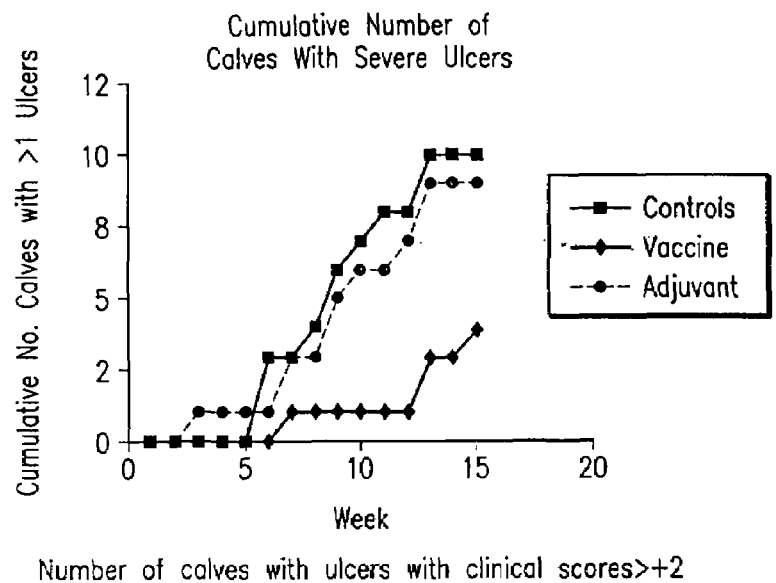
FIG. 14 is a graph showing the cumulative number of calves with ulcers in one eye vaccinated with *M. bovis* cytotoxin, adjuvant alone, or saline (control) over time.
Figure 15:
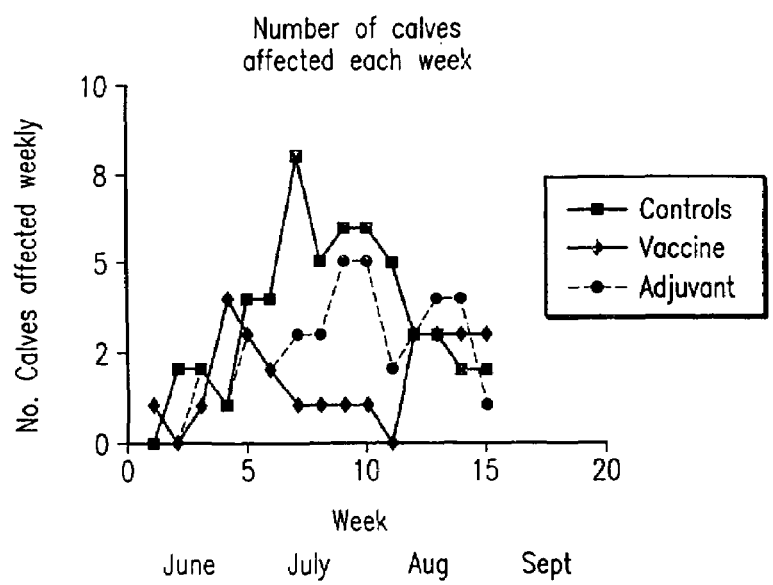
FIG. 15 is a graph showing a number of calves affected weekly in one group of vaccinated calves and in controls.

In the saline control group A, total of 18 of 34 calves developed IBK, while only 7 of 35 calves in the ISCOM-cytotoxin group developed IBK. Fifteen of 35 calves that received adjuvant alone developed IBK. The cumulative number of calves with ulcers in one eye over time is shown in FIG. 14. The cumulative number of calves that develop IBK was significantly less in the vaccinated group by the $10^{th}$ week and remained so until the end of the study. The number of calves with corneal ulcers during the study is presented in FIG. 15.

The cumulative number of vaccinated calves with severe corneal ulcers (ulcer score>1) was significantly lower in the antigen vaccinated calves than in the controls or in the adjuvant only group on observations. There were no differences in cumulative ulcers in calves of the control or the adjuvant only groups.

The surface area measurements and the clinical scores of the corneal ulcers are shown in Table 6.

TABLE 6

Surface Area Measurements of the Corneal Ulcers and Clinical Scores of Vaccinated Calves and Controls

| Group | Peak Surface area of First corneal ulcer | Surface area of corneal ulcer when first observed | Clinical score of corneal ulcer when first observed |
|---|---|---|---|
| Saline (n = 34) | 1.59 ± 4.0 (21.6)$^v$ | 0.714 ± 1.8 (11.5)$^v$ | 0.58 ± 0.7$^v$ |
| Vaccine (n = 35) | 1.00 ± 5.5 (31.2$^{a,s}$) | 0.082 ± 0.2 (9.2)$^{s,t}$ | 0.71 ± 0.8$^a$ |
| Adjuvant (n = 35) | 1.27 ± 2.9 (11.5)$^v$ | 1.23 ± 2.91 (1.1)$^v$ | 0.171 ± 0.4 |

The numbers reflect the mean value ± the standard deviation. Numbers in parenthesis reflect the range of values.

TABLE 7

Descriptive Data Regarding Recurrences, Treatment and Peak Corneal Ulcer Scores

| Group | No. Recurrences[a] | No. Calves treated | Peak CUS* |
|---|---|---|---|
| Saline (n = 34) | 5/18* | 10* | |
| Vaccine (n = 35) | 3/7 | 4 | |
| Adjuvant (n = 35) | 6/15 | 9 | |

*Differences were not significant (P > 0.05)

[a]Numbers reflect number affected divided by the number of calves with corneal ulcers.

The number of calves in the saline, vaccine and adjuvant groups that received antibiotic treatment, and the number of recurrences was not significantly different (Table 7).

Intact iscoms were present in low concentrations in indirectly stained ultracentrifuged sediments that were examined by electron microscopy.

Beginning on the 8$^{th}$ observation week, and continuing thereafter until the 15$^{th}$ observation week, there were significantly fewer cumulative infections in calves in the vaccine group than in either of the control groups (FIG. 14). There were no significant differences in numbers of cumulative infections between the calves that received adjuvant only and those of the controls.

TABLE 8

Cumulative Numbers of Calves with Corneal Ulcers at Each Observation

| Observation Week | Saline (n = 34) All | Saline ≧2 CUS | Vaccine (n = 35) All | Vaccine ≧2 CUS | Adjuvant (n = 35) All | Adjuvant ≧2 CUS |
|---|---|---|---|---|---|---|
| 0 | 0(0) | 0(0) | 0(0) | 0 | 0(0) | 0 |
| 1 | 0(0) | 0(0) | 0(0) | 0 | 0(0) | 0 |
| 2 | 0(0) | 0(0) | 1(2.9) | 0 | 0(0) | 0 |
| 3 | 1(2.9) | 0(0) | 1(2.9) | 0 | 1(2.9) | 1 |
| 4 | 1(2.9) | 0(0) | 1(2.9) | 0 | 3(8.6) | 1 |
| 5 | 2(5.9) | 0(0) | 4(11.4) | 0 | 3(8.6) | 1 |
| 6 | 3(8.8) | 0(0) | 4(11.4) | 0 | 5(14.3) | 1 |
| 7 | 5(14.7) | 3(8.8) | 4(11.4) | 0 | 5(14.3) | 1 |
| 8 | 7(20.6) | 3(8.8) | 4(11.4) | 1 | 7(20.0) | 3 |
| 9 | 9(26.5) | 4(11.7) | 4(11.4) | 1 | 8(22.9) | 3 |
| 10 | 12(35.3) | 6(17.6) | 4(11.4) | 1 | 11(31.4) | 5 |
| 11 | 13(38.2) | 7(20.6) | 4(11.4) | 1 | 11(31.4) | 6 |
| 12 | 13(38.2) | 7(20.6) | 4(11.4) | 1 | 12(31.4) | 7 |
| 13 | 14(41.1) | 8(23.5) | 5(14.3) | 1 | 14(34.3) | 7 |
| 14 | 15(44.1) | 8(23.5) | 5(14.3) | 3 | 15(40.0) | 7 |
| 15 | 16(47.1) | 10(29.4) | 5(14.3) | 3 | 15(42.9) | 9 |
| 16 | 18(52.9) | 10(29.4) | 7(20.0) | 4 | 15(42.9) | 9 |

The native vaccine was found to be effective at preventing new cases of IBK and the vaccine afforded protection against natural exposure. The antigenic mass of this experimental vaccine was concentrated from 5 liters of supernatant from hemolytic, toxigenic *M. bovis*. The retentate of that process was diafiltered extensively, effectively removing any solubilized protein with a molecular mass <100,000 daltons. A companion study showed that the leukotoxin was concentrated and stabilized in the diafiltered retentate. This proved to be antigenic and immunogenic in the field study described herein.

As measured by decreased cumulative infection, and decreased numbers of affected calves, vaccination with the vaccine derived from cytotoxin induced a resistance to infection under field conditions.

Results from this and previous studies provided a rational basis for pursuing the development of the vaccine comprising the native cytotoxin. Unfortunately, the lability of the cytotoxin and the difficulty associated with purifying it in milligram quantities limited its usefulness for practical use. To overcome these obstacles, techniques of molecular cloning and biotechnology to study the *M. bovis* cytotoxin were undertaken as described above and in Examples and the recombinant protein was used for preparation of recombinant vaccines.

2. Recombinant Vaccines

Recombinantly prepared cytotoxin was used for preparation of recombinant anti-*M. bovis* vaccine using procedure as described in Example 24.

For the preparation of vaccine, the *M. bovis* cytotoxin was expressed as described in Example 24, and expressed purified protein was mixed with the ISCOM following ISCOM matrix formation. The vaccine was prepared according to Example 24.

For vaccine production, ISCOM matrix preparation was mixed 1:1 (v/v) with the recombinant protein solution. Vaccine (2 ml) was used for primary vaccination and for follow-up booster inoculations. ISCOM marix adjuvant was used for control.

To determine if recombinantly derived *M. bovis* RTX toxin vaccine could prevent IBK, a vaccine trial was conducted during summer. In this trial, beef calves were randomly divided to receive saline, adjuvant alone (ISCOM matrix), or a recombinant *M. bovis* RTX toxin subunit vaccine. Vaccines were administered subcutaneously and calves were boostered 21 days later. The recombinant toxin vaccine contained the carboxy terminal 338 amino acids of MbxA. The calves were examined once per week for IBK through mid-September. Results indicated that fewer cases of IBK occurred in the recombinant vaccine group.

Figure 16:
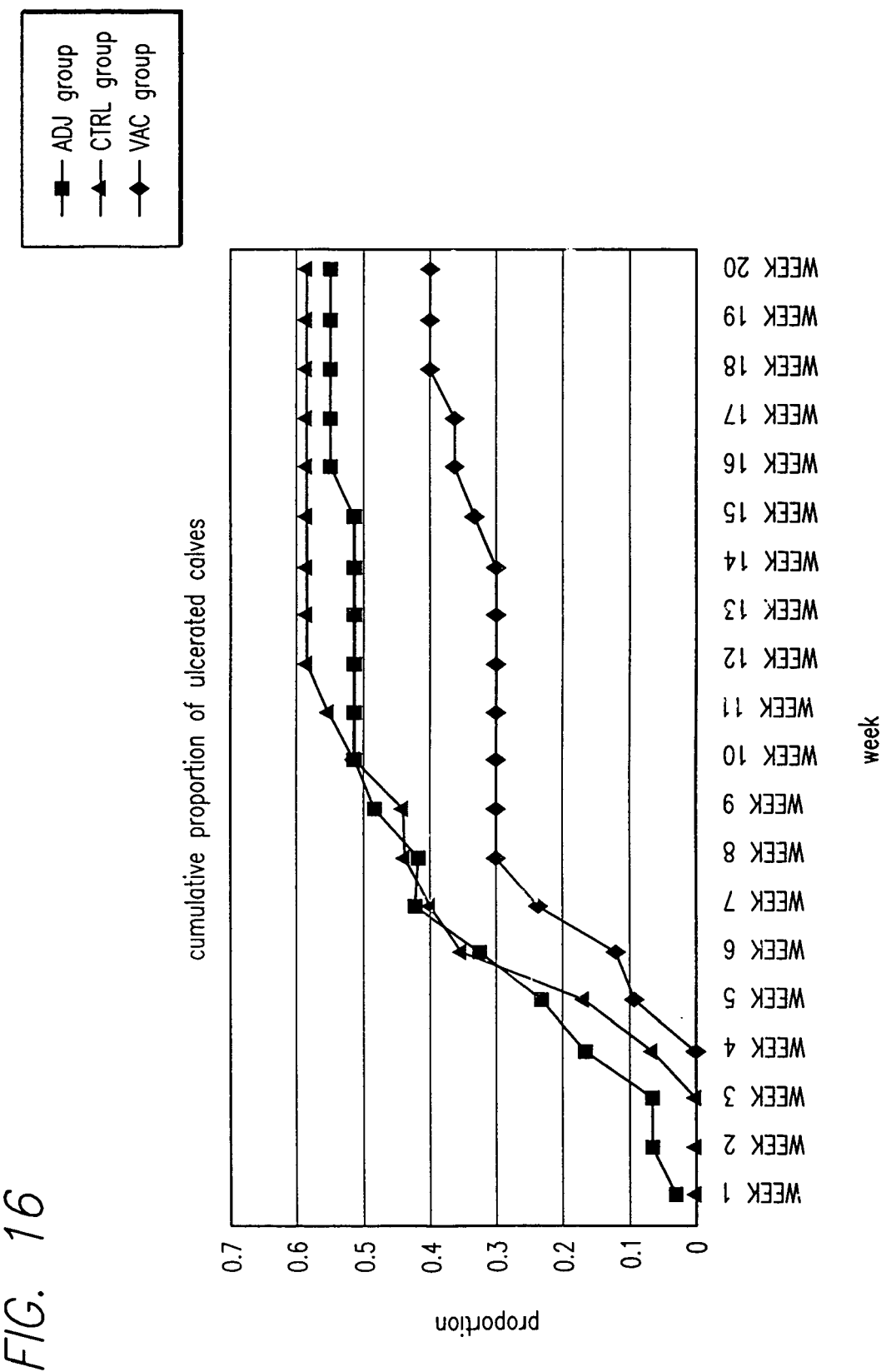
FIG. 16 is a graph showing cumulative proportion of ulcerated calves during the trial with recombinant cytotoxin vaccine, saline alone or adjuvant alone.

A. total of 93 calves were enrolled in the study. Respective calf numbers in each vaccine group were: 29 CTRL (saline control); 31 ADJ (ISCOM MATRIX contact); and 33 VAC (ISCOM matrix plus recombinant protein). At the end of the 20 week trial, a total of 47 calves developed corneal ulcers (50.5%). Respective numbers of ulcerated calves were 17 (54.8%), 17 (58.6%), and 13 (39.4%) for the CTRL, ADJ, and VAC groups. FIG. 16 shows the cumulative proportion of calves with ulcers at each weekly interval. During weeks 4 and weeks 11 through 15, there were significantly fewer ulcerated calves in the VAC group relative to the CTRL group. At week 4, there were significantly fewer ulcerated calves in the VAC group relative to the ADJ group.

Results of this field trial clearly show that the vaccine comprising recombinantly derived cytotoxin provided immunity against *M. bovis* in vaccinated animals.

Prophvlaxis of IBK with Antigen Vaccine

Using vaccines described above comprising either the purified native or recombinantly prepared cytotoxin antigen, the cattle and/or calves are vaccinated using a regimen typically utilized for immunization by vaccinating the animals at least twice in about a 3 week interval and with a booster vaccine at least once a year.

A method of prophylaxis of *M. bovis* infection comprises administering to the animal in need of such treatment a vaccine comprising the cytotoxin or recombinant cytotoxin of this invention capable of endogenous development of an inhibitory amount of anti-*M. bovis* antibodies.

V. Diagnostic Utilities

Cytotoxin of the invention and/or antibodies against *M. bovis* may also be used for diagnostic purposes, such as for detection of *M. bovis* carrier cattle.

In the simplest form, serum obtained from the cattle is reacted with monoclonal or polyclonal antibody raised against native or recombinant *M. bovis* cytotoxin. The antibody binding or forming complex with the antigen indicates the presence of antigen. Following techniques may be advantageously used for *M. bovis* antigen identification.

Antigen capture ELISA is a technique for identifying an antigen in a sample. In the case of *M. bovis* detection, it can be used to identify cytotoxin in tear samples from cattle or respiratory or vaginal secretions to identify carrier cattle. The technique utilizes an antibody directed against the antigen (cytotoxin)) which is fixed on a solid support.

It then uses traditional ELISA techniques to develop a color change indicative of cytotoxin presence. Diagnostic PCR utilizes primers, in this case, primers suitable for cytotoxin gene sequence, to amplify DNA from tissue samples, such as ocular, respiratory, or vaginal secretions, for example.

Fluorescence Resonance Energy Transfer (FRET) technology is also suitable to diagnose *M. bovis* carriers. This technology utilizes PCR primers linked to chemicals that fluoresce under certain conditions. If these primers detect the mbxA gene in sample DNA or bacteria, they emit certain detectable fluorescent spectra.

Method of diagnosing cattle that are carriers of *M. bovis* by use of antibodies (monoclonal or polyclonal) using an antigen capture ELISA.

Method to diagnose infection with hemolytic *M. bovis* utilizes diagnostic PCR of using DNA sequence data.

UTILITY

The current invention provides native or recombinant vaccines for immunoprotection against *M. bovis* infections and development of IBK in cattle and calves and methods for detection of latent *Moraxella bovis* infections.

EXAMPLE 1

Isolation of *Moraxella bovis* Bacteria

This example describes isolation of a cytolytic strain of *Moraxella bovis* T+ and a noncytolytic subculture T−.

A hemolytic, pathogenic strain of *Moraxella bovis* (T+) was isolated from a beef cow with infectious bovine keratoconjunctivitis. Cytolytic EPP and GLN 63 strains were furnished by Dr. G. W. Pugh (Ames, Iowa), and additional isolates were obtained from field specimens that were submitted to the laboratory for confirmation of bacterial identification. These additional isolates were recovered from clinically affected cattle located in regions of the United States that included southern Georgia (Tifton 1, Tifton 2), northern Georgia (GA 3), northern California (LS-2, LS-4, LS-6), southern California (LS-3, LS-8), Washington (LS-5), and North Carolina (LS-7). Isolate were identified and propagated as described in *Acta Path. Microbiol. Scand.*, 80B, 629-640 (1972) and in *Identification of Non-Enteric Gram-Negative Bacteria*, US Dept. Health Education and Welfare Technical Report, Center for Disease Control, Atlanta, Ga. (1979).

EXAMPLE 2

Purification and Concentration of the Cytotoxin

This example describes the procedure used for purification and concentration of the cytotoxin when produced in *M. bovis* shaker cultures.

The cytotoxin was produced in broth shaker cultures that were inoculated with lawn cultures of *M. bovis*. The inoculum was harvested from the surface of 10, 20 hour sheep blood agar plate lawns of *M. bovis* with sterile cotton tipped applicators. The bacteria on the swab were suspended into 10 ml of heart infusion broth (Difco Laboratories, Detroit, Mich.) spiked with 1.5 mM $CaCl_2$.

Flasks were inoculated with the suspension, and were incubated at 35.5±0.5° C. on a rotary shaker set at 200 oscillations per minute. The cultures were removed from the incubator when the optical densities (420 nM) reached 1.85. For purification, the cultures (living whole cells) were centrifuged for one hour at 13,000×g (4° C.) and the supernatants (centrifuged supernatants) were filtered through a sterile 0.2 µm polyethersulfone membrane (Gelman Sciences, Ann Arbor, Mich.).

Permeates from these filtrations (bacterial filter permeate) were concentrated approximately 100 fold by ultrafiltration, and further purified by diafiltration (diafiltered retentate) against 45 volumes of chilled (4° C.) buffer consisting of 50 mM Tris (pH 8.2), 500 mM sodium acetate, 1.5 mM $CaCl_2$ and 20% glycerol. Diafiltration was discontinued after the optical density (280 nm) of the diafiltered permeate reached ≦0.01. Specimens collected at each stage of preparation were examined for hemolytic and leukotoxic activities.

Filters that were used for concentration and diafiltration, included cartridges of spiral wrapped, regenerated cellulose (100 kDa molecular weight cut-off, CH2PRS® system S1Y100 membrane, Amicon, Beverly, Mass.), and flat polyethersulfone membranes (300, or 500 kDa molecular weight cut-off, stirred cell, XM 300 or YM 500 membranes, Amicon).

Results indicated that there were no differences in the retention of the cytotoxin by the filters, but because of ease of use, and capacity, most studies were performed using the regenerated cellulose filter. Each filtration step was conducted according to the manufacturer's recommendations, which included 30 PSI operating pressure, 300 to 500 ml/minute flow rate, and a 5 to 10 PSI pressure differential.

Due to the length of time required for diafiltration, initial measurements of cytolytic activity did not commence until 16 to 20 hours after the broth cultures were first centrifuged. For stability studies, cytolytic activities of the refrigerated retentates and permeates were centrifuged. For stability studies, cytolytic activities of the refrigerated retentates and permeates were re-examined 7, 14, and 57 days later. Cytolytic activities of frozen (−70° C.) samples were remeasured after 120 days. All measurements were made from at least duplicate experiments.

EXAMPLE 3

Cytotoxin Preparation for Neutralization Studies

This example describes the procedure used for preparation of cytotoxin for neutralization studies.

*Moraxella bovis* lawns were grown on trypticase soy agar plates supplemented with 5% sheep blood. After 24 hours of incubation, the bacterial cells were harvested by flooding the plate with 10 ml of Tris buffered saline solution (TBS $CaCl_2$ 50 mM Tris, 150 mM NaCl, 1.5 mM $CaCl_2$, pH 8.0), and suspending the bacterial growth with a sterile inoculating loop. The suspensions were collected from the surface of the agar, and then were centrifuged at 27,000×G for one hour. After centrifugation, the supernatants were harvested, filtered through 0.22 µM polyethersulfone membrane (Gelman Biosciences, Ann Arbor, Mich.), and tested for cytolytic activity.

EXAMPLE 4

Cytotoxicity Assay Using $^{51}$Cr-Labeled Cells

This example describes the assay for determination of cytotoxicity, using cells labeled with $^{51}$chromium.

A stable, tissue culture adapted cell line of bovine lymphocytes BL-3 cells, supplied by Dr. Gordon Thielen, University of California, Davis, were used as targets in the cytotoxicity assays. The cells were grown from frozen seed cultures at 37° C. in 5% $CO_2$ in Liebovitz L-15 and Minimal Essential Media (1:1; v/v) with penicillin (100 IU/ml), streptomycin (100 µg/ml), and 15% fetal bovine serum until sufficient density was achieved (3 to 4 days). The cells were harvested by centrifugation, and the pellets were washed 3 times in Dulbecco's phosphate buffered saline solution (DPBS). After the wash, the cells were resuspended in DPBS to a final concentration of $2\times10^7$/ml, labeled with 200 µCi of $^{51}$Cr (1 hr, 37° C.), and then washed three times in McCoys 5A buffer (Gibco/BRL, Grand Island, N.Y.). After the final wash, the cells were diluted to a final concentration of $1\times10^6$/ml in McCoys 5A buffer.

For measurement of cytotoxicity, 500 µl of labeled BL-3 cells were added to 500 µl of sample and incubated for one hour at 37° C. After incubation, the cells were centrifuged and the radioactivity was measured in 500 µl of supernatant. Labeled cells (500 µl) in 500 µl of labeled cells lysed with Triton X-100 (Sigma, St. Louis, Mo.) served as respective negative and positive controls. The % lysis was calculated using the formula:

$$\% \text{ lysis} = \left[ \frac{\text{counts per minute } (CPM) \text{ of specimen} - \text{media } CPM}{\text{Triton X } CPT - \text{media } CPM} \right] \times 100$$

For calculations relating to specific activity, a unit of cytotoxic activity was defined as the amount of leukotoxin required to release 1% of the total amount of $^{51}$Cr from the labeled BL-3 cells.

EXAMPLE 5

Cytotolytic Assay Using Non-Labeled Target Cells

This example describes the assay for determination of cytotoxicity using non-labeled target cells.

Cytolytic activity for bovine lymphocytes was also measured by assaying the release of lactate dehydrogenase (LDH). These tests were performed by washing BL-3 cells three times a diluting them to a final concentration of $5\times10^6$ cells/ml in DPBS, adding 100 µl of BL-3 cells to 100 µl of sample in 96-well polypropylene plates (Becton Dickinson, Franklin Lakes, N.J.) and incubating the mix for 60 minutes (37° C.) while being shaken for 30 seconds every 15 minutes. Duplicate measurements were made on each specimen.

After the incubation was completed, a 50 µl aliquot of supernatant from each well was transferred to a corresponding well in a new polystyrene plate (Costar, Cambridge, Mass.), and 75 µl of 0.75 mM β-NADH in 100 mM potassium phosphate pH 7.2 was added. The change in absorbance (340 µm) was measured every 15 seconds using an automated reader.

After 50 measurements, lactate dehydrogenase activity was recorded in units/ml with units representing the reciprocal slope of a line plate of ΔA/ΔT. For validation, lytic activities of 0.22 µM filter sterilized culture supernatants were measured concurrently using $^{51}$Cr release and LDH assays.

EXAMPLE 6

Neutralization Assay Using $^{51}$Cr Labeled Cells

This example describes the assay used for neutralization with $^{51}$chromium-labeled cells.

Prior to neutralization, sera were diluted 1:5 or 1:10 in TBS CaCl$_2$ or McCoys 5A buffer and 200 µl was mixed with 500 µl of specimen, refrigerated (4° C.) for one hour, and then mixed with 500 µl of labeled BL-3 cells. The cells and sera were incubated (37° C.) and rotated at 15 revolutions per minute for one hour before centrifuging each specimen and measuring the radioactivity in 500 µl of supernatant. For controls, dilutions of irrelevant rabbit sera, or fetal bovine serum was substituted.

EXAMPLE 7

Neutralization Assay Using Non-Labeled Target Cells

This example describes the assay used for neutralization with non-labeled target cells.

Cytolytic and hemolytic bacterial filter permeates were prepared by flooding agar lawn cultures of *M. bovis* with 10 ml of TBS CaCl$_2$, centrifuging the suspension and filtering the supernatants through sterile polyethersulfone membranes (0.2 µm average pore diameter). Heat inactivated sera were diluted in TBS $CaCl_2$. Aliquots (50 μl) of the bacterial filter permeates from T+ and T− were mixed with 50 μl of each serum dilution, and the mixture was refrigerated (4° C.) for 60 minutes before the addition of 100 μl of diluted BL-3 cells. The cell-serum mixture was further incubated (37° C.) for 60 minutes with gentle agitation for 30 seconds every 15 minutes. After incubation, 50 μl of the mixture was transferred to a new tissue culture plate to measure the cell free LDH activity.

EXAMPLE 8

Hemolysin Assay

This example describes conditions used for the hemolysin assay.

Bovine erythrocytes, harvested from 10 ml of heparinized blood of a normal cow, were packed by centrifugation and washed three times with TBS $CaCl_2$ buffer. For the hemolysin assay, 10 μl of packed erythrocytes were added to 500 μl of sera of 10-fold dilutions of sample. The mixtures were incubated for 6 hours (37° C.) before final evaluation of hemolytic activity. Controls included washed erythrocytes in TBS $CaCl_2$ incubated with, or without 10% Triton X as respective positive and negative controls. For measurement of hemolytic activity of column fractions, a mixture of 10 μl of packed, washed bovine erythrocytes and 500 μl of sample, was incubated for 6 hours (37° C.). After incubation, the cells were centrifuged, and the absorbance (455 μM) of the supernatant was measured. Units of hemolytic activity were calculated using the formula:

$$\text{Hemolytic units} = \frac{\text{Sample } O.D. - \text{Neg. Control } O.D.}{100\% \text{ Lysis } O.D. - \text{Neg. Control } O.D.} \times 100\%$$

Percent hemolysis was calculated from hemolytic units of 100% lysis controls, and the specimen.

EXAMPLE 9

Immunoassay

This example describes conditions used for immunoassay.

The 96-well polystyrene plates (Nunc Maxisorp, Naperville, Ill.) were sensitized with 100 μl of solution containing 2 μg/ml diafiltered cytotoxin, refrigerated for 24 hour, and then washed with TBS $CaCl_2$ containing 0.05% Tween 20 (TBST). After washing, two-fold doubling dilutions of serum were added to the wells. The plate was then agitated gently for 60 minutes at 37° C., and washed three times with TBST. After the final wash, either goat anti rabbit or rabbit anti bovine IgG labeled with 100 μl of alkaline phosphatase (Jackson Immunobiological, West Grove, Pa.), diluted 1:25,000 in TBS $CaCl_2$, was added. Plates containing secondary antibodies were shaken continuously for 60 minutes (37° C.), and then washed one more time with TBST. The color reaction was developed by the addition of 100 μl of 3.8 mM p-nitro phenyl phosphate (disodium salt) dissolved in a buffer consisting of 0.5 MM $MgCl_2$ and 50 mM $Na_2CO_3$ (pH 9.5). The plate was agitated gently for 60 minutes at 37° C. and then absorbance (400 μm) was measured using an automated plate reader (Dynatech MR700, Chantilly, Va.).

EXAMPLE 10

Chromatography of Diafiltered Retentates

This example describes conditions used for chromatography diafiltered retentates.

Diafiltered retentates of T+ and T− were chromatographed through a 10×300 mm Superose 6HR gel filtration column (FPLC, Pharmacia Biotech, Uppsala, Sweden) that was equilibrated with 50 mM Tris, 0.5 M sodium acetate, 1.5 mM $CaCl_2$ pH 8.0. The column was loaded with 200 μl of diafiltered retentate and was eluted with buffer at a maximum flow rate of 0.5 $ml/min^{-1}$. Absorbance (280 nm) of column effluent was measured. Fractions (3.5 ml) were collected, and examined for cytotoxic and hemolytic activity, and for endotoxin content.

EXAMPLE 11

Production of Antibodies

This example describes procedure used for the production of antibodies against *M. bovis* cytotoxin.

New Zealand White rabbits were given 0.5 ml of either diafiltered retentate (50 μg protein), gel filtration purified cytotoxin (10 μg protein) or permeates from the 0.22 μM filtration of T+ or T− broth cultures.

Immunizing preparations were mixed 1:1 (v/v) in Freunds complete adjuvant for the primary injection and with incomplete Freunds adjuvant for the booster, 21 days later. The rabbits were exsanguinated three weeks after the booster was given. Convalescent serum from a Holstein calf with clinically apparent infectious bovine keratoconjunctivitis and fetal bovine serum (Hyclone Laboratories, Logan, Utah) were used as respective positive and negative controls.

EXAMPLE 12

General Methods

This example describes or gives reference to general methods used in these studies.

Measurement of 2-Keto-3-Deoxvoctonate (KDO)

The concentration of KDO was measured in diafiltrates, and cytolytic Superose 6HR column fractions using a hydroperiodate oxidation assay as described in *Handbook of Micromethods for the Biological Sciences*, Van Nostrand Reinhold, N.Y. (1976).

Measurement of Endotoxin

The concentration of endotoxin in cytolytic Superose 6HR column fractions was measured semiquantitatively using a commercially available timed gel formation limulin assay (Sigma, St. Louis, Mo.).

Electrophoresis

Proteins were examined using the discontinuous polyacrylamide gel electrophoresis method described in *Nature*, 227:680-685 (1970).

To reduce non-specific binding, blots were blocked in a buffer containing 0.1% SDS, 50 mM Tris and 150 mM NaCl, pH 7.5, containing either 1.5% goat serum, or 0.5% teleost gelatin (Sigma Inc., St. Louis, Mo.). The blocked, washed membranes were incubated with antiserum for 12 hours, and then were washed four times in TBS. After the final wash, blots were incubated with either 1:2500 dilution of goat anti-rabbit immunoglobulin conjugated with alkaline phosphatase, or with 0.5 µCi of $I^{125}$ labeled protein A in TBS. The alkaline phosphatase labeled blots were incubated for 12 hours, after which they were washed four times (10 minutes per wash) with a buffer containing 100 mM Tris, 5 mM Tris, 5 mM $MgCl_2$ and 100 µM NaCl (pH 9.5). After the final wash, the blots were developed using nitro blue tetrazolium and bromo-chloro-indonyl-phosphate as described in *Antibodies: A Laboratory Manual*, $1^{st}$ Ed., Cold Spring Harbor, Cold Spring Harbor Laboratories, New York (1988). The A-$I^{125}$ protein A-$I^{125}$ labeled blots were incubated for 2 hours, and then washed 3 times, 4 hours per wash, in TBS containing either 1.5% goat serum or 0.5% teleost gelatin. After washing, the blots were air dried and autoradiographed.

Protein Quantitation

Protein concentrations were measured using the Lowry protein precipitation method (Protein Assay Kit, Sigma Inc., St. Louis, Mo.).

EXAMPLE 13

Corneal Epithelial Cell Cultures

This example describes procedures used for culturing corneal epithelial cells.

Bovine eyes were collected at slaughter, and the corneal epithelium was harvested by keratectomy. An ophthalmic solution containing neomycin, polymyxin B and gramicidin (Schein Pharmaceuticals, Port Washing, N.Y.) was applied to the corneas prior to keratectomy in order to reduce the bacterial contamination.

The corneal epithelium was dissected from the stroma, and immersed in 50 ml of Minimal Essential Medium (MEM) containing D-valine, penicillin G (100 IV/ml), streptomycin (100 µg/ml), gentamicin sulfate (100 µg/ml), and amphotericin B, (250 µg/ml). Neutral protease, (Dispase II, Boehringer Mannheim, Indianapolis, Inc.) was added in order to initiate separation of the epithelial cells from the remaining stroma.

After 2 hours of incubation, the epithelial sheets were washed three times in fresh media, and were placed epithelial side down, in wells of sterile polystyrene plate. The cultures were then immersed in 2 ml of media containing MEM-D-valine and 10% fetal bovine serum, and incubated in an atmosphere of 5% $CO_2$ (37° C.) until plaques of adherent corneal cells were observed on the bottom of the plate. The epithelial sheets were removed from the plates at that time. These cell cultures were incubated for at least 48 additional hours until they formed an adherent monolayer.

In order to verify the epithelial origin of the adherent cells, sample monolayers were stained with an anti-keratin, epithelium specific monoclonal antibody furnished by Dr. Rheen Wu, University of California, Davis. After 1 hour, the cultures were washed with PBS containing 0.05% Tween 20, and a fluorescein isothiocyanate labeled goat anti-mouse antibody (Organon Teknika, Durham, N.C.) was applied for 1 hour. The unbound secondary antibody was then washed from the cells using PBS with 0.05% Tween and the monolayer was examined using a fluorescence microscope.

For measurement of cytolytic activity using corneal cell targets, plates containing confluent epithelial cells were washed three times with DPBS to remove the media and then were incubated with 1.0 ml of diafiltered cytotoxin. Respective negative and positive controls included cells with 1.0 ml of DPBS or with 1.0 ml of DPBS to which 10% Triton X was added. Assays were performed in duplicate. After one hour of incubation (37° C.), the culture fluid was removed and the amount of LDH released from the cells was measured as described in *DNAS*, 48:2123-2130 (1962).

EXAMPLE 14

Bacterial Strains and Culture Conditions for Cloning

This example illustrates isolation of pathogenic strains of *M. bovis* and culturing conditions for cloning.

Hemolytic, pathogenic strains of *Moraxella bovis* (strains T+ and Tifton I) were isolated from 2 beef cows infected with IBK. A nonhemolytic mutant (T−) arose spontaneously from T+ subcultures. Isolates were identified as *M. bovis* by colony morphology and biochemical criteria. *Moraxella bovis* was propagated on 5% sheep or cow blood agar plates and strains were stored frozen in 50% skim milk-50% glycerol media at −80° C. Cloning competent *E. coli* strains TOP10 (Invitrogen Corp., Carlsbad, Calif.), DH5α (Life Technologies, Inc., Rockville, Md.), and BL21 (DE3) (Novagen, Madison, Wis.) were propagated in LB broth or on LB agar (1.5% agar; Difco Laboratories, Detroit, Mich.). Antibiotic selection of *E. coli* was made using ampicillin (100 μg/ml).

EXAMPLE 15

Western Blot Analysis

This example describes conditions used for Western blot analysis.

Diafiltered retentate was buffer exchanged into FPLC buffer (50 mM Tris; 1.5 mM $CaCl_2$; 0.9% NaCl; 5% glycerol; pH 8.0) using PD-10 columns (Amersham Pharmacia Biotech, Inc., Piscataway, N.J.), concentrated 10-15 fold (Centriprep-10; Millipore, Beverly, Mass.), filtered through a 0.2 µm filter (Sterile Acrodisc 13; Gelman Sciences), and chromatographed on a Superose 6 gel filtration column (Amersham Pharmacia) in FPLC buffer at room temperature. Column void volume fractions from multiple chromatography runs were pooled and concentrated 5-10 fold (Centriprep 10; Millipore).

For analysis, samples were mixed with an equal volume of 2× loading buffer containing 62.5 mM Tris, pH 6.8, 0.7 M β-mercaptoethanol (Bio-Rad Laboratories, Hercules, Calif.), 20% glycerol, 4.1% sodium dodecyl sulfate (SDS), and 0.2 mg/ml bromophenol blue, heated to 95°-100° C. for 5 minutes, electrophoresed using SDS-PAGE (3.9% stacking/7.5% running), transferred to Immobilon-P (0.45 µM pore size; Millipore), and incubated overnight at room temperature on a rotating shaker in blocking buffer (TSN buffer; 20 mM Tris, 0.9% NaCl, 0.1% Tween 20 (pH 7.4) with 5.5% teleostean gelatin (Sigma, St. Louis, Mo.)). Following incubation, fresh blocking buffer containing rabbit anti-column fraction serum (1:400 dilution) was added and blots were incubated overnight at room temperature on a rotating shaker. The blots were washed 3 times in TSN buffer, then immersed in a solution containing 0.5 µCi of $^{125}$I-labeled Protein A (NEN Life Science Products, Inc., Boston, Mass.) per 20 ml TSN buffer, incubated overnight at room temperature on a rotating shaker, washed and autoradiographed (Hyperfilm MP; Amersham).

EXAMPLE 16

Amino Acid Sequencing

This example describes conditions used for amino acid sequencing.

The concentrated void volume fractions from gel filtration chromatographed diafiltered retentates from T+ were electrophoresed on a SDS-PAGE gel and stained with Coomassie blue. A 70 kDa band that had previously been identified on Western blots as being unique to T+ was excised, digested with trypsin, and tryptic peptides were fractionated by HPLC. Two peptides designated #23 and #26 were selected for N-terminal amino acid sequencing using Edman degradation chemistry. Amino acid sequencing was performed at the Protein Chemistry Laboratory, University of California, Davis (ABI 470A amino acid sequencer; PE Biolsystems, Foster City, Calif.).

EXAMPLE 17

Determination of DNA Sequence of Cytotoxin Gene

This example describes conditions used for determination of DNA sequences of mbxA gene.

All DNA manipulations were performed as recommended by the manufacturers of the enzymes or by using standard published methods. Genomic DNA from *M. bovis* Tifton 1 was isolated as described in *Molecular Cloning: A Laboratory Manual*, 2$^{nd}$ Ed., Cold Spring Harbor Laboratory, Cold Spring Harbor, N.Y. (1989).

Plasmid DNA was isolated with Qiagen plasmid minipreps (Qiagen, Valencia, Calif.). The DNA sequence of the complete cytotoxin gene was obtained by sequencing PCR products directly or PCR products cloned into pCR2.1-TOPO (Invitrogen) with a TOPO TA cloning kit (Invitrogen). Degenerate PCR primers designated primer 23A, depicted by a sequence 5'-AAY AAA GAR TTR GAR GCN GAR-3' (SEQ ID NO: 23) and 26A, depicted by a sequence 5'CCY TCN CCR CTR TGR AAD ATR TCR TTR AAT TT-3' (SEQ ID NO: 24) were designed by reverse translating the amino acid sequences of peptides #23 and #26, respectively, primers C-down, 5'ATH GAY TGG ATH GCN CCN TTY GGN GAY-3' (SEQ ID NO: 25) and B-up, 5'-ACT TTA TCC ATC ACR ACT TGR AAR AA-3' (SEQ ID NO: 26) were designed by reverse translating conserved regions of RTXC and B genes of other bacteria.

PCR amplifications were performed with Taq polymerase (Life Technologies) using 30 cycles of 30 seconds each at 95° C., 1 minute at 55° C., and 45 seconds (primers 23A/26A) or 2 minutes (primers C-down/B-up) at 72° C. PCR products were analyzed by agarose gel electrophoresis. Automated DNA sequencing was performed by the DNA sequencing facility, University of California, Davis. Additional primers were designed as needed for sequencing of overlapping fragments on both strands; the DNA sequences of overlapping fragments were assembled with MacDNASIS (Hitachi Software Engineering Co., Ltd., Yokohama, Japan) to yield the final complete sequence.

EXAMPLE 18

Expression of Recombinant Peptides

This example describes expression of recombinant peptides.

Internal Peptide

The PCR product amplified by primers 23A/26A was cloned into pCR2.1-TOPO (Invitrogen) and the resulting recombinant plasmid was digested with EcoRI. The appropriate fragment was gel purified (QIAquick gel extraction kit, Qiagen) and ligated into pProEXHTa (Life Technologies) digested with EcoRI to yield an expression construct that would direct synthesis of the cytotoxin gene from amino acids 438 through 713. This expression plasmid was introduced into *E. coli* DH5α, cells were grown to an $OD_{600}$ of 0.6, and expression was induced by adding isopropylthio-β-galactoside (IPTG; Life Technologies) to 1 mM. Induction was continued for 4-6 hours and cells were harvested by centrifugation.

The expressed proteins formed inclusion bodies that were purified as described in *Methods Enzymol.,* 153:461 (1987). Purified inclusion bodies were then solubilized in buffer containing 20 mM Tris (pH 8.0), 1 mM EDTA, and 6 M urea and chromatographed on a SuperDex 200 gel filtration column (Amersham Pharmacia). Peak fractions were pooled, dialyzed against phosphate buffered saline (PBS) and stored at −20° C. Following removal of urea, the purified protein formed a precipitate. This protein was designated internal peptide.

Carboxy Peptide

The complete cytotoxin gene was amplified from genomic DNA of *M. bovis* Tifton I with primers designated NdeI-start (5'-GAT CAT ATG TCC AAT ATA AAT GTA ATT AAA TCT AA-3') SEQ ID NO: 27 and B-up #2 (5'ATC ACT AGT TCC ATA ATC TAT AAC CAA TGA-3') SEQ ID NO: 28. This primer pair amplified MbxA from 6 bases before the ATG start codon to 64 bases past the termination codon and introduced an NdeI restriction site overlapping the ATG start codon. The PCR conditions were as described above except that the elongation step was for 1 minute at 72° C.

The PCR product was cloned into pCR2.1-TOPO (Invitrogen). The resulting recombinant plasmid was digested with XhoI-EcoRI and blunt ended with Klenow polymerase (Life Technologies). The appropriate fragment was gel purified, then cloned into blunted ended, BamHI digested and Klenow blunt ended pT7-7 to yield an expression construct that would direct synthesis of the cytotoxin gene from amino acids 643 through 927.

Recombinant plasmids were transformed into *E. coli* DH5α, and subsequently purified (Qiagen miniprep kit; Qiagen) prior to transformation into *E. coli* strain BL21 (DE3) (Novagen, Madison, Wis.) for expression. The cells were grown and induced as described above to produce the recombinant protein, except that for protein purification, inclusion bodies were solubilized in buffer containing 10 mM Tris (pH 8.0), 1 mM EDTA, and 8 M urea, and chromatographed on a Mono Q column (Amersham Pharmacia). Peak fractions were identified by SDS-PAGE, pooled and then chromatographed on a SuperDex 200 gel filtration column. Peak fractions from the SuperDex 200 column were pooled, dialyzed against PBS, and stored at −20° C. This protein, which remained soluble following dialysis, was designated carboxy peptide.

EXAMPLE 19

Preparation of Rabbit Antisera

This example describes preparation of rabbit antisera for recombinant cytotoxin identification and confirmation.

Antisera was prepared by immunizing New Zealand White rabbits with either the pooled void volume fractions or Superose 6 gel-filtration chromatographed diafiltered retentates of *M. bovis* T+ mixed 1:1 (v/v) with Freund's complete adjuvant. Booster vaccinations were performed 21 days later with either the pooled column fractions or culture filtrates mixed 1:1 with Freund's incomplete adjuvant, and serum was harvested 21 days post booster. Sera against the pooled column fractions was designated rabbit anti-column fraction. The sera against the culture filtrates was designated rabbit anti T+. This antisera neutralized hemolytic and cytolytic activity of partially purified *M. bovis* cytotoxin.

Polyclonal rabbit antisera to the internal (amino acids 438 through 713) and carboxy (amino acids 643 through 927) peptides expressed from MbxA were prepared commercially (Antibodies Incorporated, Davis, Calif.). Before use in immunoblots, this antisera was preabsorbed with an *E. coli* DH5α lysate. Sera were heat inactivated at 56° C. for 1 hour prior to lysis neutralization assays.

EXAMPLE 20

Demonstration of Cytotoxin in Culture Supernatants

This example describes conditions used for demonstration of the presence of cytotoxin in culture supernatant.

*Moraxella bovis* T+, T−, or Tifton I was inoculated into LB broth containing 1.5 mM $CaCl_2$ and incubated for 3-6 hours with shaking at 250 rpm at 35° C. Following incubation, cultures were centrifuged and the supernatants were harvested and analyzed by SDS-PAGE/transblotting, using rabbit antiserum against the internal or carboxy peptide as the primary antibody.

EXAMPLE 21

Lysis Neutralization Assays

This example describes assays performed to study cytolysis neutralization and hemolysis neutralization.

Serum test samples were diluted 1:64 in TBS $CaCl_2$ buffer (50 mM Tris, 150 mM NaCl, 1.5 mM $CaCl_2$, pH 7.4) and an equal volume of either TBS $CaCl_2$ buffer or carboxy peptide diluted in TBS $CaCl_2$ buffer (0.1 mg/ml) was added. The samples were incubated at room temperature for 30 minutes, then at 37° C. for 30 minutes, and then centrifuged at maximum speed in a microcentrifuge for 10 minutes. The supernatants were then harvested and mixed with an equal volume of Tifton I diafiltered retentate diluted 1:32 in TBS $CaCl_2$ buffer. The test samples were incubated for 1 hour at 4° C. after which hemolysis or cytolysis neutralization assays were performed as described below.

For hemolysis neutralization assays, 500 µl of 1% (v/v) suspension of washed and pelleted bovine erythrocytes in TBS $CaCl_2$ buffer was added to 500 µl of each test sample, incubated for 6 hours at 37° C., the samples were inverted once, centrifuged for 1 minute at maximum speed in a microcentrifuge, and 350 µl of supernatant was transferred to a 96 well microtiter plate for determination of the $OD_{455}$ (Spectra Max 250, Molecular Devices Corporation, Sunnyvale, Calif.). Respective negative and positive controls were TBS $CaCl_2$ buffer or Tifton I diafiltered retentate diluted 1:32 in TBS $CaCl_2$ buffer. A control for the carboxy peptide in TBS $CaCl_2$ buffer was also included. The percent hemolysis was determined using the formula:

$$\% \text{ hemolysis} = \left[\frac{\text{sample } OD - \text{lysis negative control } OD}{\text{positive control } OD - \text{lysis negative control } OD}\right] \times 100$$

The percent neutralization was calculated by subtracting the percent hemolysis from 100. The results reflect the means from three experiments.

The target cells for cytolysis neutralization assays were labeled bovine lymphocytes (BL-3 cells); supplied by Dr. Gordon Thielen, University of California, Davis. These were prepared by growing cells from frozen stock cultures at 37° C. in 6% $CO_2$ in Liebovitz L-15 medium (Life Technologies) and Minimal Essential Media (Life Technologies) (1:1 v/v) supplemented with penicillin (50 U/ml), streptomycin (50 ug/ml) (Life Technologies), and 15% heat inactivated fetal bovine serum (Hyclone, Logan Utah). Cells were harvested by centrifugation, washed 3 times in PBS, resuspended in McCoys 5A media (Life Technologies) to a final concentration of $2 \times 10^7$/ml, labeled for 1 hour at 37° C. with 200 µCi of $^{51}Cr$ (NEN Life Science Products) while rotating at 20 revolutions per minute, and then washed 3 times in McCoys 5A media. Following the final wash, cells were diluted in McCoys 5A media to a final concentration of $4 \times 10^5$/ml.

For cytolysis neutralization assays, 500 µl of labeled BL-3 cells were added to 500 µl of each test sample, incubated for 1 hour at 37° C. while rotating at 20 revolutions per minute, pelleted in a microcentrifuge, and the radioactivity in 500 µl of supernatant was determined. Negative and positive controls were as described above for hemolysis neutralization assays. The percent cytolysis was determined using the formula:

$$\% \text{ cytolysis} = \left[ \frac{\text{specimen counts per minute } (cpm) - \text{negative control } cpm}{\text{positive control } cpm - \text{negative control } cpm} \right] \times 100$$

The percent neutralization was calculated by subtracting the percent cytolysis from 100. The results reflect means obtained from three experiments.

EXAMPLE 22

Amino Acid Sequence Analysis

This example describes methods used in amino acid sequence analysis.

The relationships between the deduced amino acid sequences and published protein sequences were determined with BLAST database searches. Multiple sequence analyses, alignments, and homology calculations were obtained using the blosum 62 amino acid substitution matrix (SEQWEB software (version 1.1); Genetics Computer Group, Madison, Wis.). The nucleotide sequence for the *M. bovis* cytotoxin gene has been submitted to the GENBANK database under accession number AF205359.

EXAMPLE 23

Field Trials With Native Cytotoxin Vaccine

This example describes conditions used in field trials with native cytotoxin based vaccine.

Experimental Subjects

Cattle for the study were part of the herd at the University's Sierra Foothills Field station. The ranch was located in the foothills of the northern Sierra Nevadas at an altitude ranging between 800 and 2400 feet. The subjects included 104 Hereford Angus crossbred yearling calves. The calves, which were born during November and December of the previous year, weighed between 90 and 300 kg, and were composed of equal numbers of females and castrated males. Calves were commingled into a single group and were pastured on either of 2 irrigated fields. Other than the pasture forage and trace mineralized salt licks, cattle were not supplemented during the summer. The calves were housed out of doors on irrigated pastures on approximately 100 acres. Pasture forages were composed of Bermuda, fescue, oats, and rye grasses, and smaller amounts of trefoil and clovers, and other plants that were indigenous to the area. For the previous decade, yearling calves at the ranch had an annual prevalence of IBK that exceeded 50%.

Study Design

The study was conducted between the dates of May and September. In the May examination, calves were prospectively and randomly allocated to one of 3 groups designated A, B or C. For examination, the calves were restrained in a squeeze chute, and fluorescein dye was instilled into each eye prior to illumination with a light source. Eyes were assigned a clinical score ranging between 0 and 3 with 3 representing an eye that had ruptured, and had expelled the contents. Criteria for lower clinical ocular scores included: 0=no conjunctivitis or corneal ulcer; 1=conjunctivitis with a corneal ulcer having a maximum diameter that was ≦0.5 cm, and 2=a corneal ulcer having a maximum diameter that was >0.5 cm. Eyes with corneal ulcers were photographed during each examination. Each photographic image included a ruler held on the lower eyelid.

After application of the fluorescein dye, eyes with corneal ulcer scores≧1 were photographed at a constant magnification, and the image was projected onto paper and traced. The surface area of each traced image was measured planimetrically as described. During the first examination in April (Day 1), calves with normal eyes were randomly assigned to one of 3 groups. Calves of the first group (n=34) were given 2 ml of sterile saline solution. Calves of the second group (n=35) were given 2 ml of a cytotoxin enriched, sterile Quil A adjuvanted vaccine. Calves of the third group (n=35) were given 2 ml of a mixture of sterile adjuvant and saline (1:1, v/v). All injections were made subcutaneously in the neck. Calves were boostered with the corresponding product in June. Thereafter, clinical examinations were performed weekly for 15 weeks.

Personnel responsible for administering the vaccine, evaluating the clinical scores and for measuring the corneal ulcer diameters had no knowledge of the group assignment of the calves. Each week, calves with corneal ulcer scores ranging between 0 and 1 in either eye were returned to the common pasture. Calves with ulcer scores of 2 or 3 were treated with florfenicol (Nuflor®, 20 mg/kg of body weight intramuscularly) and were housed in a corral until they were retreated 48 hours later. After the second florfenicol treatment, the calves were moved back to their original pasture and were observed weekly for the remainder of the study.

Vaccines

Calves of group A were given 2.0 ml of a vaccine composed of Quil A adjuvanted, diafiltered concentrated cell free cytotoxin from a toxigenic, hemolytic, non piliated strain of *Moraxella bovis*. Calves of the second group were sham vaccinated with Quil A adjuvant in phosphate buffered saline solution. The third group of calves received 2.0 ml of sterile saline solution. The original piliated strain of *M. bovis* was derived from the eye of an infected cow located in northern California and was identified using biochemical tests described previously. Non piliated isolates were identified during repeated subcultures on blood agar plates. These isolates, devoid of pili, were smooth, did not pit the surface of the agar, and remained homogeneously suspended in broth cultures. Lack of piliation was confirmed using electron microscopy.

Stocks of the pilin negative isolate were stored frozen (−80° C.). For vaccine production, stocks were thawed at room temperature and inoculated onto a bovine blood agar plate lawns. After 18 hours of incubation (37° C.), the lawns were harvested and were suspended in flasks containing brain heart broth (1 lawn per 500 ml) supplemented 1.5 mM of $CaCl_2$. The flasks were shaken (200 rpm) for 5 hours (37° C.). After incubation, the broth cultures were centrifuged for one hour at 13,000×g (4° C.) and supernatants were harvested and were filter sterilized (0.2 μM average pore diameter; Gelman Sciences, Ann Arbor, Mich.). The sterile supernatant was concentrated approximately 40-fold to a final volume of 200 ml by ultrafiltration over a spiral wrapped membrane (molecular weight cut off of 100,000 daltons) of regenerated cellulose (S1Y100 CH2PRS membrane, Amixon Inc, Beverly, Mass.). The concentrated retentate was then diafiltered using 50 volumes 50 mM Tris, pH 8.2, 50 mM sodium acetate, 1.5 mM $CaCl_2$, and 20% glycerol (v/v).

Diafiltration was discontinued when the optical density of the permeate was <0.01 optical density units. Approximately 200 ml of diafiltered retentate was collected, and the protein content was measured using the Lowry method. The specific cytotoxic and hemolytic activities of the diafiltered retentates were greater than those of the concentrated permeates.

The experimental vaccine preparation was made by diluting the diafiltered retentate to achieve a final concentration of 0.8 mg/ml, and then adding 0.25% (w/v) MEGA-10 (Cal Biochem, San Diego, Calif.). For the adjuvant control vaccine, an equivalent volume of Tris acetate calcium chloride, glycerol buffer was used in place of the diafiltered retentate. To both solutions, Quil A (Iscotec, Sweden) was added to a final concentration of 0.1%. The mixtures were then placed in dialysis membranes with 2000 kDa molecular weight cut off, and were dialyzed against repeated changes of sterile Dulbecco's phosphate buffered saline solution (GIBCO BRL, Grand Island, N.Y.) for 48 hours at 4° C. After 48 hours, the contents of the dialysis tubing were filter sterilized, and kept refrigerated (4° C.) until administered to the subjects 48 hours later.

Statistical Evaluation of Data

Data including number of calves in each group that were infected, on each date, cumulative numbers of affected calves, and number of corneal ulcers in calves of each group during the weekly evaluation, were compared using the Chi squared analysis. In order to avoid statistical errors caused by repeated measurements in eyes that had more chronic ulcers, data from each week were evaluated independently. Corneal ulcer surface measurements of the calves were compared among groups using the analysis of variance test. Clinical score data were compared across the 3 groups each week using the Kruskal-Wallis test, with inter-group comparisons being made with the Mann-Whitney rank sum test. The data were considered to be significantly different when the p value was $\leq 0.05$. Eyes with recurrences of corneal ulcers were not included in the statistical analyses, but the numbers of recurrences were noted and compared between the 3 groups using the Chi squared analysis.

EXAMPLE 24

Field Trials With Recombinant Vaccine

This example describes conditions used in field trials with recombinant anti-*M. bovis* vaccine.

Experimental Subjects

The study population consisted of calves at the University's Sierra Foothills Field Station (SFS), located in Brown's Valley, Calif. The terrain consisted of Sierra foothill range pasture. The animals were predominantly Angus or Angus-Hereford crossbred calves. Calves weighed between 98 and 292.7 kg. The study population consisted of 20 intact males, 71 steers, and 2 heifers.

Study Design

Pre-enrollment Examination

Each calf was restrained in a head catch and both eyes were examined for the presence of corneal opacities indicative of prior ocular disease. Only calves with normal corneas were selected for the study. On day 0, calves were administered a 2 ml subcutaneous injection of either saline (CTRL group), ISCOM matrix adjuvant alone (ADJ group), or recombinant *M. bovis* cytotoxin-ISCOM matrix adjuvant (VAC group). Calves were randomly assigned to one of the three groups by use of a blocked randomization scheme. Individuals administering vaccine were unaware of the vaccine contents administered. Booster vaccinations were repeated on day 21.

Post-enrollment Examination

Each calf was examined weekly for 20 weeks following the primary vaccination. During these examinations, eyes were examined for the presence of corneal opacities. All eyes with corneal opacification were stained with fluorescein dye, irrigated with sterile isotonic saline solution, and assigned a corneal ulcer score (CUS) of 0, 1, 2, or 3 l based on the widest diameter of the ulcer as determined by holding a ruler next to the eye. The scoring criteria were: 0=no ulcer; 1=a corneal ulcer with the widest diameter$\leq 5$ mm: 2=a corneal ulcer with the widest diameter>5 mm: and 3=a perforating corneal ulcer. Ulcerated eyes were photographed with a ruler held next to the eye for determination of the corneal ulcer surface area measurement (SAM) as described below. Any calves with a CUS of 2 or greater were administered florfenicol (40 mg/kg subcutaneously). To minimize iatrogenic infections, garments including plastic aprons, obstetrical sleeves, and rubber gloves were worn and were rinsed in 1% chlorhexidine solution after each animal was examined.

Bacterial Strains and Culture Conditions

Cloning competent *E. coli* strains TOP10, DH5α, and BL21 (DE3) were propagated in LB broth or on LB agar (1.5% agar). Antibiotic selection of *E. coli* was made using ampicillin (100 ug/ml).

Expression of Recombinant *M. bovis* Cytotoxin

The carboxy terminus of the *M. bovis* cytotoxin gene was amplified with primers SNP down (5'-AAT GAC GAT ATC TTT GTT GGT CAA GGT AAA-3') and LNP2 (5'-TAG TAA ATT AAA TNA CTW AAC ACT-3'). PCR amplifications were performed with Taq polymerase using 30 cycles of 30 seconds each at 95° C., 1 minute at 55° C., and 45 seconds at 72° C., followed by a 10 mm incubation at 72° C. The PCR product was cloned into pCR2.1-TOPO with a TOPO TA cloning kit and the resulting recombinant plasmid was digested with EcoRI. The appropriate fragment was gel purified (QIAquick gel extraction kit) and cloned into blunted ended, SmaI digested pT7-7 to yield an expression construct that would direct synthesis of the cytotoxin gene from amino acids 590 through 927. Recombinant plasmids were transformed into *E. coli* DH5α, and subsequently purified prior to transformation into *E. coli* strain BL21 (DE3) for expression. Cells were grown to an $OD_{600}$ of 0.8, and expression was induced by adding isopropylthio-β-galactoside to 1 mM. Induction was continued for approximately 9 hours and cells were harvested by centrifugation. The expressed proteins formed inclusion bodies that were purified. Purified inclusion bodies were then solubilized in a buffer containing 4 M urea, 0.25% Triton X-100, 5 mM Tris-HCl (HCl pH 7.5) and 1 mM EDTA and chromatographed (Mono Q column; Amersham Pharmacia). Peak fractions were identified by SDS-PAGE, pooled and protein was quantitated with a BCA kit using a bovine serum albumin standard. The protein solution was sterile filtered and dialyzed against PBS to remove urea and stored at −20° C. Following dialysis the purified protein precipitated. PBS was added to the dialysate to make the final protein concentration 0.5 mg/ml.

Vaccine PreDaration

ISCOM matrices were prepared as described in *Current Protocols in Immunology*, Caligan, John E., Ed. New York, Greene Publication Associates and Wiley-InterScience, except that no protein was incorporated into the ISCOMs. Instead, the purified recombinant protein was mixed separately with ISCOMs following ISCOM matrix formation. A lipid mixture containing 50 mg/ml each of phosphatidylcholine and cholesterol was made by dissolving 100 mg of each in 1 ml of chloroform and combining both solutions. This lipid mixture was then added to a 20% solution (w/v) of decanoyl-N-methylglucamide (Mega 10) made by dissolving 2 g Mega 10 in 10 ml distilled water. The resulting solution was added to phosphate buffered saline (PBS; pH 7.4) (0.1 cc lipid mixture per 1 ml PBS) and the chloroform was removed by heating the solution to 45° C. under vacuum until the solution cleared. Quil A was then added to a final concentration of 1 mg/ml. The solution was transferred to dialysis tubing (2000 MW cut-off) and dialyzed extensively for 3 days in 50 mM Tris-HCl, 0.001% thimerosal, pH 7.5 at room temperature. Thimerosal was removed by dialysis against PBS (pH 7.4) for 24-36 hours at 4° C. Following dialysis the solution was sterile filtered (0.45 or 0.2 μM pore size) and stored at −20° C. until use. The success of ISCOM matrix formation was confirmed by electron microscopy performed at the Department of Medical Pathology, School of Medicine, UC Davis.

For vaccine production, 145 ml of ISCOM dialysate was made to 180 ml with PBS (pH 7.4). For the adjuvant control vaccine (ADJ), the ISCOM matrix preparation was mixed with PBS (pH 7.4) 1:1. For the recombinant protein vaccine (VAC), the ISCOM matrix preparation was mixed 1:1 with the recombinant protein solution. The doses were 2 ml of adjuvant (ADJ) and vaccine (VAC) for both primary and booster vaccinations. The control (CTRL) vaccine was a 2 ml dose of 0.9% saline.

SAM Determination

Color slides were projected onto a standardized ruler template to equalize magnifications for subsequent tracing of corneal ulcers. Three free-hand drawings of each ulcer were made on paper. Tracing images were digitized and corneal ulcer surface areas were determined with NIH-image (version 1.62). The mean ulcer size was determined from the three tracings. The limit of detection was 0.008 $cm^2$, the area that corresponded to a 1 mm diameter circle. Surface areas less than this were excluded from analysis. Corneal ulcers resulting from scratches were excluded from the analysis. Ulcers resulting from foxtails or suspect foxtails were not included in the analysis on the first week the ulcer was first noted. If eyes remained ulcerated on subsequent weeks, SAM were entered into the analysis.

Data Analysis

The cumulative number of calves with corneal ulcer SAM>0.008 was determined each week for the 20 week trial period. For this analysis, calves were only counted one time. Chi-square analysis was used to compare differences in the cumulative numbers of calves with corneal ulcers during each week. Commercial software (Statview and SPSS were used for statistical analyses). Differences were considered significant at $P<0.05$.

What is claimed:

1. An isolated peptide consisting of the amino acid sequence depicted by SEQ ID NO: 6.

2. An isolated peptide consisting of the amino acid sequence depicted by SEQ ID NO: 13.

3. A composition comprising a polypeptide, wherein the polypeptide is selected from:
   a) a polypeptide comprising amino acids 438 through 713 of SEQ ID NO: 2, inclusive, wherein the polypeptide is shorter than the polypeptide provided by SEQ ID NO: 2;
   b) a polypeptide comprising amino acids 590 through 927 of SEQ ID NO: 2, inclusive, wherein the polypeptide is shorter than the polypeptide provided by SEQ ID NO: 2; and,
   c) a polypeptide comprising amino acids 643 through 927 of SEQ ID NO: 2, inclusive, wherein the polypeptide is shorter than the polypeptide provided by SEQ ID NO: 2.

4. The composition of claim 3, wherein the polypeptide of (a), (b) or (c) further comprises a 6×His tag.

5. The composition of claim 3, wherein the polypeptide of (a), (b) or (c) further comprises a second polypeptide, wherein the polypeptide and the second polypeotide are joined to each other as a fusion polypeptide.

* * * * *